US009228020B2

(12) United States Patent
Gurney et al.

(10) Patent No.: US 9,228,020 B2
(45) Date of Patent: *Jan. 5, 2016

(54) COMPOSITIONS AND METHODS FOR DIAGNOSING AND TREATING CANCER

(71) Applicant: OncoMed Pharmaceuticals, Inc., Redwood City, CA (US)

(72) Inventors: Austin L. Gurney, San Francisco, CA (US); Fumiko Takada Axelrod, Palo Alto, CA (US); Timothy Charles Hoey, Hillsborough, CA (US); Sanjeev H. Satyal, San Carlos, CA (US)

(73) Assignee: OncoMed Pharmaceuticals, Inc., Redwood City, CA (US)

( * ) Notice: Subject to any disclaimer, the term of this patent is extended or adjusted under 35 U.S.C. 154(b) by 64 days.

This patent is subject to a terminal disclaimer.

(21) Appl. No.: 13/826,103

(22) Filed: Mar. 14, 2013

(65) Prior Publication Data

US 2013/0266569 A1 Oct. 10, 2013
US 2014/0147443 A9 May 29, 2014

Related U.S. Application Data

(60) Division of application No. 12/782,429, filed on May 18, 2010, which is a continuation of application No. 11/905,392, filed on Sep. 28, 2007, now Pat. No. 7,750,124.

(60) Provisional application No. 60/847,904, filed on Sep. 29, 2006, provisional application No. 60/886,260, filed on Jan. 23, 2007, provisional application No. 60/942,542, filed on Jun. 7, 2007.

(51) Int. Cl.
*A61K 39/395* (2006.01)
*C07K 16/30* (2006.01)
*A61K 45/06* (2006.01)
*A61K 39/00* (2006.01)

(52) U.S. Cl.
CPC ........... *C07K 16/30* (2013.01); *A61K 39/39558* (2013.01); *A61K 45/06* (2013.01); *A61K 2039/505* (2013.01); *A61K 2039/507* (2013.01); *C07K 2316/96* (2013.01); *C07K 2317/24* (2013.01); *C07K 2317/56* (2013.01); *C07K 2317/565* (2013.01); *C07K 2317/73* (2013.01)

(58) Field of Classification Search
None
See application file for complete search history.

(56) References Cited

U.S. PATENT DOCUMENTS

| | | | |
|---|---|---|---|
| 3,773,919 A | 11/1973 | Boswell et al. |
| 4,485,045 A | 11/1984 | Regen |
| 4,544,545 A | 10/1985 | Ryan et al. |
| 4,816,567 A | 3/1989 | Cabilly et al. |
| 5,013,556 A | 5/1991 | Woodle et al. |
| 5,545,806 A | 8/1996 | Lonberg et al. |
| 5,545,807 A | 8/1996 | Surani et al. |
| 5,569,825 A | 10/1996 | Lonberg et al. |
| 5,585,089 A | 12/1996 | Queen et al. |
| 5,625,126 A | 4/1997 | Lonberg et al. |
| 5,633,425 A | 5/1997 | Lonberg et al. |
| 5,641,870 A | 6/1997 | Rinderknecht et al. |
| 5,661,016 A | 8/1997 | Lonberg et al. |
| 5,693,761 A | 12/1997 | Queen et al. |
| 5,693,762 A | 12/1997 | Queen et al. |
| 5,730,977 A | 3/1998 | Ooka et al. |
| 5,731,168 A | 3/1998 | Carter et al. |
| 5,750,373 A | 5/1998 | Garrard et al. |
| 5,840,299 A | 11/1998 | Bendig et al. |
| 6,004,528 A | 12/1999 | Bergstein |
| 6,024,955 A | 2/2000 | Asano et al. |
| 6,121,045 A | 9/2000 | McCarthy et al. |
| 6,262,025 B1 | 7/2001 | Ish-Horowicz et al. |
| 6,342,219 B1 | 1/2002 | Thorpe et al. |
| 6,524,583 B1 | 2/2003 | Thorpe et al. |
| 6,582,959 B2 | 6/2003 | Kim |
| 6,664,098 B1 | 12/2003 | Sakano |
| 6,676,941 B2 | 1/2004 | Thorpe et al. |
| 6,689,744 B2 | 2/2004 | Gao et al. |
| 6,887,468 B1 | 5/2005 | Thorpe et al. |
| 6,984,522 B2 | 1/2006 | Clarke et al. |
| 7,022,499 B2 | 4/2006 | Sakano |
| 7,056,509 B2 | 6/2006 | Thorpe et al. |
| 7,060,269 B1 | 6/2006 | Baca et al. |
| 7,118,890 B2 | 10/2006 | Ish-Horowicz et al. |
| 7,183,076 B2 | 2/2007 | Arathoon et al. |
| 7,227,004 B2 | 6/2007 | Kim |

(Continued)

FOREIGN PATENT DOCUMENTS

| CA | 2789446 A1 | 8/2011 |
|---|---|---|
| EP | 1 004 669 B1 | 5/1998 |

(Continued)

OTHER PUBLICATIONS

Al-Hajj, M., et al., "Prospective identification of tumorigenic breast cancer cells," *Proc. Nat. Acad Sci.* 100(7):3983-3988, National Academy of Sciences, Washington, DC, USA (Apr. 2003).

Benvenuti, et al., "Oncogenic Activation of the RAS/RAF Signaling Pathway Impairsthe Response of Metastatic Colorectal Cancers to Anti-Epidermal Growth Factor Receptor Antibody Therapies," *Cancer Res.* 67(6):2643-2648, American Association for Cancer Research, USA (Mar. 2007).

Chau, I. and Cunningham, D., "Treatment in advanced colorectal cancer: what, when and how?," *British Journal of Cancer* 100(11):1704-1719, Cancer Research UK, England (May 2009).

(Continued)

*Primary Examiner* — Lei Yao
(74) *Attorney, Agent, or Firm* — Sterne, Kessler, Goldstein & Fox PLLC

(57) ABSTRACT

An isolated antibody that specifically binds to an extracellular domain of human DLL4 and affects growth of a tumor comprising cancer stem cells is described. Also described is a method of treating cancer comprising administering a therapeutically effective amount of an anti-DLL4 antibody.

32 Claims, 24 Drawing Sheets

(56) References Cited

U.S. PATENT DOCUMENTS

| | | |
|---|---|---|
| 7,354,581 B2 | 4/2008 | Cedarbaum et al. |
| 7,449,182 B2 | 11/2008 | Cedarbaum et al. |
| 7,482,005 B2 | 1/2009 | Kim |
| 7,488,806 B2 | 2/2009 | Papadopoulos et al. |
| 7,531,172 B2 | 5/2009 | Stahl et al. |
| 7,534,868 B1 | 5/2009 | Papadopoulos et al. |
| 7,750,124 B2 | 7/2010 | Gurney et al. |
| 7,754,206 B2 | 7/2010 | Clarke et al. |
| 7,758,859 B2 | 7/2010 | Fuh et al. |
| 7,951,917 B1 | 5/2011 | Arathoon et al. |
| 8,048,418 B2 | 11/2011 | Noguera-Troise et al. |
| 8,216,571 B2 | 7/2012 | Ramachandra et al. |
| 8,858,941 B2 | 10/2014 | Gurney et al. |
| 8,883,145 B2 | 11/2014 | Stagg et al. |
| 2002/0028488 A1 | 3/2002 | Singh et al. |
| 2002/0032315 A1 | 3/2002 | Baca et al. |
| 2003/0175877 A1 | 9/2003 | Baker et al. |
| 2003/0180784 A1 | 9/2003 | McCarthy et al. |
| 2004/0123343 A1 | 6/2004 | La Rosa et al. |
| 2004/0133357 A1 | 7/2004 | Zhong et al. |
| 2004/0265307 A1 | 12/2004 | Singh et al. |
| 2004/0265309 A1 | 12/2004 | Kandel et al. |
| 2005/0026831 A1 | 2/2005 | Bodmer et al. |
| 2005/0054036 A1 | 3/2005 | Bates et al. |
| 2005/0059093 A1 | 3/2005 | Bodmer et al. |
| 2005/0079184 A1 | 4/2005 | Hsing-Chang et al. |
| 2005/0089518 A1 | 4/2005 | Clarke et al. |
| 2005/0112121 A1 | 5/2005 | Artavanis-Tsakonas et al. |
| 2005/0137130 A1 | 6/2005 | Bodmer et al. |
| 2005/0261477 A1 | 11/2005 | Champion et al. |
| 2005/0276808 A1 | 12/2005 | Cedarbaum et al. |
| 2005/0281822 A1 | 12/2005 | Cedarbaum et al. |
| 2006/0084588 A1 | 4/2006 | Briend et al. |
| 2006/0122373 A1 | 6/2006 | McCarthy et al. |
| 2006/0134080 A1 | 6/2006 | Lyden et al. |
| 2006/0134121 A1 | 6/2006 | Thurston et al. |
| 2006/0280747 A1 | 12/2006 | Fuh et al. |
| 2007/0004909 A1 | 1/2007 | Johnson et al. |
| 2007/0020267 A1 | 1/2007 | Fuh et al. |
| 2007/0036797 A1 | 2/2007 | Kim et al. |
| 2007/0082846 A1 | 4/2007 | Ish-Horowicz et al. |
| 2007/0098712 A1 | 5/2007 | Arathoon et al. |
| 2007/0141065 A1 | 6/2007 | Fuh et al. |
| 2007/0154391 A1 | 7/2007 | Kim |
| 2007/0178552 A1 | 8/2007 | Arathoon et al. |
| 2007/0190647 A1 | 8/2007 | Clarke et al. |
| 2007/0196374 A1 | 8/2007 | Baca et al. |
| 2007/0202102 A1 | 8/2007 | Bizzini et al. |
| 2007/0212354 A1 | 9/2007 | Yung et al. |
| 2007/0213266 A1 | 9/2007 | Gill et al. |
| 2007/0231325 A1 | 10/2007 | Clarke et al. |
| 2007/0287170 A1 | 12/2007 | Davis et al. |
| 2008/0014196 A1 | 1/2008 | Yan |
| 2008/0063635 A1 | 3/2008 | Takahashi et al. |
| 2008/0069820 A1 | 3/2008 | Fuh et al. |
| 2008/0107648 A1 | 5/2008 | Noguera et al. |
| 2008/0175847 A1 | 7/2008 | Yan et al. |
| 2008/0181893 A1 | 7/2008 | Lobov et al. |
| 2008/0181899 A1 | 7/2008 | Papadopoulos et al. |
| 2008/0220495 A1 | 9/2008 | McCarthy et al. |
| 2009/0004205 A1 | 1/2009 | Clarke et al. |
| 2009/0023591 A1 | 1/2009 | Spanuth |
| 2009/0035308 A1 | 2/2009 | Gill et al. |
| 2009/0221549 A1 | 9/2009 | Gerber et al. |
| 2009/0246199 A1 | 10/2009 | Noguera-Troise et al. |
| 2009/0286956 A1 | 11/2009 | McCarthy et al. |
| 2010/0015133 A1 | 1/2010 | Igawa et al. |
| 2010/0076178 A1 | 3/2010 | Ghayur et al. |
| 2010/0086544 A1 | 4/2010 | Mass et al. |
| 2010/0129356 A1 | 5/2010 | Yan |
| 2010/0150940 A1 | 6/2010 | Adam et al. |
| 2010/0215779 A1 | 8/2010 | Currie et al. |
| 2010/0221250 A1 | 9/2010 | Kim et al. |
| 2010/0260668 A1 | 10/2010 | Ghayur et al. |
| 2010/0266589 A1 | 10/2010 | Hedrick et al. |
| 2010/0272733 A1 | 10/2010 | Bates et al. |
| 2010/0286374 A1 | 11/2010 | Kannan et al. |
| 2010/0316637 A1 | 12/2010 | Gurney et al. |
| 2011/0052575 A1 | 3/2011 | Baca et al. |
| 2011/0052576 A1 | 3/2011 | Ferrara et al. |
| 2011/0076279 A1 | 3/2011 | Ramachandra et al. |
| 2011/0081342 A1 | 4/2011 | Baca et al. |
| 2011/0123532 A1 | 5/2011 | Gurney et al. |
| 2011/0165162 A1 | 7/2011 | Hoey et al. |
| 2011/0172398 A1 | 7/2011 | Borges et al. |
| 2011/0217237 A1 | 9/2011 | Chen et al. |
| 2012/0116057 A1 | 5/2012 | Kannan et al. |
| 2013/0164295 A1 | 6/2013 | Gurney et al. |
| 2013/0253172 A1 | 9/2013 | Gurney et al. |
| 2013/0266569 A1 | 10/2013 | Gurney et al. |
| 2013/0323265 A1 | 12/2013 | Stagg et al. |
| 2014/0147443 A9 | 5/2014 | Gurney et al. |
| 2014/0220001 A1 | 8/2014 | Benner et al. |
| 2014/0227252 A1 | 8/2014 | Benner et al. |
| 2015/0098949 A1 | 4/2015 | Gurney et al. |

FOREIGN PATENT DOCUMENTS

| | | |
|---|---|---|
| EP | 0 861 894 A1 | 9/1998 |
| EP | 0 662 827 B1 | 4/2002 |
| EP | 0662827 B1 | 4/2002 |
| EP | 1 179 541 B1 | 6/2004 |
| EP | 0 979 281 B1 | 7/2005 |
| EP | 0 972 041 B1 | 10/2006 |
| EP | 1 810 979 A1 | 7/2007 |
| EP | 1 870 459 A1 | 12/2007 |
| EP | 2 066 694 A2 | 6/2009 |
| EP | 2 235 064 | 7/2009 |
| EP | 2 483 314 | 4/2011 |
| EP | 2 424 567 A0 | 3/2012 |
| GB | 2 449 354 A | 11/2008 |
| JP | 2005-511754 A | 4/2005 |
| WO | WO 92/19734 | 11/1992 |
| WO | WO 94/07474 | 4/1994 |
| WO | WO 97/01571 A1 | 1/1997 |
| WO | WO 98/45434 A1 | 10/1998 |
| WO | WO-9845331 A2 | 10/1998 |
| WO | WO 98/51799 | 11/1998 |
| WO | WO-9849302 A1 | 11/1998 |
| WO | WO 98/57621 A1 | 12/1998 |
| WO | WO 00/06726 A2 | 2/2000 |
| WO | WO-0107611 A2 | 2/2001 |
| WO | WO 01/40466 A2 | 6/2001 |
| WO | WO-0177169 A2 | 10/2001 |
| WO | WO 02/12447 | 2/2002 |
| WO | WO 03/041735 A2 | 5/2003 |
| WO | WO 03/050502 A2 | 6/2003 |
| WO | WO 2004/110490 A2 | 12/2004 |
| WO | WO 2006/027693 A2 | 3/2006 |
| WO | WO 2006/028936 A2 | 3/2006 |
| WO | WO 2006/033386 A1 | 3/2006 |
| WO | WO 2006/052128 A1 | 5/2006 |
| WO | WO 2006/106905 A1 | 10/2006 |
| WO | WO 2007/028110 A2 | 3/2007 |
| WO | WO 2007/070671 A2 | 6/2007 |
| WO | WO 2007/143689 A2 | 12/2007 |
| WO | WO 2007/145840 A2 | 12/2007 |
| WO | WO 2007/147901 A1 | 12/2007 |
| WO | WO 2008/042236 A2 | 4/2008 |
| WO | WO 2008/060705 | 5/2008 |
| WO | WO 2008/070042 A2 | 6/2008 |
| WO | WO 2008/076379 A2 | 6/2008 |
| WO | WO 2008/079326 A2 | 7/2008 |
| WO | WO 2008/091222 A1 | 7/2008 |
| WO | WO 2008/139202 A1 | 11/2008 |
| WO | WO 2009/075565 A1 | 6/2009 |
| WO | WO 2009/080251 A1 | 7/2009 |
| WO | WO 2009/085209 A2 | 7/2009 |
| WO | WO 2009/089004 A1 | 7/2009 |
| WO | WO 2010/054010 A1 | 5/2010 |
| WO | WO 2010/124009 A2 | 10/2010 |
| WO | WO-2010124009 A2 | 10/2010 |
| WO | WO 2010/129304 A2 | 11/2010 |
| WO | WO 2011/039370 A1 | 4/2011 |

(56) References Cited

FOREIGN PATENT DOCUMENTS

| WO | WO 2011/047442 A1 | 4/2011 |
|---|---|---|
| WO | WO-2011047383 A1 | 4/2011 |
| WO | WO-2011109298 A2 | 9/2011 |
| WO | WO 2012/068098 A1 | 5/2012 |
| WO | WO-2013012747 A1 | 1/2013 |
| WO | WO 2013/044215 A1 | 3/2013 |
| WO | WO-2014012007 A2 | 1/2014 |

OTHER PUBLICATIONS

Dalerba, P., et al., "Phenotypic characterization of human colorectal cancer stem cells," Proc. Nat. Acad. Sci. 04(24):9913-10294, National Academy of Sciences, Washington, DC, USA (Jun. 2007).

Gallahan, D. et al., "A New Common Integration Region (int-3) for Mouse Mammary Tumor Virus on Mouse Chromosome 17," J. of Virol. 61(1):218-220, American Society for Microbiology, USA (Jan. 1987).

Gallahan, D. et al., "Expression of a Truncated Int3 Gene in Developing Secretory Mammary Epithelium Specifically Retards Lobular Differentiation Resulting in Tumorigenesis," Cancer Research 56:1775-1785, American Association for Cancer Research, USA (Apr. 1996).

Hallahan, A., et al., "The SmoA1 Mouse Model Reveals That Notch Signaling is Critical for the Growth and Survival of Sonic Hedgehog-Induced Medulloblastomas," Cancer Research 64(21):7794-7800, American Society for Cancer Research, USA (Nov. 2004).

International Search Report with Written Opinion for International Application No. PCT/US2010/58511, International Searching Authority, United States, mailed Mar. 3, 2011.

Leong, K. G. and Karsan, A., "Recent insights into the role of Notch signaling in tumorigenesis," Blood 107(6):2223-2233, The American Society of Hematology, USA (Mar. 2006).

Morrison, S.J. et al., "Transient Notch activation initiates an irreversible switch from neurogenesis to gliogenesis by neural crest stem cells," Cell 101(5):499-510, Cell Press, United States (2000).

Morrison, S.J., et al., "Hematopoietic stem cells: challenges to expectations," Curr. Op. Immun. 9:216-221, Current Biology, Ltd., England (1997).

Morrison, S.J., et al., "The Biology of Hematopoietic Stem Cells," Annu. Rev. Cell Dev. Biol. 11:35-71, Annual Reviews, USA (1995).

Seina, A., et al., "Biomarkers Predicting Clinical Outcome of Epidermal Growth Factor Receptor—Targeted Therapy in Metastatic Colorectal Cancer," JNCI 101(19): 1308-1324, Oxford University Press, England (Oct. 2009).

Nickoloff, B.J., et al., "Notch signaling as a therapeutic target in cancer: a new approach to the development of cell fate modifying agents," Oncogene 22(42):6598-6608, Nature Publishing Group, England (2003).

Rudikoff, S., et al., "Single amino acid substitution altering antigen-binding specificity," Proc. Natl. Acad. Sci. USA 79:1979-1983, National Academy of Sciences, United States (1982).

Colman, P.M., "Effects of amino acid sequence changes on antibody-antigen interactions," Res. Immunol. 145(1):33-36, Elsevier, France (1994).

Portolano, S., et al., Lack of promiscuity in autoantigen-specific H and L chain combinations as revealed by human H and L chain "roulette," J. Immunol. 150(3):880-887, American Association of Immunologists, United States (1993).

Skolnick, J. and Fetrow, J.S., "From genes to protein structure and function: novel applications of computational approaches in the genomic era," Trends Biotechnol. 18(1):34-39, Elsevier Science Publishers, England (2000).

Burgess, W.H., "Possible dissociation of the heparin-binding and mitogenic activities of heparin-binding (acidic fibroblast) growth factor-1 from its receptor-binding activities by site-directed mutagenesis of a single lysine residue," J. Cell Biol. 111(5 Pt 1):2129-2138, Rockefeller University Press, United States (1990).

Lazar, E., et al., "Transforming growth factor alpha: mutation of aspartic acid 47 and leucine 48 results in different biological activities," Mol. Cell Biol. 8(3): 1247-1252, American Society for Microbiology, United States (1988).

Barbas, III, C., et al., "In vitro evolution of a neutralizing human antibody to human immunodeficiency virus type 1 to enhance affinity and broaden strain cross-reactivity," Proc Nat. Acad Sci. USA 91:3809-3813, National Academy of Sciences, United States (1994).

Bloom, J., et al., "Intrachain disulfide bond in the core hinge region of human IgG4," Protein Science 6:407-415, Cambridge University Press, United States (1997).

Boerner, P., et al., "Production of Antigen-Specific Human Monoclonal Antibodies From In Vitro-Primed Human Splenocytes," J. Immunol. 147:86-95, The American Association of Immunologists, United States (1991).

Brennan, M., et al., "Preparation of Bispecific Antibodies by Chemical Recombination of Monoclonal Immunoglobin $G_1$ Fragments" Science 229:81-83, National Academy of Sciences, United States (1985).

Carter, P., et al., "Humanization of an anti-p185$^{HER2}$ antibody for human cancer therapy," Proc. Natl. Acad. Sci. USA 89:4285-4289, Academy of Sciences, United States (1992).

Chothia, C., et al., "Domain Association in Immunoglobin Molecules: The Packing of Variable Domains," J. Mol. Biol. 186:651-663, Academic Press, United Kingdom (1985).

Chothia, C. and Lesk, A., "Canonical Structures for the Hypervariable Regions of Immunoglobulins," J. Mol. Biol. 196:901-917, Academic Press Limited, United Stated (1987).

Chowdhury, P. and Pastan, I., "Improving antibody affinity by mimicking somatic hypermutation in vitro," Nat.Biotechnol. 17:568-572, Nature Publishing Co., United States (1999).

Cole, S., et al., "The EBV-Hybridoma Technique and Its Application to Human Lung Cancer," pp. 77-96, Monoclonal Antibodies and Cancer Therapy, Proceedings of the Roche—UCLA Symposium, Park City, Utah, USA, Alan R. Liss, Inc., Jan. 26-Feb. 2, 1985.

Deisenhofer, J., "Crystallagraphic Refinement and Atomic Models of a Human Fc Fragment and Its Complex with Fragment B of Protein A from Staphyloccocus aureus at 2.9 and 2.8—A Resolution," Biochemistry 20:2361-2370, the American Chemical Society, United States (1981).

Dreher, M., et al., "Colony assays for antibody fragments expressed in bacteria." J. Immunol. Methods 139:197-205, Elsevier Science Publishers B. V., Netherlands (1991).

Eppstein, D., et al , "Biological activity of liposome-encapsulated murine interferon γ is mediated by a cell membrane receptor," Proc. Natl. Acad Sci. USA 82:3688-3692, National Academy of Sciences, United States (1985).

Gruber, M., et al., "Efficient Tumor Cell Lysis Mediated by a Bispecific Single Chain Antibody Expressed in Escherichia coli," J. Immunol. 152:5368-5374, The American Association of Immunologists, United States (1994).

Harlowe, E. and Lane, D., eds., "Chapter 14: Immunoassays," in Antibodies: A Laboratory Manual, pp. 553-612, Cold Spring Harbor Laboratory, Cold Spring Harbor, NY (1988).

Harris, W., "Therapeutic Monoclonals," Biochem. Soc. Transactions 23:1035-1038, Industrial Biochemistry and Biotechnology Group Colloquium, University of Manchester, United Kingdom (1995).

Hawkins, R., et al., "Selection of Phage Antibodies by Binding Affinity Mimicking Affinity Maturation," J. Mol. Biol. 226:889-896, Academic Press Limited, United States (1992).

Hermentin, P. and Seiler, F., "Investigations with Monoclonals Antibody Drug (Anthracycline) Conjugates," Behring Inst. Mitt. 82:197-215, Die Medizinische Verlagsgesellschaft mbH, W. Germany (1988).

Hoogenboom, H. and Winter, G., "By-passing Immunisation: Human Antibodies from Synthetic Repertoires of Germline $V_H$ Gene Segments Rearranged in Vitro," J. Mol. Biol. 227:381-388, Academic Press Limited, United States (1992).

Humphreys, D., et al., "Formation of dimeric Fabs in Escherichia coli: effect of hinge size and isotype, presence of interchain disulphide bond, Fab' expression levels, tail piece sequences and growth conditions," J. Immunol. Methods 209:193-202, Elsevier Science B.V., Netherlands (1997).

Hurle, M. and Gross, M., "Protein engineering techniques for antibody humanization," Curr. Opin. Biotech. 5:428-433, Current Biology Ltd., United States (1994).

(56) References Cited

OTHER PUBLICATIONS

Hwang, K., et al., "Hepatic uptake and degradation of unilamellar sphingomyelin/cholesterol liposomes: A kinetic study," *Proc. Natl. Acad. Sci. USA* 77:4030-4034, National Academy of Sciences, United States (1980).

Jackson, J., et al., "In Vitro Antibody Maturation," *J. Immunol.* 154:3310-3319, The American Association of Immunologists, United States (1995).

Jones, P., et al., "Replacing the complementarity-determining regions in a human antibody with those from a mouse," *Nature* 321:522-525, Nature Publishing Group, United Kingdom (1986).

Kingsman, A., et al., "Replication In *Saccharomyces cerevisiae* of Plasmid pBR313 Carrying DNA From the Yeast *trpl* Region," *Gene* 7:141-152, Elsevier/North-Holland Biomedical Press, Netherlands (1979).

Kostelny, S., et al., "Formation of a Bispecific Antibody by the Use of Leucine Zippers," *J. Immunol.* 148:1547-1553, The American Association of Immunologists, United States (1992).

Lee, H., et al., "Generation of characterization of a novel single-gene-encoded single-chain immunoglobulin molecular with antigen binding activity and effector functions," *Mol. Immunol.* 36:61-71, Elsevier Science Ltd., Netherlands (1999).

Maeda, H., et al., "Construction of reshaped human antibodies with HIV-neutralizing activity," *Hum. Antibod. Hybridomas* 2:124-134, Butterworth-Heinemann, United Kingdom (1991).

Marks, J., et al., "By-passing Immunization: Human Antibodies from V-gene Libraries Displayed on Phage," *J. Mol. Biol.* 222:581-597, Academic Press Limited, United Kingdom (1991).

Marks, J., et al., "By-Passing Immunization: Building High Affinity Human Antibodies By Chain Shuffling," *Bio/Technology* 10:779-783, Nature Publishing Co., United States (1992).

Milstein, C., et al., "Hybrid hybridomas and their use in immunohistochemistry," *Nature* 305:537-539, Nature Publishing Group, United Kingdom (1983).

Morimoto, K., et al., "Single-step purification of F(ab')$_2$ fragments of mouse monoclonal antibodies (immunoglobulins G1) by hydrophobic interaction high performance liquid chromatography using TSKgel Phenyl-5PW," *J. Biochem. Biophys. Methods* 24:107-117, Elsevier Science Publishers B.V., Netherlands (1993).

Morrison, S., et al., "Chimeric human antibody molecules: Mouse antigen-binding domains with human constant region domains." *Proc. Natl. Acad. Sci. USA* 81:6851-6855, National Academy of Sciences, United States (1984).

Nohaile, M., et al., "Altering dimerization specificity by changes in surface electrostatics," *Proc. Natl. Acad. Sci. U.S.A.* 98:3109-3114, United States National Academy of Sciences, United States (2001).

Novotny, J. and Haber, E., "Structural invariants of antigen binding: Comparison of immunoglobin $V_L$-$V_H$ and $V_L$-$V_L$ domain dimers," *Proc. Natl. Acad. Sci. USA* 82:4592-4596, National Academy of Sciences, United States (1985).

Presta, L., et al., "Humanization of an Antibody Directed Against IgE," *J. Immunol.* 151:2623-2623, The American Association of Immunologists, United States (1993).

Riechmann, L., et al., "Reshaping human antibodies for therapy," *Nature* 332:323-329, Nature Publishing Group, United States (1988).

Sal-Man, N., et al., "Arginine mutations within a transmembrane domain of Tar, an *Escherichia coli* aspartate receptor, can drive homodimer dissociation and heterodimer association *in vivo*," *Biochem. J.* 385:29-36, Portland Press, United Kingdom (2005).

Schier, R., et al., "Identification of function and structural amino-acid residues by parsimonious mutagenesis," *Gene* 169:147-155, Elsevier Science B.V., Netherlands (1996).

Shalaby, M., et al., "Development of Humanized Bispecifics Antibodies Reactive with Cytotoxic Lymphocytes and Tumor Cells Overexpressing the *HER2* Protooncogene," *J. Exp. Med.*175:217-225, The Rockefeller University Press, United States (1992).

Sheets, M., et al., "Efficient construction of a large nonimmune phage antibody library: The production of high-affinity human single-chain antibodies to protein antigens," *Proc. Natl. Acad. Sci. USA* 95:6157-6162, National Academy of Sciences, United States (1998).

Sims, M., et al., "A Humanized CD18 Antibody Can Block Function without Cell Destruction," *J. Immunol.* 151:2296-2308, The American Association of Immunologists, United States (1993).

Stinchcomb, D., et al., "Isolation and characterisation of a yeast chromosomal replicator," *Nature* 282:39-43, Nature Publishing Group, United Kingdom (1979).

Suresh, M., et al., "Bispecific Monoclonal Antibodies from Hybrid Hybridomas," *Methods Enzymol.* 121:210-228, Academic Press Inc., United Kingdom (1986)

Traunecker, A., et al., "Bispecific single chain molecules (Janusins) target cytotoxic lymphocytes on HIV infected cells," *EMBO J*.10:3655-3659, Oxford University Press, United Kingdom (1991).

Tutt, A., et al., "Trispecific F(ab')$_3$ Derivatives That Use Cooperative Signaling Via the TCR/CD3 Complex and CD2 to Activate and Redirect Resting Cytotoxic T Cells," *J. Immunol.* 147:60-69, The American Association of Immunologists, United States (1991).

Urlaub, G. and Chasin, L., "Isolation of Chinese hamster cell mutants deficient in dihydrofolate reductase activity," *Proc. Natl. Acad. Sci. USA* 77: 4216-4220, National Academy of Sciences, United States (1980).

Vaswani, S. and Hamilton, R., "Humanized antibodies as potential therapeutic drugs," *Ann. Allergy Asthma Immunol.* 81:105-119, American College of Allergy, Asthma, & Immunology, United States (1998).

Vaughan, T., et al., "Human Antibodies with Sub-nanomolar Affinities Isolated from a Large Non-immunized Phage Display Library," *Nat. Biotech.*14:309-314, Nature Publishing Co., United States (1996)

Verhoeyen, M., et al., "Reshaping Human Antibodies: Grafting an Antilysozyme Activity," *Science* 239:1534-1536, American Association for the Advancement of Science, United States (1988).

Ward, E., "Antibody Engineering Using *Escherichia coli* as Host," *Adv. Pharmacol.* 24:1-20, Academic Press, Inc., United Kingdom (1993).

Wu, C., et al., "Simultaneous targeting of multiple disease mediators by a dual-variable-domain immunoglobulin," *Nat. Biotech.* 25:1290-1297, Nature Publishing Co., United States (2007).

Yelton, D., et al., "Affinity Maturation of the BR96 Anti-Carcinoma Antibody by Codon-Based Mutagenesis," *J. Immunol.* 155:1994-2004, The American Association of Immunologists, United States (1995).

International Search Report with the Written Opinion of the International Searching Authority for International application No. PCT/US10/32625, mailed on Dec. 17, 2010, United States Patent and Trademark Office, United States.

International Serch Report with the Written Opinion of the International Searching Authority for International application No. PCT/US12/56886, mailed Feb. 28, 2013, United States Patent and Trademark Office, United States.

International Search Report of the International Searching Authority for International application No. PCT/US2007/020889, mailed Apr. 9, 2008, United States Patent and Trademark Office, United States.

Written Opinion of the International Searching Authority for International application No. PCT/US2007/020889, mailed Apr. 9, 2008, United States Patent and Trademark Office, United States.

Dixit, R., "Cardiovascular Safety of Biologics: Challenges and Opportunities," Medimmne, Safety Pharacology Society, Annular Meeting Speakers Presentations (Oct. 2, 2012).

Yen, W.C., et al., "Anti-DLL4 Has Broad Spectrum Activity in Pancreatic Cancer Dependent on Targeting DLL4-Notch Signaling in Both Tumor and Vascularture Cells," *Clin Cancer Res* 18(19):5374-5386, American Association for Cancer Research, United States (2012).

Beachy, P., et al., "Tissue repair and stem cell renewal in carcinogenosis," *Nature* 432:324-331, Nature Publishing Group, New York, NY, U.S.A. (2004).

Bellavia, D., et al., "Constitutive activation of NF-κB and T-cell leukemia/lymphoma in Notch3 transgenic mice," *EMBO J.* 19:3337-3348, Oxford University Press, New York, NY U.S.A. (2000).

Bonnet, D. and Dick, J.E., "Human acute myeloid leukemia is organized as a hierarchy that originates from a primitive hematopoietic cell," *Nat. Med.* 3:730-737, Nature Publishing Group, New York, NY, U.S.A. (1997).

(56) References Cited

OTHER PUBLICATIONS

Brennan, K. and Brown, A.M.C.,"Is there a role for Notch signalling in human breast cancer?" *Breast Cancer Res.* 5:69-75, BioMed Central Ltd, London, UK (2003).
Ellisen, L. W., et al., "TAN-1, the Human Homolog of the *Drosophilia* Notch Gene, Is Broken by Chromosomal Translocations in T Lymphoblastic Neoplasms," *Cell* 66:649-661, Elsevier Inc., Amsterdam, The Netherlands (1991).
Hope, K.J., et al., "Acute myeloid leukemia originates from a hierarchy of leukemic stem cell classes that differ in self-renewal capacity," *Nat. Immunol.* 5:738-43, Nature Publishing Group, New York, NY, U.S.A. (2004).
Iso, T., et al., "Notch Signaling in Vascular Development," *Arterioscler. Thromb. Vasc. Biol.* 23:543-553, Lippincott Williams & Wilkins, Philadelphia, PA, U.S.A. (2003).
Jhappan, C., et al., "Expression of an activated *Notch*- related *int*-3 transgene interferes with cell differentiation and includes neoplastic and salviary glands," *Genes & Dev.* 6:345-355, Cold Spring Harbor Laboratory Press, Woodbury NY, U.S.A. (1992).
Kopper, L. and Hajdú, M., "Tumor Stem Cells," *Pathol. Oncol. Res.* 10:69-73, Arányi Lajos Foundation, Budapest, Hungary (2004).
Krebs, L.T., et al., "Notch signaling is essential for vascular morphogenesis in mice," *Genes & Dev.* 14:1343-1352, Cold Spring Harbor Laboratory Press, Woodbury NY, U.S.A. (2008).
Lapidot, T., et al., "A cell initiating human acute myeloid leukaemia after transplantation into SCID mice," *Nature* 367:645-648, Nature Publishing Group, New York, NY, U.S.A. (1994).
Leethanakul, C., et al., "Distinct pattern of expression of differentiation and growth-related genes in squamous cell carcinomas of the head and neck revealed by the use of laser capture microdissection and cDNA arrays," *Oncogene* 19:3220-3224, Nature Publishing Group, New York, NY, U.S.A. (2000).
Morrison, S.J., et al., "Regulatory Mechanisms in Stem Cell Biology," *Cell* 88:287-298, Cell Press, St. Louis, MO, U.S.A. (1997).
Noguera-Troise, I., et al., "Blockade of Dll4 inhibits tumour growth by promoting non-productive angiogenesis," *Nature* 444:1032-1037, Nature Publishing Group, New York, NY, U.S.A. (2006).
Parr, C., et al., "The possible correlation of Notch-1 and and Notch-2 with clinical outcome and tumour clinicopathological parameters in human breast cancer," *Int. J. Mol. Med.* 14:779-786, Spandidos Publications Ltd., Athens, Greece (2004).
Pear, W.S., et al., "Exclusive Development of T cell Neoplasms in Mice Transplanted with Bone Marrow Expressing Activated *Notch* Alleles," *J Exp. Med.* 183:2283-2291, the Rockefeller University Press, New York, NY, U.S.A. (1996).
Pear, W.S. and Aster, J.C., "T cell acute lymphoblastic leukemia/lymphoma: a human cancer commonly associated with aberrant NOTCH1 signaling," *Curr. Opin. Hematol.* 11:426-433, Lippincott Williams & Wilkins, Philadelphia, PA, U.S.A. (2004).
Politi, K., et al., "Notch in mammary gland development and breast cancer," *Semin. Cancer Biol.* 14:341-347, Elsevier Inc., Amsterdam, The Netherlands (2004).
Purow, B.W., et al., "Expression of Notch-1 and Its Ligands, Delta-Like-1 and Jagged-1, Is Critical for Glioma Cell Survival and Proliferation," *Cancer Res.* 65:2353-2363, BioMed Central Ltd, London, UK (2005).
Rae, F.K., et al., "Novel Association of a Diverse Range of Genes with Renal Cell Carcinoma as Identified by Differential Display," *Int. J. Cancer* 88:726-732, Wiley-Liss, Inc., Massachusetts, U.S.A (2000).
Ridgeway., J., et al., "Inhibition of Dll4 signaling inhibits tumour growth by deregulating angiogenesis," *Nature* 444:1083-1087, Nature Publishing Group, New York, NY, U.S.A. (2006).
Robey, E., et al., "An Activated Form of Notch Influences the Choice between CD4 and CD8 T Cell Lineages," *Cell* 87:483-492, Elsevier Inc., Amsterdam, The Netherlands (1996).
Shutter, J.R., et al., "*Dll4*, a novel Notch ligand expressed in arterial endothelium," *Genes & Dev.* 14:1313-1318, Cold Spring Harbor Laboratory Press, Woodbury NY, U.S.A. (2000).

Smith, G.H., et al., "Constitutive Expression of a Truncated *INT3* Gene in Mouse Mammary Epithelium Impairs Differentiation and Functional Development," *Cell Growth Differ.* 6:563-577, the American Association for Cancer Research, Philadelphia, PA, U.S.A. (1995).
Soriano, J.V., et al., "Expression of an Activated Notch4(int-3) Oncoprotein Disrupts Morphogenesis and Induces an Invasive Phenotype in Mammary Epithelial Cells In Vitro," *Int. J. Cancer* 86:652-659, Wiley-Liss, Inc., Massachusetts, U.S.A (2000).
Suzuki, T., et al., "Imbalanced expression of *TAN-1* and human *Notch4* in endometrial cancers," *Int. J. Oncol.* 17:1131-1139, Spandidos Publications Ltd., Athens, Greece (2000).
Thurston, G., et al., "The Delta paradox:DLL4 blockade leads to more tumour vessels but less growth," *Nature Reviews Cancer* 7:327-331, Nature Publishing Group, New York, NY, U.S.A. (2007).
Uyttendaele, H., et al., "Notch4 and Wnt-1 Proteins Function to Regulate Branching Morphogenesis of Mammary Epithelial Cells in an Opposing Fashion," *Dev. Biol.* 196:204-217, Elsevier Inc., Amsterdam, The Netherlands (1998).
Van ES, J.H., and Clevers, H., "Notch and Wnt inhibitors as potential new drugs for intestinal neoplastic disease," *Trends Mol. Med.* 11:496-502, Elsevier Inc., Amsterdam, The Netherlands (2005).
Van Limpt, V., et al., "SAGE Analysis of Neuroblastoma Reveals a High Expression of the Human Homologue of the *Drosophila Delta* Gene," *Med. Pediatr. Oncol.* 35:554-558, Wiley-Liss, Inc., Massachusetts, U.S.A (2000).
Weijzen, S., et al., "Activation of Notch-1 signaling maintains the neoplastic phenotype in human Ras-transformed cells," *Nat. Med.* 8:979-986, Nature Publishing Group, New York, NY, U.S.A. (2002).
Yan, X.-Q., et al. "A novel Notch ligand, *Dll4*, induces T-cell leukemia/lymphoma when overexpressed in mice retroviral-mediated gene transfer," *Blood* 98:3793-3799, Washington, DC, U.S.A. (2001).
Zagouras, P., et al., "Alterations in Notch signaling in neoplastic lesions of the human cervix," *PNAS* 92:6414-6418, the National Academy of Sciences, Washington DC, U.S.A. (1995).
Fleming, R.J. et al., "The Notch receptor and its ligands," *Trends in Cell Biol.* 7:437-441 (1997).
Dorsch, M., et al., "Ectopic expression of Delta4 impairs hematopoietic development and leads to lymphoproliferative disease," *Blood* 100:2046-2055 (2002).
Dando, J. et al., "Notch/Delta4 Interaction in Human Embryonic Liver $CD34^+CD38^-$ Cells: Positive Influence on BGU-E Production in LTC-IC Potential Maintenance," *Stem Cells* 23:550-560 (2005).
Williams, C.K., et al., "Up-regulation of the Notch ligand Delta-like 4 inhibits VEGF-induced endothelial cell function," *Blood* 107:931-939 (Feb. 2006).
Lauret, E. et al., "Membrane-bound Delta-4 Notch ligand reduces the proliferative activity of primitive human hematopoietic $CD34^{30}$ $CD38^{low}$ cells while maintaining their LTC-IC potential," *Leukemia* 18:788-797 (Feb. 2006).
Sugimoto, A. et al., "Delta-4 Notch ligand promotes erythroid differentiation of human umbilical cord blood CD34+ cells," *Exp. Hematol.* 34:424-432 (Apr. 2006).
Liu, Z-J., et al., "Inhibition of endothelial cell proliferation by Notch 1 signaling is mediated by repressing MAPK and P14K/Akt pathways and requires MAML1," *FASEB J.* 20:E201-E210 (May 2006).
Hainaud, P., et al., "The Role of the Vascular Endothelial Growth Factor-Delta-like 4 ligand/Notch4-Ephrin B2 Cascade in Tumor Vessel Remodeling and Endothelial Cell Functions," *Cancer Res.* 66:8501-8510 (Sep. 2006).
Duarte, A., et al., "Dosage-sensitive requirement for mouse Dll4 in artery development," *Genes Dev.* 18:2474-2478, Cold Spring Harbor, NY U.S.A. (2004).
Fung, E., et al., "Delta-like 4 induces notch signaling in macrophages: implications, for inflammation," *Circulation* 115:2948-2956, Lippincott Williams & Wilkins, Baltimore, MD U.S.A. (2007).
Gale, N.W., et al., "Haploinsufficiency of delta-like 4 ligand results in embryonic lethality due to major defects in arterial and vascular development," *Proc. Natl. Acad. Sci. USA* 101:15949-15954, National Academy of Sciences (2004).
Garber, K., "Notch Emerges as New Cancer Drug Target," *JNCI* 99:1284-1285, Oxford University Press (2007).

(56) References Cited

OTHER PUBLICATIONS

Gridley, T., "Notch signaling in vascular development and physiology," *Development* 134:2709-2718, The Company of Biologists (2007).
Harrington, L.S., et al., "Regulation of multiple angiogenic pathways by Dll4 and Notch in human umbilical vein endothelial cells," *Microvasc. Res.* 75:144-154, Elsevier, Inc. (2008).
Hellström, M., et al., "Dll4 signalling through Notch1 regulates formation of tip cells during angiogenesis," *Nature* 445:776-780, Nature Publishing Group (2007).
Henning, K., et al., "mNotch1 signaling and erythropoietin cooperate in erythroid differentiation of multipotent progenitor cells and upregulate β-*globin*," *Exp. Hematol.* 35:1321-1332, Elsevier, Inc. (2007).
Ishiko, E., et al., "Notch Signals Inhibit the Development of Erythroid/Megakaryocytic Cells by Suppressing GATA-1 Activity through Induction of HES1," *J. Biol. Chem.* 280:4929-4939, The American Society for Biochemistry and Molecular Biology, Inc. (2005).
Jarriault, S., et al., "Signalling downstream of activated mammalian Notch," *Nature* 377:355-358, Nature Publishing Group (1995).
Krebs, L.T., et al., "Haploinsufficient lethality and formation of arteriovenous malformations in Notch pathway mutants," *Genes Dev.* 18:2469-2473, Cold Spring Harbor Laboratory Press (2004).
Mailhos, C., et al., "Delta4, an endothelial specific Notch ligand expressed at sites of physiological and tumor angiogenesis," *Differentiation* 69:135-144, Blackwell Wissenschafts-Verlag (2001).
Mazella, J., et al., "Expression of Delta-Like Protein 4 in the Human Endometrium," *Endocrinology* 149:15-19, The Endocrine Society (2008).
Parks, A.I., et al., "Structure-Function Analysis of Delta Trafficking, Receptor Binding and Signaling in *Drosophila*," *Genetics* 174:1947-1961, The Genetics Society of America (2006).
Patel, N.S., et al., "Up-regulation of Delta-like 4 Ligand in Human Tumor Vasculature and the Role of Basal Expression in Endothelial Cell Function," *Cancer Res.* 65:8690-8697, The American Association for Cancer Research (2005).
Rao, P.K., et al., "Isolation and Characterization of the Notch Ligand Delta4," *Cell Res.* 260:379-386, Elsevier, Inc. (2008).
Scehnet, J.S., et al., "Inhibition of Dll4-mediated signaling induces proliferation of immature vessels and results in poor tissue perfusion," *Blood* 109:4753-4760, American Society of Hematlogy (2007).
Wilson, A., and Radtke, F., "Multiple functions of Notch signaling in self-renewing organs and cancer," *FEBS Lett.* 580:2860-2868, Elsevier, Inc. (2006).
Besseyrias, V., et al., "Hierarchy of Notch-Delta interactions promoting T cell lineage commitment and maturation," *J. Exp. Med.* 204:331-343, The Rockefeller University Press (2007).
Engin, F., et al., "Dimorphic effects of Notch signaling in bone homeostasis," *Nature Medicine* 14:299-305, Nature Publishing Group (2007).
Siekmann, A.F. and Lawson, N.D., "Notch signalling limits angiogenic cell behaviour in developing zebrafish arteries," *Nature* 445:781-784, Nature Publishing Group (2007).
Phng, L.-K., et al., "Nrarp Coordinates Endothelial Notch and Wnt Signaling to Control Vessel Density in Angiogenesis," *Dev. Cell* 16:70-82, Elsevier, Inc. (2009).
Sainson, R.C.A. and Harris, A.L., "Anti-Dll4 therapy: can we block tumour growth by increasing angiogenesis?," *Trends Mol. Med.* 13:389-395, Elsevier, Inc. (2007).
Hoey, T., et al., "DLL4 Blockade Inhibits Tumor Growth and Reduces Tumor Initiating Cell Frequency," *Cell Stem Cell* (in press).
Li, J.-L. and Harris, A.L., "Notch signaling from tumor cells: A new mechanism of angiogenesis," *Cancer Cell* 8:1-3, Cell Press (2005).
Shawber, C.J., et al., "Notch Signaling in Primary Endothelial Cells," *Ann. N.Y. Acad. Sci.* 995:162-170, New York Academy of Sciences (2003).
Bray, S.J., "Notch signalling: a simple pathway becomes complex," *Nature* 7:678-689, Nature Publishing Group (2006).

Dorsch, M., et al., "Ectopic expression of Delta4 impairs hematopoietic development and leads to lymphoproliferative disease," *Blood* 100:2046-2055, American Society of Hematology (2002).
Farnie, G., et al., "Novel Cell Culture Technique for Primary Ductal Carcinoma In Situ: Role of Notch and Epidermal Growth Factor Receptor Signaling Pathways," *JNCI* 99:616-627, Oxford University Press (2007).
Gale, N.W., et al., "Haploinsufficiency of delta-like 4 ligand results in embryonic lethality due to major defects in arterial and vascular development," *PNAS* 101:15949-15954, National Academy of Sciences (2004).
Liu, Z.-J., et al., "Regulation of *Notch1* and *Dll4* by Vascular Endothelial Growth Factor in Arterial Endothelial Cells: Implications for Modulating Arteriogenesis and Angiogenesis," *Molecular and Cellular Biology* 23:14-25, America Society for Microbiology (2003).
Liu, S., et al., "Mammary stem cells, self-renewal pathways, and carcinogenesis," *Breast Cancer Research* 7:86-95, BioMed Central Ltd. (2005).
Dontu, G., et al., "Role of Notch signaling in cell-fate determination of human mammary stem/progenitor cells," *Breast Cancer Res.* 6:R605-R615, BioMed Central Ltd. (2004).
Farnie, G. and Clarke, R.B., "Mammary Stem Cells and Breast Cancer—Role of Notch Signalling," *Stem Cell Rev.* 3:169-175, Humana Press (2007).
Miele, L. and Osborne, B., "Arbiter of Differentiation and Death: Notch Signaling Meets Apoptosis," *Journal of Cellular Physiology* 181:393-409, Wiley-Liss, Inc. (1999).
Duarte, A., et al., Dosage-sensitive requirement for mouse Dll4 in artery development, *Genes & Dev.* 18:2474-2478, Cold Spring Harbor Laboratory Press (2004).
Miele, L., "Notch Signaling," *Clin. Cancer Res.* 12:1074-1077, American Association for Cancer Research (2006).
Hofmann, J.J. and Iruela-Arispe, M.L., "Notch Signaling in Blood Vessels: Who Is Talking to Whom About What?," *Circ. Res.* 100:1556-1568 American Heart Association, Inc. (2007).
Limbourg, A., et al., Notch Ligand Delta-Like 1 Is Essential for Postnatal Arteriogenesis, *Circ. Res.* 100:363-371, American Heart Association, Inc. (2007).
Lobov, I.B., et al., Delta-like ligand 4 (Dll4) is induced by VEGF as a negative regulator of angiogenic sprouting, *PNAS* 104:3219-3224, National Academy of Sciences (2007).
Clarke, M.F., et al., "Cancer Stem Cells-Perspectives on Current Status and Future Directions: AACR Workshop on Cancer Stem Cells," *Cancer Res.* 66:9339-9344, American Association for Cancer Research (2006).
Milano, J., et al., Modulation of Notch Processing by γ-Secretase Inhibitors Causes Intestinal Goblet Cell Metaplasia and Induction of Genes Known to Specify Gut Secretory Lineage Differentiation, *Toxicol Sci* 82:341-358, Society of Toxicology (2004).
Reya, T., et al., "Stem cells, cancer, and cancer stem cells," *Nature* 414:105-111, Nature Publishing Company (2001).
Tax, F.E., et al., "Sequence of *C. elegans lag*-2 reveals a cell-signalling domain shared with *Delta* and *Serrate* of *Drosophila*," *Nature* 368:150-154, Nature Publishing Company (1994).
Wang, J.C.Y., et al., "Primitive Human Hematopoeitic Cells Are Enriched in Cord Blood Compared with Adult Bone Marrow or Mobilized Peripheral Blood as Measured by the Quantitative In Vivo SCID-Repopulating Cell Assay," *Blood* 89:3919-3924, The American Society of Hematology (1997).
Weng, A.P., et al., "Activating Mutations of *NOTCH1* in Human T Cell Acute Lymphoblastic Leukemia," *Science* 306:269-371, American Association for the Advancement of Science (2004).
Yen, W.-C., et al., "Targeting Cancer Stem Cells and Vasculature by a Novel Anti-Dll4 Antibody Inhibits Pancreatic Tumor Growth and Delays Tumor Recurrence," presented at the 100th Annual Meeting of the American Association for Cancer Research in Denver, Colorado, on Apr. 18-22, 2009, 1 page.
Office Action mailed Dec. 26, 2008 in U.S. Appl. No. 11/607,780, inventors Clarke, et al., filed Dec. 1, 2006.
Office Action mailed Jan. 2, 2009 in U.S. Appl. No. 11/607,780, inventors Clarke, et al., filed Dec. 1, 2006.

(56) References Cited

OTHER PUBLICATIONS

Response to Office Action mailed Jan. 2, 2009, sent electronically on Jul. 2, 2009, in U.S. Appl. No. 11/607,780, inventors Clarke, et al., filed Dec. 1, 2006.
Allenspach, E.J. et al., "Notch signaling in cancer," *Cancer Biol Ther.* 1(5):466-76, Landes Bioscience, United States (2002).
Artavanis-Tsakonas, S. et al., "Notch signaling: cell fate control and signal integration in development," *Science* 284(5415):770-6, American Association for the Advancement of Science, United States (1999).
Axelson, H., "Notch signaling and cancer: emerging complexity," *Semin Cancer Biol.* 14(5):317-9, Academic Press, England (2004).
Callahan, R. and Raafat, A., "Notch signaling in mammary gland tumorigenesis," *J Mammary Gland Biol Neoplasia* 6(1):23-36, Kluwer Academic/Plenum Publishers, United States (2001).
U.S. Appl. No. 12/497,405, inventors Yan et al., filed Jul. 2, 2009 (Not Published).
Fre, S. et al., "Notch signals control the fate of immature progenitor cells in the intestine," *Nature* 435(7044):964-8, Nature Publishing Group, England (2005).
Han, W. et al., "A soluble form of human Delta-like-1 inhibits differentiation of hematopoietic progenitor cells," *Blood* 95(5):1616-25, American Society of Hematology, United States (2000).
Harper, J.A. et al., "Notch signaling in development and disease," *Clin Genet.* 64(6):461-72, Munksgaard, Denmark (2003).
Hopfer, O. et al., "The Notch pathway in ovarian carcinomas and adenomas," *Br J Cancer* 93(6):709-18, Nature Publishing Group on behalf of Cancer Research UK, England (2005).
Janeway, C. et al., "Immunobiology: The Immune System in Health and Disease," Appendix L, pp. 579-581, Current Biology Publications, 4th Edition (1999).
Jeffries, S. and Capobianco, A.J., "Neoplastic transformation by Notch requires nuclear localization," *Mol Cell Biol.* 20(11):3928-41, American Society for Microbiology, United States (2000).
Nam, Y. et al., "Notch signaling as a therapeutic target," *Curr Opin Chem Biol.* 6(4):501-9. Elsevier, England (2002).
Tannock, I. and Hill, R., "The Basic Science of Oncology," pp. 357-358, New York: McGraw-Hill (1998).
Thélu, J. et al., "Notch signalling is linked to epidermal cell differentiation level in basal cell carcinoma, psoriasis and wound healing," *BMC Dermatol.* 2(1):7, BioMed Central, England (2002).
Weng, A.P. et al., "Growth suppression of pre-T acute lymphoblastic leukemia cells by inhibition of notch signaling," *Mol Cell Biol.* 23(2):655-64, American Society for Microbiology, United States (2003).
Carter, P., "Improving the efficacy of antibody-based cancer therapies," *Nat. Rev. Cancer.* 1(2): 118-29, Nature Pub. Group, England (Nov. 2001).
Noguera, I., et al.,"Expression of Delta-like 4 (Dll4) ligand in mouse tumor models" *Proceedings of the Annual Meeting of the American Association for Cancer Research* 46(*Suppl. S*): 1104, American Association for Cancer Research, United States (Apr. 2005).
Noguera, I., et al., "Delta-like ligand 4 (Dll4) is critical for tumor growth and angiogenesis" *Proceedings of the Annual Meeting of the American Association for Cancer Research* 47: 1342, American Association for Cancer Research, United States (Apr. 2006).
Xu, A., et al., "Regions of *Drosophila* Notch that contribute to ligand binding and the modulatory influence of Fringe," *J. Biol. Chem.* 280(34): 30158-65, American Society for Biochemistry and Molecular Biology, United States (Aug. 2005; Epub: Jun. 2005).
Supplementary European Search Report issued in the corresponding European Patent Application No. 07 83 8966, European Patent Office, Munich, Germany, mailed on Apr. 6, 2010.
Paul, William E., *Fundamental Immunology*, 3rd Edition, Chapter 8, p. 242, Raven Press, New York, United States, (1993).
Gurney, A. and Hoey, T., "Anti-DLL4, a cancer therapeutic with multiple mechanisms of action," *Vasc. Cell* 3:18, BioMed Central, England (2011), 4 pages.
Smith et al., "A First-in-Human, Phase 1 Trial of the Anti-DLL4 Antibody (OMP-21M18) Tageting Cancer Stem CellS (CSCs) in Patients with Advanced Solid Tumors," http://www.oncomed.com/news/pr/study1posterfinalNov10.pdf, accessed Feb. 2, 2012, 1 page.
Yan, M., et al., "Chronic DLL4 blockade induces vascular neoplasms," *Nature* 463:E6-E7, Macmillan Publishers Limited, England (2010).
NCT00744562, "A Phase 1 Dose Escalation Study of OMP-21M18 in Subjects With Solid Tumors," ClinicalTrials.gov archive, accessed at http://clinicaltrials.gov/archive/NCT01189968/2010_10_28, accessed on Feb. 2, 2012, 4 pages.
NCT01189968, "A Phase 1b Study of Carboplatin and Permetrexed Plus OMP-21M18 as 1st-line Treatment in Subject With Non-Squamous Non-Small Cell Lung Cancer," ClinicalTrials.gov archive, accessed at http://clinicaltrials.gov/archive/NCT01189968/2010_10_28, accessed on Feb. 7, 2012, 4 pages.
International Search Report for International Patent Application No. PCT/US11/60773, International Searching Authority, Alexandria, Virginia, United States, mailed on Mar. 26, 2012.
Written Opinion of the International Searching Authority for International Patent Application No. PCT/US11/60773, International Searching Authority, Alexandria, Virginia, United States, mailed Mar. 26, 2012.
Oishi, H., et al., "Novel therapeutic strategy for pancreatic cancer targeting Notch signaling pathway," *Proceedings of the Japanese Cancer Association* 65:311-312, Japan (2006).
Unknown Author, "Tumor angiogenesis suppression therapy targeting the Notch signaling pathway," *Suizo* (*Pancreas*) 21(3):249, Japan (2006).
English language translation of Oishi, H., et al., "Novel therapeutic strategy for pancreatic cancer targeting Notch signaling pathway," *Proceedings of the Japanese Cancer Association* 65:311-312, Japan (2006).
English language translation of "Tumor Angiogenesis suppression therapy targeting the Notch signaling pathway," *Suizo* (*Pancreas*) 21(3):249, Japan (2006).
Co-pending U.S. Appl. No. 14/498,602, filed Sep. 26, 2014.
Dalerba, P., et al., "Phenotypic characterization of human colorectal cancer stem cells," Proceedings of the National Academy of Sciences of the United States of America 104(24):9913-10294, National Academy of Sciences, United States (2007).
Gridley, T., "Notch Signaling During Vascular Development," Proceedings of the National Academy of Sciences 98(10):5377-5378, National Academy of Sciences, United States (2001).
Merchant, A.M., et al., "An efficient route to human bispecific IgG," Nature Biotechnology 16(7):677-681, Nature Publishing Group, United States (1998).
Morimoto, K., et al., "Single-step purification of F(ab)2 fragments of mouse monoclonal antibodies (immunoglobulins G1) by hydrophobic interaction high performance liquid chromatography using TSKgel Phenyl-5PW," Journal of Biochemical and Biophysical Methods 24:107-117, Elsevier Science Publishers B.V., Netherlands (1993).
Office Action mailed Mar. 22, 2013 in U.S. Appl. No. 12/782,429, Gurney, et al., filed May 18, 2010.
Office Action mailed Oct. 24, 2013 in U.S. Appl. No. 12/782,429, Gurney, et al., filed May 18, 2010.
Office Action mailed Sep. 11, 2014 in U.S. Appl. No. 12/782,429, Gurney, et al., filed May 18, 2010.
Holash, J., et al., "VEGF-Trap: A VEGF blocker with potent antitumor effects," Proceedings of the National Academy of Sciences 99:11393-11398, National Academy of Sciences, United States (2002).
Amado, R.G., et al., "Wild-Type KRAS is Required for Panitumumab Efficacy in Patients with Metastatic Colorectal Cancer,"Journal of Clinical Oncology 26(10):1626-1634, American Society of Clinical Oncology, United States (2008).
Beviglia, L., et al., "Anti-DLL4 reduces tumor growth and tumorigenicity in B-RAF V600E melanomas including those with acquired resistance to B-RAF inhibitors," AACR 103rd Annual Meeting 2012, Mar. 31-Apr. 4, Abstract LB-196, 1 page (2012).
Beviglia, L., et al., "In vivo evaluation of anti-tumor activity by an anti-VEGF and anti-DLL4 bispecific antibody in a humanized model of skin graft," AACR 104th Annual Meeting 2013, Abstract 4330, Apr. 6-10, 1 page (2013).

(56) References Cited

OTHER PUBLICATIONS

Bienz, M. and Clevers, H., "Linking Colorectal Cancer to Wnt Signaling," Cell 103(2),311-320 Cell Press, United States (2000).

Boyden, L.M., et al., "High Bone Density Due to a Mutation in LDL-Receptor-Related Protein 5," The New England Journal of Medicine 346(20):1513-1521, Massachusetts Medical Society, United States (2002).

Chen, J.Z., et al., et al., "Cloning and Identification of a cDNA that encodes a Novel Human Protein with Thrombospondin Type I Repeat Domain, hPWTSR," Molecular Biology Reports 29:287-292, Kluwer Academic Publisers, Netherlands (2002).

Chi, A.S., et al., "Angiogenesis as a Therapeutic Target in Malignant Gliomas," Oncologist 14(6):621-636, AlphaMed Press, United States (2009).

Claxton, S. and Fruttiger, M., "Periodic Delta-like 4 expression in developing retinal arteries," Gene Expression Pattern 5:123-127, Elsevier B.V., Netherlands (2004).

Cubillo, A., et al., "A Phase 1b study of demcizumab (DEM, anti-DLL4) with gemcitabine (GEM) in patients with first line locally advanced or metastatic pancreatic cancer," Proceedings of the AACR-NCI-EORTC International Conference on Molecular Targets and Cancer Therapeutics, Oct. 19-23, 2013, Abstract B78, 2 pages (2013).

Deonarain, M.P., et al., "Antibodies Targeting Cancer Stem Cells: A New Paradigm in Immunotherapy?," mAbs 1(1):12-25,Taylor & Francis, United States (2009).

Dupont, J. "Anti-Angiogenic Agents and Cardiovascular Effects: Implications for Clinical Development in Cancer," presentation given in Barcelona, Spain on Nov. 4, 2011, 16 pages.

Easwaran, V., et al., "Beta-Catenin Regulates Endothelial Growth Factor Expression in Colon Cancer," Cancer Research 63(12):3145-3153, American Association for Cancer Research, United States (2003).

European Opposition Brief for European Patent No. 2157192 filed May 8, 2014, 46 pages.

European Search Report for EP Application No. EP10824244.7, Munich, Germany, mailed on Feb. 18, 2013, 6 pages.

Fischer, L., et al., "Wnt-3A Enhances Bone Morphogenetic Protein-2-Mediated Chondrogenesis of Murine C3H10T1/2 Mesenchymal Cells," The Journal of Biological Chemistry 277(34):30870-30878, JBC Papers in Press, American Society for Biochemistry and Molecular Biology, United States (2002).

Fischer, M., et al., "Anti-DLL4 Inhibits Growth and Reduces Tumor-Initiating Cell Frequency in Colorectal Tumors with Oncogenic KRAS Mutations," Cancer Research 71(5):1520-1525, American Association for Cancer Research, United States (2001).

Fujino, T., et al., "Low-Density Lipoprotein Receptor-Related Protein 5 (LRP5) is Essential for Normal Cholesterol Metabolism and Glucose-Induced Insulin Secretion," Proceedings of the National Academy of Sciences 100(1):229-234, National Academy of Sciences, United States (2003).

Gagnon, M.L., et al., "Identification of a natural soluble neuropilin-1 that binds vascular endothelial growth factor: In vivo expression and antitumor activity," Proceedings of the National Academy of Sciences 97(6):2573-2578, National Academy of Sciences, United States (2000).

Goldblum, S.E., et al., "Thrombospondin-1 Induces Tyrosine Phosphorylation of Adherens Junction Proteins and Regulates an Endothelial Paracellular Pathway," Molecular Biology of the Cell 10(5):1537-1551, The American Society for Cell Biology, United States (1999).

Gong, Y., et al., "LDL Receptor-Related Protein 5 (LRP5) Affects Bone Accrual and Eye Development," Cell 107 (4):513-523, Cell Press, United States (2001).

Gracian, A.C., et al., "A phase 1b study of the anticancer stem cell agent demcizumab (DEM) and gemcitabine (GEM) with or without paclitaxal protein bound particles (nab-paclitaxel) in patients with pancreatic cancer," 2014 Gastrointestinal Cancers Symposium, Abstract 279, 2 pages (2014).

Gronberg, B.H., et al., "Phase III Study by the Norwegian Lung Cancer Study Group: Chemotherapy in Advanced Non-small-cell Lung Cancer," Journal of Clinical Oncology 27(19):3217-3224, American Society of Clinical Oncology, United States (2009).

Hartmann, C., "Wnt-Signaling and Skeletogenesis," Journal of Musculoskelet & Neuronal Interactions 2(3):274-276, International Society of Musculoskeletal and Neuronal Interactions, Greece (2002).

Hidalgo, M., et al., "A Phase 1b Study of the Anti-Cancer Stem Cell Agent Demcizumab (DEM, anti-DLL4) and Gemcitabine (GEM) with or without Nab-Paclitaxvel in Patients with Pancreatic Cancer," European Society for Medical Oncology 2014 Congress, Sep. 17 and Sep. 28, Poster 616PD, 1 page (2014).

Holash, J., et al., "Inhibitors of growth factor receptors, signaling pathways and angiogenesis as therapeutic molecular agents," Cancer Metastasis Rev 25:243-252, Dordrecht, Netherlands (2006).

Horesh, Y., et al., "A Rapid Method for Detection of Putative RNAi Target Genes in Genomic Data," Bioinformatics 19(Suppl 2):ii73-ii80, Oxford University Press, England (2003).

International Preliminary Report on Patentability and Written Opinion for International Application No. PCT/US2010/53064, International Searching Authority, mailed on Feb. 14, 2011, 7 pages.

International Preliminary Report on Patentability for International Application No. PCT/US2013/065015, The International Bureau of WIPO, Switzerland, mailed on Apr. 22, 2014, 17 pages.

International Search Report for International Application No. PCT/US2010/53064, mailed on Feb. 14, 2011, 3 Pages.

Izzedine, H., et al., "Management of Hypertension in Angiogenesis Inhibitor-Treated Patients," Annals of Oncology 20(5):807-815, Oxford University Press, England (2009).

Jackson, A.L. and Linsley, P.S., "Noise Amidst The Silence: Off-Target Effects of siRNAs?," Trends in Genetics 20(11):521-524, Elsevier Science Publishers B.V., Netherlands (2004).

Jimeno, A., et al., "Phase 1 study of REGN421 (R)/SAR153192, a fully-human delta-like ligand 4 (Dll4) monoclonal antibody (mAb), in patients with advanced solid tumors," ASCO University 2013 ASCO Annual Meeting accessed at http://meetinglibrary.asco.org/content/113836-132, 2 pages.

Kazanskaya, O., et al., "R-Spondin2 is a Secreted activator of Wnt/.beta.-Catenin Signaling and is required for Xenopus Myogenesis," Developmental Cell 7:525-534, Cell Press, United States (2004).

Kim, E.S., et al., "Potent VEGF blockade causes regression of coopted vessels in a model of neuroblastoma," Proceedings of the National Academy of Sciences 99(17):11399-11404, National Academy of Sciences, United States (2002).

Korinek, V., et al., "Constitutive Transcriptional Activation by a Beta-Catenin-Tcf Complex in APC -/- Colon Carcinoma," Science 275(5307):1784-1787, American Association for the Advancement of Science, United States (1997).

Kuo, C.J., et al., "Comparative evaluation of the antitumor activity of antiangiogenic proteins delivered by gene transfer," Proceedings of the National Academy of Sciences 98(8):4605-4610, National Academy of Sciences, United States (2001).

Li, X., et al., "Notch3 Signaling is Required for the Development of Pulmonary Arterial Hypertension," Nature Medicine 15(15)11:1289-1297, Nature Publishing Company, United States (2009).

Lievre, A., et al., "KRAS Mutation Status is Predictive of Response to Cetuximab Therapy in Colorectal Cancer," Cancer Research 66(8):3992-3995, American Association for Cancer Research, United States (2006).

Lonberg, N., "Human Antibodies from Transgenic Animals," Nature Biotechnology 23(9):1117-1125, Nature Publishing Group, United Kingdom (2005).

Lu, K.V., and Bergers, G., "Mechanisms of evasive resistance to anti-VEGF therapy in glioblastoma," CNS Oncology 2(1):49-65, Future Medicine, Inc., United States (2013).

Luca, V.C., et al., "Structural basis for Notch1 engagement of Delta-like 4," Science, 347(6224):847-853, American Association for the Advancement of Science, United States (2015).

McKeage, M., et al., "A Phase 1b study of demcizumab (DEM, anti-DLL4) plus pemetrexed and carboplatin in patients with first line stage lllb/IV non-squamous non-small cell lung cancer," Proceedings

(56) References Cited

OTHER PUBLICATIONS of the AACR-NCI-EORTC International Conference on Molecular Targets and Cancer Therapeutics, Oct. 19-23, 2013, Abstract A71, 2 pages (2013).
McKeage, M.J., et al., "A phase 1b study of the anticancer stem cell agent demcizumab (DEM), pemetrexed (PEM), and carboplatin (CARBO) in pts with first-line nonsquamous NSCLC," 2014 ASCO Annual Meeting, Abstract 2544, 2 pages (2014).
Meniel, V. and Clarke, A.R., "Wnt-Cadherin Connections in Normal and Neoplastic Mammary Epithelium," Journal of Mammary Gland Biology and Neoplasia 8(4):435-447, Kluwer Academic/Plenum Publishers, United States (2003).
OncoMed Pharmaceuticals, Press Release, "Clinical Cancer Research Publishes OncoMed Data Demonstrating Anti-Cancer Activity for Anti-DLL4 (Demcizumab) in Pancreatic Cancer," Sep. 6, 2012, 2 pages.
OncoMed Pharmaceuticals, Press Release, "OncoMed Announces Abstracts Accepted at the 2014 ASCO Annual Meeting," Apr. 23, 2014, 2 pages.
OncoMed Pharmaceuticals, Press Release, "OncoMed Anti-Cancer Stem Cell Antibody OMP-21M18 Demonstrates Potent Activity in Preclinical Studies Against Human Colon Cancer Tumors Regardless of KRAS Mutation Status," Mar. 1, 2011, 3 pages.
OncoMed Pharmaceuticals, Press Release, "OncoMed's Demcizumab Phase 1b Clinical Trials Show Encouraging Safety and Anti-Tumor Activity at ESMO," Sep. 28, 2014, 3 pages.
OncoMed Pharmaceuticals, Press Release, "OncoMed Pharmaceuticals Announces Presentations of Anti-Notch2/3 and Demcizumab Clinical Data at EORTC-NCI-AACR Meeting," Nov. 9, 2012, 3 pages.
OncoMed Pharmaceuticals, Press Release, "OncoMed Pharmaceuticals Initiates Phase 1b/2 Clinical Trial of Demcizuman (Anti-DLL4) in Combination with Paclitaxel in Ovarian Cancer," Sep. 19, 2013, 3 pages.
OncoMed Pharmaceuticals Press Release, "OncoMed Pharmaceuticals Presents Data From Clinical Trials of Four Novel Anti-Cancer Stem Cell (Anti-CSC) Therapeutics at the AACR-NCI-EORTC International Conference on Molecular Targets and Cancer Therapeutics in Boston, Oct. 19-23, 2013," Oct. 21, 2013, 4 pages.
OncoMed Pharmaceuticals, Press Release, "OncoMed Pharmaceuticals Presents Data From Demcizumab Phase 1b Clinical Study in Pancreatic Cancer at the 2014 Gastrointestinal Cancers Symposium," Jan. 17, 2014, 3 pages.
OncoMed Pharmaceuticals Press Release, "OncoMed Pharmaceuticals Recaps New Data Presented at AACR," Apr. 3, 2012, 2 pages.
OncoMed Pharmaceuticals Press Release, "OncoMed Pharmaceuticals to Present Data From Clinical Trials of Four Novel Anti-Cancer Stem Cell (Anti-CSC) Therapeutics in Five Posters at the AACR-NCI-EORTC International Conference on Molecular Targets and Cancer Therapeutics in Boston, Oct. 19-23, 2013," Oct. 14, 2013, 4 pages.
OncoMed Pharmaceuticals Press Release, "OncoMed Pharmaceuticals to Present Data from Two Clinical Programs in Advanced Pancreatic Cancer at the 2014 Gastrointestinal Cancers Symposium," Jan. 9, 2014, 2 pages.
OncoMed Pharmaceuticals, Press Release, "OncoMed Pharmaceuticals Updates Phase 1b Data for Demcizumab With Pemetrexed and Carboplatin in Patients With First-Line Stage lllb/IV Non-Small Cell Lung Cancer at the AACR-NCO-EORTC International Conference on Molecular Targets and Cancer Therapeutics in Boston, Oct. 19-23, 2013," Oct. 20, 2013, 3 pages.
OncoMed Pharmaceuticals, Press Release, "OncoMed Presents Data on Multiple Anti-Cancer Stem Cell Programs at American Association for Cancer Research Annual Meeting," Apr. 8, 2014, 4 pages.
OncoMed Pharmaceuticals Press Release, "OncoMed Presents New Clinical and Biomarker Data From Its Tarextumab and Demcizumab Clinical Trials at the EORTC-NCI-AACR Symposium," Nov. 21, 2014, 3 pages.
OncoMed Pharmaceuticals Press Release, "OncoMed Presents New Data in Six Anti-Cancer Stem Cell Programs at AACR," Apr. 9, 2013, 3 pages.
OncoMed Pharmaceuticals Press Release, "OncoMed to Present Clinical and Preclinical Data at the 26th EORTC-NCI-AACR Symposium on Molecular Targets and Cancer Therapeutics Meeting," Oct. 30, 2014, 2 pages.
OncoMed Pharmaceuticals Press Release, "OncoMed to Present Data From Three Clinical Studies at the 2014 ASCO Annual Meeting," May 14, 2014, 4 pages.
OncoMed Pharmaceuticals Press Release, "OncoMed to Present New and Emerging Data from Demcizumab (anti-DLL4, OMP-21M18) and Tarextumab (anti-Notch2/3, OMP-59R5) Clinical Studies at the European Society for Medical Oncology 2014 Congress," Sep. 17, 2014, 2 pages.
OncoMed Pharmaceuticals Press Release, "OncoMed To Present New Data in Six Anti-Cancer Stem Cell Programs at AACR," Apr. 2, 2013, 2 pages.
Perantoni, A.O., "Renal Development: Perspectives on a Wnt-Dependent Process," Seminars in Cells and Development Biology Abstract, 1 page, Academic Press, United Kingdom (2003).
Pisano, C., et al., "Undersulfated, low-molecular-weight glycol-split heparin as an antiangiogenic VEGF antagonist," Glycobiology 15(2):1C-6C, Oxford University Press, England (2005).
Polakis, P., "Wnt signaling and cancer," Genes & Development 14:1837-1851, Cold Spring Harbor Laboratory Press, United States (2000).
Polesskaya, A., et al., "Wnt Signaling Induces the Myogenic Specification of Resident CD45+ Adult Stem Cells during Muscle Regeneration," Cell Abstract, 1 page, MIT Press, United States (2003).
Rehman, A.O. and Wang, C-U, "Notch signaling in the regulation of tumor angiogenesis," TRENDS in Cell Biology 16(6):293-300, Elsevier Ltd., England (2006).
Reply to European Opposition Brief for European Patent No. 2157192 filed Jan. 8, 2015, 42 pages.
Response to European Opposition Brief Reply for European Patent No. 2157192, filed May 14, 2015, 14 pages.
Saadi-Kheddouci, S., et al., "Early Development of Polycystic Kidney Disease in Transgenic Mice Expressing an Activated Mutant of the Beta-Catenin Gene," Oncogene 20(42):5972-5981, Nature Publishing Group, England (2001).
Sica, D.A., "Angiogenesis Inhibitors and Hypertension," US Cardiovascular Disease 79-80, Touch Briefings, United States (2007).
Smalley, M.J. and Dale, T.C., "Wnt Signalling in Mammalian Development and Cancer," Cancer and Metastasis Reviews 18(2):215-230, Kluwer Academic Publishers, Netherlands (1999).
Stump, R.J., et al., "A Role for Wnt/Beta-Catenin Signaling in Lens Epithelial Differentiation," Developmental Biology Abstract, 1 page, Elsevier Inc., United States (2003).
Sullivan, C.C. and Bicknell, R., "New molecular pathways in angiogenesis," British Journal of Cancer 89:228-231, Cancer Research UK, United Kingdom (2003).
Surendran, K., et al, "A Role for Wnt-4 in Renal Fibrosis," American Journal of Physiology. Renal Physiology 282(3):F431-F441, American Physiological Society, United Sates (2002).
Tavares, M.J., et al., "Inhibition of Vascular Endothelium by the Notch-Ligand Delta-4 Unveils a Novel Therapeutic Target," Abstract#1944, Poster Board Session: 115-11, Blood 102(11):3 pages, American Society of Hematology, United States (2003).
Thurston, G., and Gale, N.W., "Vascular Endothelial Growth Factor and Other Signaling Pathways in Developmental and Pathologic Angiogenesis," International Journal of Hematology 80:7-20, The Japanese Society of Hematology, Japan (2004).
Ton, N.C. and Jayson, G.C., "Resistance to Anti-VEGF Agents," Current Pharmaceutical Design 10:51-64, Bentham Science Publishers Ltd., Netherlands (2004).
UniProt "Thrombospondin-1," identifying No. P07996-TSP1_HUMAN, accessed at http://www.uniprot.org/uniprot/P07996, accessed on Sep. 25, 2014, 14 pages.

(56) References Cited

OTHER PUBLICATIONS

Wong, O.K., et al., "Voreloxin (formerly SNS-595) is a potent DNA intercalator and topoisomerase II poison that induces cell cycle dependent DNA damage and rapid apoptosis in cancer cell lines," 24th EORTC-NCI-AACR Symposium, Nov. 9, Poster 169, 1 page (2012).

Wu, W., et al., "Mutual Antagonism between Dickkopf1 and Dickkopf2 Regulates Wnt/Beta-Catenin Signalling," Current Biology 10(24):1611-1614, Elsevier Science Ltd., England (2000).

Yen, W-C., et al., "Anti-DLL4 (demcizumab) inhibits tumor growth and reduces cancer stem cell frequency in patient-derived ovarian cancer xenografts," AACR 104th Annual Meeting 2013, Abstract 3725, Apr. 6-10, 1 page (2013).

Yen, W-C., et al., "Dual targeting of DLL4 and VEGF signaling by a novel bispecific antibody inhibits tumor growth and reduces cancer stem cell frequency," AACR Annual Meeting 2014, Apr. 5-9, 2014, Abstract 207, 1 page (2014).

Yen, W-C., et al., "Targeting cancer stem cells by an anti-DLL4 antibody inhibits epithelial-to-mesenchymal transition, delays tumor recurrence and overcomes drug resistance in breast and pancreatic cancer," AACR 103rd Annual Meeting 2012, Mar. 31-Apr. 4, Abstract 3357, 1 page (2013).

Yen, W-C., et al., "The combination of gemcitabine/nab-paclitaxel and anti-DLL4 (demcizumab) produces synergistic growth inhibition, delays tumor recurrence and reduces tumor initiating cells in pancreatic cancer," American Association for Cancer Research Annual Meeting 2014, Abstract 1898, 1 page (2014).

Office Action mailed Apr. 16, 2015, in U.S. Appl. No. 12/782,429, Gurney, A. et al., filed May 18, 2010.

Figure 2
DLL4 Antibodies Block the Interaction of DLL4 with the Human Notch Receptor
A
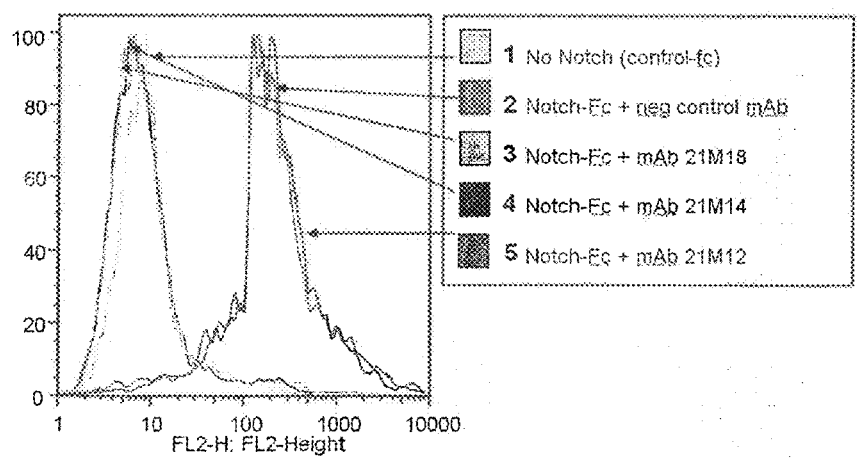
B
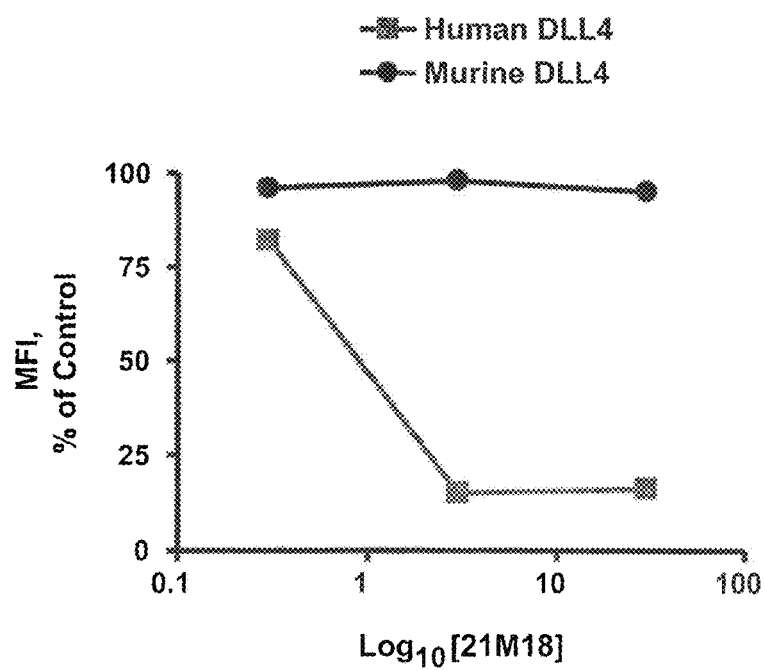

21M14 and 21M18 Block DLL4 Mediated Notch signaling

Figure 7
DLL4 Antibodies Modulate Expression of Notch Target Genes in Colon Tumors
A
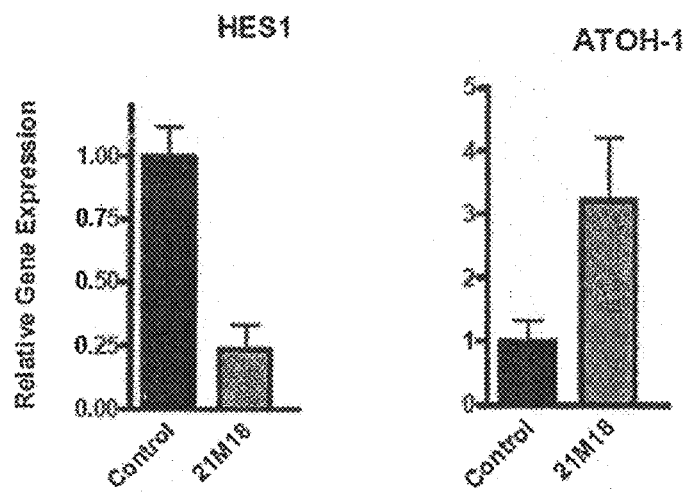
B
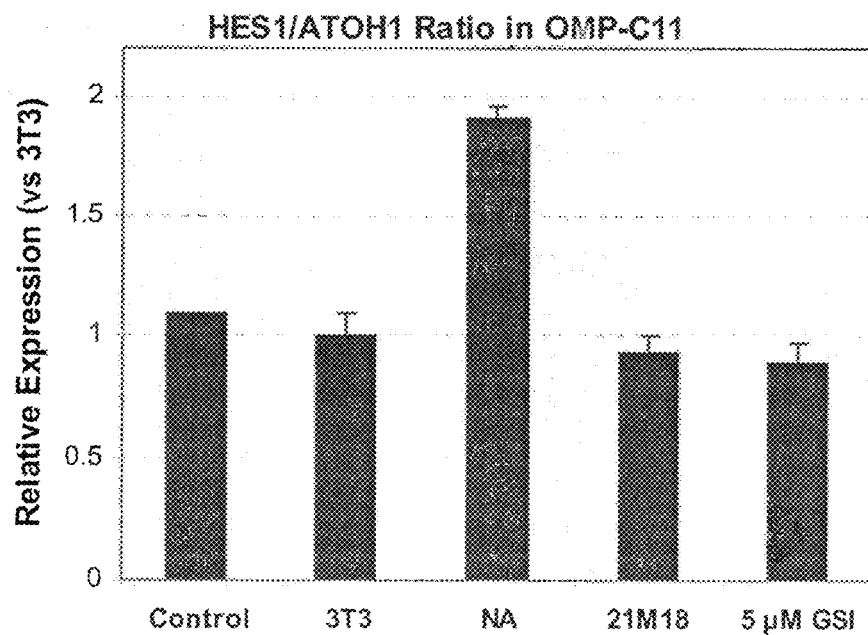

Anti-DLL4 21M18 Antibodies Reduces the Number of Proliferating Tumor Cells in Vivo Figure 10
Anti-DLL4 and 5-FU Reduce UM-C4 Colon Tumor Growth
A
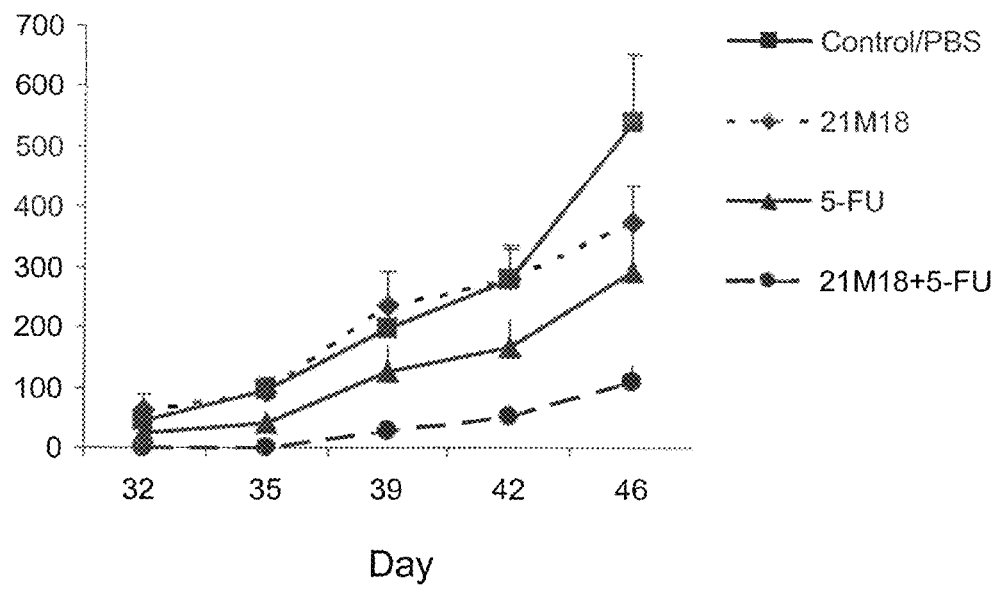
B
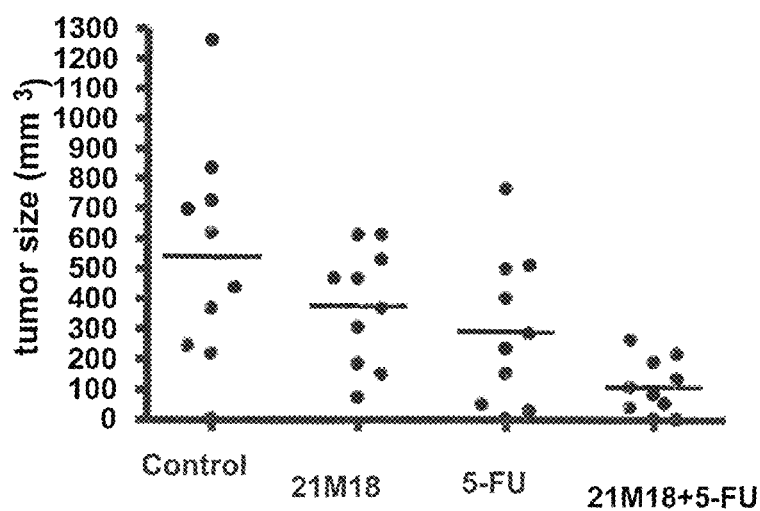

Combination of anti-DLL4 and anti-EGFR Inhibits UM-C4
Tumor Growth

Figure 12
Anti-DLL4 mAb 21M18 and Irinotecan Act Synergistically to Inhibit Colon Tumor Growth
A
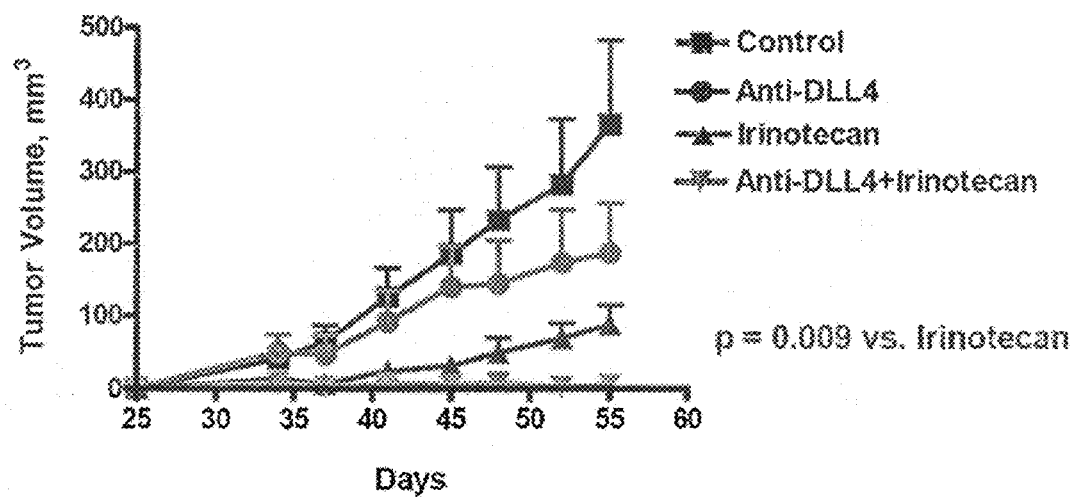
B
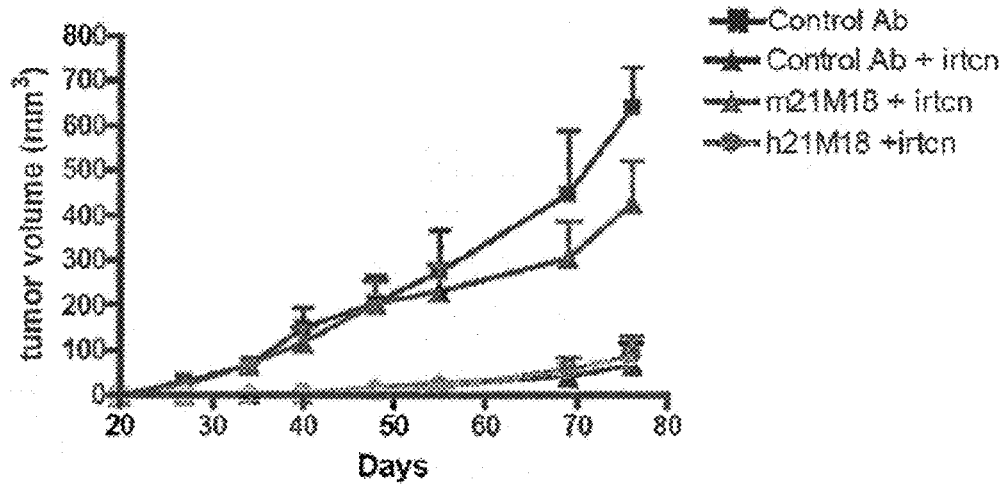

21M18 and Anti-VEGF Inhibit Colon Tumor Growth

COMPOSITIONS AND METHODS FOR DIAGNOSING AND TREATING CANCER

CROSS REFERENCE TO RELATED APPLICATIONS

This application is a division of U.S. application Ser. No. 12/782,429, filed May 18, 2010, which is a continuation of U.S. application Ser. No. 11/905,392, filed Sep. 28, 2007, now U.S. Pat. No. 7,750,124, which claims the benefit of U.S. Provisional Appl. No. 60/847,904, filed Sep. 29, 2006; 60/886,260, filed Jan. 23, 2007; and 60/942,542, filed Jun. 7, 2007; each of which is incorporated herein by reference.

REFERENCE TO A SEQUENCE LISTING SUBMITTED ELECTRONICALLY VIA EFS-WEB

The content of the electronically submitted sequence listing (Name: 22930250007SequenceListingascii.txt, Size: 29 KB; and Date of Creation: Mar. 11, 2013) is herein incorporated by reference in its entirety.

DESCRIPTION OF THE INVENTION

1. Field

The present invention relates to the field of oncology and provides novel compositions and methods for diagnosing and treating cancer. The present invention provides antibodies against a cancer stem cell marker for the diagnosis and treatment of solid tumors.

2. Background

Cancer is one of the leading causes of death in the developed world, with over one million people diagnosed with cancer and 500,000 deaths per year in the United States alone. Overall it is estimated that more than 1 in 3 people will develop some form of cancer during their lifetime. There are more than 200 different types of cancer, four of which—breast, lung, colorectal, and prostate—account for over half of all new cases (Jemal et al., 2003, Cancer J. Clin. 53:5-26).

Breast cancer is the most common cancer in women, with an estimate 12% of women at risk of developing the disease during their lifetime. Although mortality rates have decreased due to earlier detection and improved treatments, breast cancer remains a leading cause of death in middle-aged women, and metastatic breast cancer is still an incurable disease. On presentation, most patients with metastatic breast cancer have only one or two organ systems affected, but as the disease progresses, multiple sites usually become involved. The most common sites of metastatic involvement are locoregional recurrences in the skin and soft tissues of the chest wall, as well as in axilla and supraclavicular areas. The most common site for distant metastasis is the bone (30-40% of distant metastasis), followed by the lungs and liver. And although only approximately 1-5% of women with newly diagnosed breast cancer have distant metastasis at the time of diagnosis, approximately 50% of patients with local disease eventually relapse with metastasis within five years. At present the median survival from the manifestation of distant metastases is about three years.

Current methods of diagnosing and staging breast cancer include the tumor-node-metastasis (TNM) system that relies on tumor size, tumor presence in lymph nodes, and the presence of distant metastases (American Joint Committee on Cancer: AJCC Cancer Staging Manual. Philadelphia, Pa.: Lippincott-Raven Publishers, 5th ed., 1997, pp 171-180; Harris, J R: "Staging of breast carcinoma" in Harris, J. R., Hellman, S., Henderson, I. C., Kinne D. W. (eds.): Breast Diseases. Philadelphia, Lippincott, 1991). These parameters are used to provide a prognosis and select an appropriate therapy. The morphologic appearance of the tumor can also be assessed but because tumors with similar histopathologic appearance can exhibit significant clinical variability, this approach has serious limitations. Finally assays for cell surface markers can be used to divide certain tumors types into subclasses. For example, one factor considered in the prognosis and treatment of breast cancer is the presence of the estrogen receptor (ER) as ER-positive breast cancers typically respond more readily to hormonal therapies such as tamoxifen or aromatase inhibitors than ER-negative tumors. Yet these analyses, though useful, are only partially predictive of the clinical behavior of breast tumors, and there is much phenotypic diversity present in breast cancers that current diagnostic tools fail to detect and current therapies fail to treat.

Prostate cancer is the most common cancer in men in the developed world, representing an estimated 33% of all new cancer cases in the U.S., and is the second most frequent cause of death (Jemal et al., 2003, CA Cancer J. Clin. 53:5-26). Since the introduction of the prostate specific antigen (PSA) blood test, early detection of prostate cancer has dramatically improved survival rates; the five year survival rate for patients with local and regional stage prostate cancers at the time of diagnosis is nearing 100%. Yet more than 50% of patients will eventually develop locally advanced or metastatic disease (Muthuramalingam et al., 2004, Clin. Oncol. 16:505-16).

Currently radical prostatectomy and radiation therapy provide curative treatment for the majority of localized prostate tumors. However, therapeutic options are very limited for advanced cases. For metastatic disease, androgen ablation with luteinising hormone-releasing hormone (LHRH) agonist alone or in combination with anti-androgens is the standard treatment. Yet despite maximal androgen blockage, the disease nearly always progresses with the majority developing androgen-independent disease. At present there is no uniformly accepted treatment for hormone refractory prostate cancer, and chemotherapeutic regimes are commonly used (Muthuramalingam et al., 2004, Clin. Oncol. 16:505-16; Trojan et al., 2005, Anticancer Res. 25:551-61).

Colorectal cancer is the third most common cancer and the fourth most frequent cause of cancer deaths worldwide (Weitz et al., 2005, Lancet 365:153-65). Approximately 5-10% of all colorectal cancers are hereditary with one of the main forms being familial adenomatous polyposis (FAP), an autosomal dominant disease in which about 80% of affected individuals contain a germline mutation in the adenomatous polyposis coli (APC) gene. Colorectal carcinomas invade locally by circumferential growth and elsewhere by lymphatic, hematogenous, transperitoneal, and perineural spread. The most common site of extralymphatic involvement is the liver, with the lungs the most frequently affected extra-abdominal organ. Other sites of hematogenous spread include the bones, kidneys, adrenal glands, and brain.

The current staging system for colorectal cancer is based on the degree of tumor penetration through the bowel wall and the presence or absence of nodal involvement. This staging system is defined by three major Duke's classifications: Duke's A disease is confined to submucosa layers of colon or rectum; Duke's B disease has tumors that invade through the muscularis propria and may penetrate the wall of the colon or rectum; and Duke's C disease includes any degree of bowel wall invasion with regional lymph node metastasis. While surgical resection is highly effective for early stage colorectal cancers, providing cure rates of 95% in Duke's A patients, the rate is reduced to 75% in Duke's B patients and the presence of positive lymph node in Duke's C disease predicts a 60% likelihood of recurrence within five years. Treatment of Duke's C patients with a post surgical course of chemotherapy reduces the recurrence rate to 40%-50% and is now the standard of care for these patients.

Lung cancer is the most common cancer worldwide, the third most commonly diagnosed cancer in the United States, and by far the most frequent cause of cancer deaths (Spiro et al., 2002, *Am. J. Respir. Crit. Care Med.* 166:1166-96; Jemal et al., 2003, *CA Cancer J. Clin.* 53:5-26). Cigarette smoking is believed responsible for an estimated 87% of all lung cancers making it the most deadly preventable disease. Lung cancer is divided into two major types that account for over 90% of all lung cancers: small cell lung cancer (SCLC) and non-small cell lung cancer (NSCLC). SCLC accounts for 15-20% of cases and is characterized by its origin in large central airways and histological composition of sheets of small cells with little cytoplasm. SCLC is more aggressive than NSCLC, growing rapidly and metastasizing early. NSCLC accounts for 80-85% of all cases and is further divided into three major subtypes based on histology: adenocarcinoma, squamous cell carcinoma (epidermoid carcinoma), and large cell undifferentiated carcinoma.

Lung cancer typically presents late in its course, and thus has a median survival of only 6-12 months after diagnosis and an overall 5 year survival rate of only 5-10%. Although surgery offers the best chance of a cure, only a small fraction of lung cancer patients are eligible with the majority relying on chemotherapy and radiotherapy. Despite attempts to manipulate the timing and dose intensity of these therapies, survival rates have increased little over the last 15 years (Spiro et al., 2002, *Am. J. Respir. Crit. Care Med.* 166:1166-96).

These four cancers, as well as many others, present as solid tumors that are composed of heterogeneous cell populations. For example, breast cancers are a mixture of cancer cells and normal cells, including mesenchymal (stromal) cells, inflammatory cells, and endothelial cells. Several models of cancer provide different explanations for the presence of this heterogeneity. One model, the classic model of cancer, holds that phenotypically distinct cancer cell populations all have the capacity to proliferate and give rise to a new tumor. In the classical model, tumor cell heterogeneity results from environmental factors as well as ongoing mutations within cancer cells resulting in a diverse population of tumorigenic cells. This model rests on the idea that all populations of tumor cells have some degree of tumorigenic potential. (Pandis et al., 1998, *Genes, Chromosomes & Cancer* 12:122-129; Kuukasjrvi et al., 1997, *Cancer Res.* 57:1597-1604; Bonsing et al., 1993, *Cancer* 71:382-391; Bonsing et al., 2000, *Genes Chromosomes & Cancer* 82: 173-183; Beerman H et al., 1991, *Cytometry* 12:147-54; Aubele M & Werner M, 1999, *Analyt. Cell. Path.* 19:53; Shen L et al., 2000, *Cancer Res.* 60:3884).

An alternative model for the observed solid tumor cell heterogeneity derives from the impact of stem cells on tumor development. According to this model, cancer arises from dysregulation of the mechanisms that control normal tissue development and maintenance. (Beachy et al., 2004, *Nature* 432:324). During normal animal development, cells of most or all tissues are derived from normal precursors, called stem cells (Morrison et al., 1997, *Cell* 88:287-98; Morrison et al., 1997, *Curr. Opin. Immunol.* 9:216-21; Morrison et al., 1995, *Annu. Rev. Cell. Dev. Biol.* 11:35-71). Stem cells are cells that: (1) have extensive proliferative capacity; 2) are capable of asymmetric cell division to generate one or more kinds of progeny with reduced proliferative and/or developmental potential; and (3) are capable of symmetric cell divisions for self-renewal or self-maintenance. The best-studied example of adult cell renewal by the differentiation of stem cells is the hematopoietic system where developmentally immature precursors (hematopoietic stem and progenitor cells) respond to molecular signals to form the varied blood and lymphoid cell types. Other cells, including cells of the gut, breast ductal system, and skin are constantly replenished from a small population of stem cells in each tissue, and recent studies suggest that most other adult tissues also harbor stem cells, including the brain. Tumors derived from a "solid tumor stem cell" (or "cancer stem cell" from a solid tumor) subsequently undergoes chaotic development through both symmetric and asymmetric rounds of cell divisions. In this stem cell model, solid tumors contain a distinct and limited (possibly even rare) subset of cells that share the properties of normal "stem cells", in that they extensively proliferate and efficiently give rise both to additional solid tumor stem cells (self-renewal) and to the majority of tumor cells of a solid tumor that lack tumorigenic potential. Indeed, mutations within a long-lived stem cell population may initiate the formation of cancer stem cells that underlie the growth and maintenance of tumors and whose presence contributes to the failure of current therapeutic approaches.

The stem cell nature of cancer was first revealed in the blood cancer, acute myeloid leukemia (AML) (Lapidot et al., 1994, *Nature* 17:645-8). More recently it has been demonstrated that malignant human breast and colon tumors similarly harbor a small, distinct population of cancer stem cells enriched for the ability to form tumors in immunodeficient mice. An ESA+, CD44+, CD24−/low, Lin− cell population in breast tumors was found to be 50-fold enriched for tumorigenic cells compared to unfractionated tumor cells (Al-Hajj et al., 2003, *Proc. Nat'l Acad. Sci.* 100:3983-8). Similarly, the ESA+, CD44+ subpopulation in colorectal tumors was found to uniquely include tumorigenic cells, and the addition of CD166 to this profile was able to further enrich for colon cancer stem cells (CoCSC) (Dalerba et al. 2007 *Proc Nat'l Acad Sci* 104:10158-63). The ability to prospectively isolate the tumorigenic cancer cells has permitted investigation of critical biological pathways that underlie tumorigenicity in these cells, and thus promises the development of better diagnostic assays and therapeutics for cancer patients. It is toward this purpose that this invention is directed.

SUMMARY

Provided are antibodies that specifically bind to a human Delta-like ligand 4 (DLL4) epitope formed by a combination of the human DLL4 N-terminal region (SEQ ID NO: 27) and human DSL domain (SEQ ID NO: 26), wherein the antibody affects tumor growth. Also provided is a pharmaceutical composition comprising an antibody of the present disclosure and a pharmaceutically acceptable vehicle. Further provided is a method of treating cancer comprising administering a therapeutically effective amount of a DLL4 antibody of the present disclosure.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims. It is to be understood that both the foregoing general description and the following detailed description are exemplary and explanatory only and are not restrictive of the invention, as claimed. The accompanying drawings, which are incorporated in and constitute a part of this specification, illustrate several embodiments of the invention and, together with the description, serve to explain the principles of the invention. In the specification and the appended claims, the singular forms "a," "an," and "the" include plural reference unless the context clearly dictates otherwise.

BRIEF DESCRIPTION OF THE DRAWINGS

FIG. 2: DLL4 Antibodies Block the Interaction of Human DLL4 with the Notch Receptor. A) HEK 293 cells expressing DLL4 were incubated with Notch-Fc or control Fc protein in the presence of DLL4 or control antibodies. High fluorescence intensity indicates the presence of Notch and DLL4 binding in the presence of a control antibody (line 2) and 21M12 anti-DLL4 antibodies (line 5). Low fluorescence intensity indicates the absence of Notch and DLL4 interactions in the absence of Notch (line 1) and the disruption of Notch and DLL4 interactions in the presence of anti-DLL4 antibodies 21M18 (line 3) and 21M14 (line 4). B) HEK 293 cells expressing Notch1 were incubated with either human or murine DLL4-Fc. Binding was detected by fluorescently labeled anti-Fc and analyzed by FACS, with high fluorescence intensity indicative of binding between DLL4 and Notch1 expressing cells. 21M18 blocks binding of human DLL4 (gray squares) but not murine DLL4 (black circles) to the Notch receptor.

FIG. 5: Sequence alignment of the light chain variable region. Parental murine 21M18 antibody sequence (m-21M18-Vk, top) (SEQ ID NO:34), human germline sequence (h-germline Vk, middle) (SEQ ID NO:35), and humanized 21M18 light chain variable region sequence (21M18-L2, bottom) (SEQ ID NO:36) are shown with conserved amino acid residues shaded in black. The three CDRs are marked showing retention of parental murine sequences in the humanized 21M18 antibody. The two retained murine residues within the variable framework region are numbered 1-2 at their corresponding Kabat positions 22 and 36.

FIG. 7: DLL4 Antibodies Modulate Expression of Notch Target Genes in Colon Tumors. A) C8 colon tumors treated with anti-DLL4 21M18 antibodies or PBS (Control) were isolated and expression of HES1 and ATOH-1 determined by quantitative RT-PCR. Relative gene expression (y-axis) compared to control treated cells shows that treatment with anti-DLL4 antibodies decreased expression of HES1 and increased expression of ATOH-1. B) Relative expression ratio (y-axis) of HES1 versus ATOH1 in mouse lineage-depleted OMP-C11 colon tumor cell colonies is shown. C11 colonies overlaid with 3T3 cells overexpressing DLL4 (3T3+DLL4) showed an increased in the HES1/ATOH1 expression ratio compared to colon cells overlaid with 3T3 cells (3T3) or not exposed to cell overlay (Control). This increase in the HES1/ATOH1 expression ratio was eliminated by incubation with 10 ug/mL 21M18 antibodies (21M18) or 5 uM-secretase inhibitor DBZ (5 uM GSI).

FIG. 10: Treatment with DLL4 Antibodies in Combination with Fluorouracil (5-FU) Reduces Tumor Growth. NOD/SCID mice were injected with dissociated UM-C4 cells and treated with anti-DLL4 antibodies or PBS in the presence or absence of 5-FU. A) Treatment with 21M18 antibodies in combination with 5-FU (circles, dashed line) reduced tumor growth 46 days after injection of tumor cells to a greater degree than treatment with either 5-FU (triangles, solid line) or 21M18 antibodies (diamonds, dotted line) alone and to a greater degree than PBS injected controls (squares, solid line). Tumor volume in $mm^3$ is indicated on the y-axis. B) Plots of tumor measurements on day 46 from individual animals. Each dot represents one animal. Treatment with 21M18 antibodies or 5-FU each reduced tumor size ($mm^3$) compared to control. Furthermore, combination treatment with 21M18 antibodies and 5-FU had an additive effect, reducing tumor size to ⅕ the size of control.

FIG. 12: Anti-DLL4 mAb 21M18 and Irinotecan Act Synergistically to Inhibit Colon Tumor Growth. NOD/SCID mice were injected with dissociated C8 cells and treated with anti-DLL4 antibodies or control antibody in the presence or absence of Irinotecan. A) Treatment with murine 21M18 antibodies (circles) or Irinotecan (triangles) alone each reduced tumor volume (y-axis $mm^3$) compared to control treated animals (black squares). However, combination treatment with 21M18 and Irinotecan (inverse triangles) had a synergistic effect, completely eliminating tumor growth for up to 55 days post-cell injection. B) Treatment with humanized 21M18 (h21M18) in combination with Irinotecan (irtcn) (circles) has similar efficacy as murine 21M18 (m21M18) (triangles) as compared to control antibody (black squares) or control antibody with Irinotecan (triangles).

DESCRIPTION OF THE EMBODIMENTS

Figure 1:
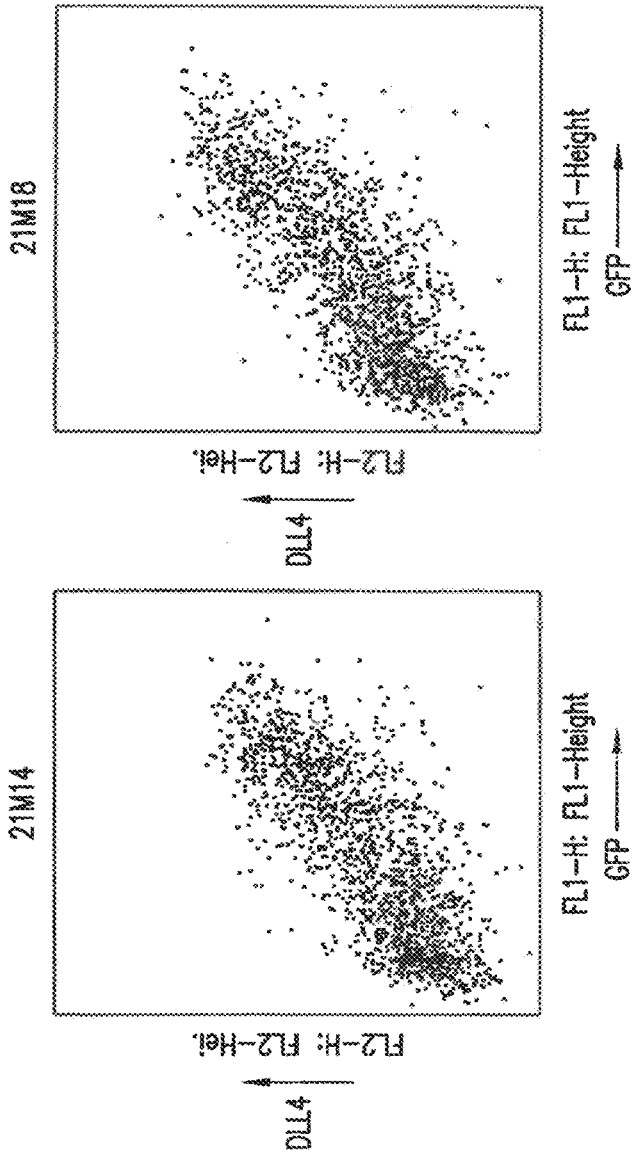
FIG. 1: Specific Binding of anti-DLL4 21M18 Antibodies to Native Cell-Surface DLL4 Protein. HEK 293 cells co-transfected with full-length DLL4 and GFP were incubated with anti-DLL4 antibodies and sorted by FACS. Anti-DLL4 antibodies 21M14 and 21M18 show specific binding to cells expressing DLL4 as revealed by the linear relationship between DLL4 antibody binding and GFP expression.

The term "antibody" is used to mean an immunoglobulin molecule that recognizes and specifically binds to a target, such as a protein, polypeptide, peptide, carbohydrate, polynucleotide, lipid, or combinations of the foregoing through at least one antigen recognition site within the variable region of the immunoglobulin molecule. In certain embodiments, antibodies of the present invention include antagonist antibodies that specifically bind to a cancer stem cell marker protein and interfere with, for example, ligand binding, receptor dimerization, expression of a cancer stem cell marker protein, and/or downstream signaling of a cancer stem cell marker protein. In certain embodiments, disclosed antibodies include agonist antibodies that specifically bind to a cancer stem cell marker protein and promote, for example, ligand binding, receptor dimerization, and/or signaling by a cancer stem cell marker protein. In certain embodiments, disclosed antibodies do not interfere with or promote the biological activity of a cancer stem cell marker protein but inhibit tumor growth by, for example, antibody internalization and/or recognition by the immune system. As used herein, the term "antibody" encompasses intact polyclonal antibodies, intact monoclonal antibodies, antibody fragments (such as Fab, Fab', F(ab')2, and Fv fragments), single chain Fv (scFv) mutants, multispecific antibodies such as bispecific antibodies generated from at least two intact antibodies, chimeric antibodies, humanized antibodies, human antibodies, fusion proteins comprising an antigen determination portion of an antibody, and any other modified immunoglobulin molecule comprising an antigen recognition site so long as the antibodies exhibit the desired biological activity. An antibody can be of any the five major classes of immunoglobulins: IgA, IgD, IgE, IgG, and IgM, or subclasses (isotypes) thereof (e.g. IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well known subunit structures and three-dimensional configurations. Antibodies can be naked or conjugated to other molecules such as toxins, radioisotopes, etc.

As used herein, the term "antibody fragment" refers to a portion of an intact antibody and refers to the antigenic determining variable regions of an intact antibody. Examples of antibody fragments include, but are not limited to Fab, Fab', F(ab')2, and Fv fragments, linear antibodies, single chain antibodies, and multispecific antibodies formed from antibody fragments.

An "Fv antibody" refers to the minimal antibody fragment that contains a complete antigen-recognition and -binding site either as two-chains, in which one heavy and one light chain variable domain form a non-covalent dimer, or as a single-chain (scFv), in which one heavy and one light chain variable domain are covalently linked by a flexible peptide linker so that the two chains associate in a similar dimeric structure. In this configuration the complementarity determining regions (CDRs) of each variable domain interact to define the antigen-binding specificity of the Fv dimer. Alternatively a single variable domain (or half of an Fv) can be used to recognize and bind antigen, although generally with lower affinity.

A "monoclonal antibody" as used herein refers to homogenous antibody population involved in the highly specific recognition and binding of a single antigenic determinant, or epitope. This is in contrast to polyclonal antibodies that typically include different antibodies directed against different antigenic determinants. The term "monoclonal antibody" encompasses both intact and full-length monoclonal antibodies as well as antibody fragments (such as Fab, Fab', F(ab')2, Fv), single chain (scFv) mutants, fusion proteins comprising an antibody portion, and any other modified immunoglobulin molecule comprising an antigen recognition site. Furthermore, "monoclonal antibody" refers to such antibodies made in any number of manners including but not limited to by hybridoma, phage selection, recombinant expression, and transgenic animals.

As used herein, the term "humanized antibody" refers to forms of non-human (e.g. murine) antibodies that are specific immunoglobulin chains, chimeric immunoglobulins, or fragments thereof that contain minimal non-human sequences. Typically, humanized antibodies are human immunoglobulins in which residues from the complementarity determining regions (CDRs) within the antigen determination region (or hypervariable region) of the variable region of an antibody chain or chains are replaced by residues from the CDR of a non-human species (e.g. mouse, rat, rabbit, hamster) that have the desired specificity, affinity, and capability. In some instances, residues from the variable chain framework region (FR) of a human immunoglobulin are replaced with the corresponding residues in an antibody from a non-human species that has the desired specificity, affinity, and capability. The humanized antibody can be further modified by the substitution of additional residue either in the variable framework region and/or within the replaced non-human residues to refine and optimize antibody specificity, affinity, and/or capability. In general, the humanized antibody will comprise substantially all of at least one, and typically two or three or four, variable domains containing all or substantially all of the CDR regions that correspond to the non-human immunoglobulin whereas all or substantially all of the FR regions are those of a human immunoglobulin consensus sequence. The humanized antibody can also comprise at least a portion of an immunoglobulin constant region or domain (Fc), typically that of a human immunoglobulin. Examples of methods used to generate humanized antibodies are described in U.S. Pat. No. 5,225,539.

The term "human antibody" as used herein means an antibody produced by a human or an antibody having an amino acid sequence corresponding to an antibody produced by a human made using any technique known in the art. This definition of a human antibody includes intact or full-length antibodies, fragments thereof, and/or antibodies comprising at least one human heavy and/or light chain polypeptide such as, for example, an antibody comprising murine light chain and human heavy chain polypeptides.

"Hybrid antibodies" are immunoglobulin molecules in which pairs of heavy and light chains from antibodies with different antigenic determinant regions are assembled together so that two different epitopes or two different antigens can be recognized and bound by the resulting tetramer.

The term "chimeric antibodies" refers to antibodies wherein the amino acid sequence of the immunoglobulin molecule is derived from two or more species. Typically, the variable region of both light and heavy chains corresponds to the variable region of antibodies derived from one species of mammals (e.g. mouse, rat, rabbit, etc) with the desired specificity, affinity, and capability while the constant regions are homologous to the sequences in antibodies derived from another (usually human) to avoid eliciting an immune response in that species.

The term "epitope" or "antigenic determinant" are used interchangeably herein and refer to that portion of an antigen capable of being recognized and specifically bound by a particular antibody. When the antigen is a polypeptide, epitopes can be formed both from contiguous amino acids and noncontiguous amino acids juxtaposed by tertiary folding of a protein. Epitopes formed from contiguous amino acids are typically retained upon protein denaturing, whereas epitopes formed by tertiary folding are typically lost upon protein denaturing. An epitope typically includes at least 3, and more usually, at least 5 or 8-10 amino acids in a unique spatial conformation.

Competition between antibodies is determined by an assay in which the immunoglobulin under test inhibits specific binding of a reference antibody to a common antigen. Numerous types of competitive binding assays are known, for example: solid phase direct or indirect radioimmunoassay (RIA), solid phase direct or indirect enzyme immunoassay (EIA), sandwich competition assay (see Stahli et al., Methods in Enzymology 9:242-253 (1983)); solid phase direct biotin-avidin EIA (see Kirkland et al., J. Immunol. 137:3614-3619 (1986)); solid phase direct labeled assay, solid phase direct labeled sandwich assay (see Harlow and Lane, "Antibodies, A Laboratory Manual," Cold Spring Harbor Press (1988)); solid phase direct label RIA using 1-125 label (see Morel et al., Molec. Immunol. 25(1):7-15 (1988)); solid phase direct biotin-avidin EIA (Cheung et al., Virology 176:546-552 (1990)); and direct labeled RIA (Moldenhauer et al., Scand. J. Immunol. 32:77-82 (1990)). Typically, such an assay involves the use of purified antigen bound to a solid surface or cells bearing either of these, an unlabeled test immunoglobulin and a labeled reference immunoglobulin. Competitive inhibition is measured by determining the amount of label bound to the solid surface or cells in the presence of the test immunoglobulin. Usually the test immunoglobulin is present in excess. Antibodies identified by competition assay (competing antibodies) include antibodies binding to the same epitope as the reference antibody and antibodies binding to an adjacent epitope sufficiently proximal to the epitope bound by the reference antibody for steric hindrance to occur. Usually, when a competing antibody is present in excess, it will inhibit specific binding of a reference antibody to a common antigen by at least 50 or 75%.

That an antibody "selectively binds" or "specifically binds" means that the antibody reacts or associates more frequently, more rapidly, with greater duration, with greater affinity, or with some combination of the above to an epitope than with alternative substances, including unrelated proteins. "Selectively binds" or "specifically binds" means, for instance, that an antibody binds to a protein with a $K_D$ of at least about 0.1 mM, but more usually at least about 1 µM. "Selectively binds" or "specifically binds" means at times that an antibody binds to a protein at times with a $K_D$ of at least about 0.1 µM or better, and at other times at least about 0.01 µM or better. Because of the sequence identity between homologous proteins in different species, specific binding can include an antibody that recognizes a cancer stem cell marker protein in more than one species.

As used herein, the terms "non-specific binding" and "background binding" when used in reference to the interaction of an antibody and a protein or peptide refer to an interaction that is not dependent on the presence of a particular structure (i.e., the antibody is binding to proteins in general rather that a particular structure such as an epitope).

The terms "isolated" or "purified" refer to material that is substantially or essentially free from components that normally accompany it in its native state. Purity and homogeneity are typically determined using analytical chemistry techniques such as polyacrylamide gel electrophoresis or high performance liquid chromatography. A protein (e.g. an antibody) or nucleic acid of the present disclosure that is the predominant species present in a preparation is substantially purified. In particular, an isolated nucleic acid is separated from open reading frames that naturally flank the gene and encode proteins other than protein encoded by the gene. An isolated antibody is separated from other non-immunoglobulin proteins and from other immunoglobulin proteins with different antigen binding specificity. It can also mean that the nucleic acid or protein is in some embodiments at least 80% pure, in some embodiments at least 85% pure, in some embodiments at least 90% pure, in some embodiments at least 95% pure, and in some embodiments at least 99% pure.

As used herein, the terms "cancer" and "cancerous" refer to or describe the physiological condition in mammals in which a population of cells are characterized by unregulated cell growth. Examples of cancer include, but are not limited to, carcinoma, lymphoma, blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma and various types of head and neck cancers.

The terms "proliferative disorder" and "proliferative disease" refer to disorders associated with abnormal cell proliferation such as cancer.

"Tumor" and "neoplasm" as used herein refer to any mass of tissue that result from excessive cell growth or proliferation, either benign (noncancerous) or malignant (cancerous) including pre-cancerous lesions.

"Metastasis" as used herein refers to the process by which a cancer spreads or transfers from the site of origin to other regions of the body with the development of a similar cancerous lesion at the new location. A "metastatic" or "metastasizing" cell is one that loses adhesive contacts with neighboring cells and migrates via the bloodstream or lymph from the primary site of disease to invade neighboring body structures.

The terms "cancer stem cell", "tumor stem cell", or "solid tumor stem cell" are used interchangeably herein and refer to a population of cells from a solid tumor that: (1) have extensive proliferative capacity; 2) are capable of asymmetric cell division to generate one or more kinds of differentiated progeny with reduced proliferative or developmental potential; and (3) are capable of symmetric cell divisions for self-renewal or self-maintenance. These properties of "cancer stem cells", "tumor stem cells" or "solid tumor stem cells" confer on those cancer stem cells the ability to form palpable tumors upon serial transplantation into an immunocompromised mouse compared to the majority of tumor cells that fail to form tumors. Cancer stem cells undergo self-renewal versus differentiation in a chaotic manner to form tumors with abnormal cell types that can change over time as mutations occur. Solid tumor stem cells differ from the "cancer stem line" provided by U.S. Pat. No. 6,004,528. In that patent, the "cancer stem line" is defined as a slow growing progenitor cell type that itself has few mutations but which undergoes symmetric rather than asymmetric cell divisions as a result of tumorigenic changes that occur in the cell's environment. This "cancer stem line" hypothesis thus proposes that highly mutated, rapidly proliferating tumor cells arise largely as a result of an abnormal environment, which causes relatively normal stem cells to accumulate and then undergo mutations that cause them to become tumor cells. U.S. Pat. No. 6,004,528 proposes that such a model can be used to enhance the diagnosis of cancer. The solid tumor stem cell model is fundamentally different from the "cancer stem line" model and as a result exhibits utilities not offered by the "cancer stem line" model. First, solid tumor stem cells are not "mutationally spared". The "mutationally spared cancer stem line" described by U.S. Pat. No. 6,004,528 can be considered a pre-cancerous lesion, while solid tumor stem cells are cancer cells that may themselves contain the mutations that are responsible for tumorigenesis starting at the pre-cancerous stage through later stage cancer. That is, solid tumor stem cells ("cancer stem cells") would be included among the highly mutated cells that are distinguished from the "cancer stem line" in U.S. Pat. No. 6,004,528. Second, the genetic mutations that lead to cancer can be largely intrinsic within the solid tumor stem cells as well as being environmental. The solid tumor stem cell model predicts that isolated solid tumor stem cells can give rise to additional tumors upon transplantation (thus explaining metastasis) while the "cancer stem line" model would predict that transplanted "cancer stem line" cells would not be able to give rise to a new tumor, since it was their abnormal environment that was tumorigenic. Indeed, the ability to transplant dissociated, and phenotypically isolated human solid tumor stem cells to mice (into an environment that is very different from the normal tumor environment) where they still form new tumors distinguishes the present invention from the "cancer stem line" model. Third, solid tumor stem cells likely divide both symmetrically and asymmetrically, such that symmetric cell division is not an obligate property. Fourth, solid tumor stem cells can divide rapidly or slowly, depending on many variables, such that a slow proliferation rate is not a defining characteristic.

The terms "cancer cell", "tumor cell" and grammatical equivalents refer to the total population of cells derived from a tumor or a pre-cancerous lesion including both non-tumorigenic cells, which comprise the bulk of the tumor cell population, and tumorigenic stem cells (cancer stem cells).

As used herein "tumorigenic" refers to the functional features of a solid tumor stem cell including the properties of self-renewal (giving rise to additional tumorigenic cancer stem cells) and proliferation to generate all other tumor cells (giving rise to differentiated and thus non-tumorigenic tumor cells) that allow solid tumor stem cells to form a tumor.

As used herein, the terms "stem cell cancer marker(s)", "cancer stem cell marker(s)", "tumor stem cell marker(s)", or "solid tumor stem cell marker(s)" refer to a gene or genes or a protein, polypeptide, or peptide expressed by the gene or genes whose expression level, alone or in combination with other genes, is correlated with the presence of tumorigenic cancer cells compared to non-tumorigenic cells. The correlation can relate to either an increased or decreased expression of the gene (e.g. increased or decreased levels of mRNA or the peptide encoded by the gene).

As used herein, the terms "biopsy" or "biopsy tissue" refer to a sample of tissue or fluid that is removed from a subject for the purpose of determining if the sample contains cancerous tissue. In some embodiments, biopsy tissue or fluid is obtained because a subject is suspected of having cancer, and the biopsy tissue or fluid is then examined for the presence or absence of cancer.

As used herein, the term "subject" refers to any animal (e.g., a mammal), including, but not limited to humans, non-human primates, rodents, and the like, which is to be the recipient of a particular treatment. Typically, the terms "subject" and "patient" are used interchangeably herein in reference to a human subject.

"Pharmaceutically acceptable" refers to approved or approvable by a regulatory agency of the Federal or a state government or listed in the U.S. Pharmacopeia or other generally recognized pharmacopeia for use in animals, including humans.

"Pharmaceutically acceptable salt" refers to a salt of a compound that is pharmaceutically acceptable and that possesses the desired pharmacological activity of the parent compound.

"Pharmaceutically acceptable excipient, carrier or adjuvant" refers to an excipient, carrier or adjuvant that can be administered to a subject, together with at least one antibody of the present disclosure, and which does not destroy the pharmacological activity thereof and is nontoxic when administered in doses sufficient to deliver a therapeutic amount of the compound.

"Pharmaceutically acceptable vehicle" refers to a diluent, adjuvant, excipient, or carrier with which at least one antibody of the present disclosure is administered.

"Prodrug" refers to a derivative of a therapeutically effective compound that requires a transformation within the body to produce the therapeutically effective compound. Prodrugs can be pharmacologically inactive until converted to the therapeutically effective parent compound.

The term "therapeutically effective amount" refers to an amount of an antibody, polypeptide, polynucleotide, small organic molecule, or other drug effective to "treat" a disease or disorder in a subject or mammal. In the case of cancer, the therapeutically effective amount of the drug can reduce the number of cancer cells; reduce the tumor size; inhibit or stop cancer cell infiltration into peripheral organs including, for example, the spread of cancer into soft tissue and bone; inhibit and stop tumor metastasis; inhibit and stop tumor growth; relieve to some extent one or more of the symptoms associated with the cancer, reduce morbidity and mortality; improve quality of life; or a combination of such effects. To the extent the drug prevents growth and/or kills existing cancer cells, it can be referred to as cytostatic and/or cytotoxic.

As used herein, "providing a diagnosis" or "diagnostic information" refers to any information, including for example the presence of cancer stem cells, that is useful in determining whether a patient has a disease or condition and/or in classifying the disease or condition into a phenotypic category or any category having significance with regards to the prognosis of or likely response to treatment (either treatment in general or any particular treatment) of the disease or condition. Similarly, diagnosis refers to providing any type of diagnostic information, including, but not limited to, whether a subject is likely to have a condition (such as a tumor), whether a subject's tumor comprises cancer stem cells, information related to the nature or classification of a tumor as for example a high risk tumor or a low risk tumor, information related to prognosis and/or information useful in selecting an appropriate treatment. Selection of treatment can include the choice of a particular chemotherapeutic agent or other treatment modality such as surgery or radiation or a choice about whether to withhold or deliver therapy.

As used herein, the terms "providing a prognosis", "prognostic information", or "predictive information" refer to providing information, including for example the presence of cancer stem cells in a subject's tumor, regarding the impact of the presence of cancer (e.g., as determined by the diagnostic methods of the present invention) on a subject's future health (e.g., expected morbidity or mortality, the likelihood of getting cancer, and the risk of metastasis).

Terms such as "treating" or "treatment" or "to treat" or "alleviating" or "to alleviate" refer to both 1) therapeutic measures that cure, slow down, lessen symptoms of, and/or halt progression of a diagnosed pathologic condition or disorder and 2) prophylactic or preventative measures that prevent and/or slow the development of a targeted pathologic condition or disorder. Thus those in need of treatment include those already with the disorder; those prone to have the disorder; and those in whom the disorder is to be prevented. A subject is successfully "treated" according to the methods of the present invention if the patient shows one or more of the following: a reduction in the number of or complete absence of cancer cells; a reduction in the tumor size; inhibition of or an absence of cancer cell infiltration into peripheral organs including, for example, the spread of cancer into soft tissue and bone; inhibition of or an absence of tumor metastasis; inhibition or an absence of tumor growth; relief of one or more symptoms associated with the specific cancer; reduced morbidity and mortality; improvement in quality of life; or some combination of effects.

As used herein, the terms "polynucleotide" or "nucleic acid" refer to a polymer composed of a multiplicity of nucleotide units (ribonucleotide or deoxyribonucleotide or related structural variants) linked via phosphodiester bonds, including but not limited to, DNA or RNA. The term encompasses sequences that include any of the known base analogs of DNA and RNA, including, but not limited to, 4 acetylcytosine, 8-hydroxy-N6-methyladenosine, aziridinylcytosine, pseudoisocytosine, 5 (carboxyhydroxylmethyl) uracil, 5-fluorouracil, 5 bromouracil, 5-carboxymethylaminomethyl 2 thiouracil, 5 carboxymethylaminomethyluracil, dihydrouracil, inosine, N6 isopentenyladenine, 1 methyladenine, 1-methylpseudouracil, 1 methylguanine, 1 methylinosine, 2,2-dimethylguanine, 2 methyladenine, 2 methylguanine, 3-methylcytosine, 5 methylcytosine, N6 methyladenine, 7 methylguanine, 5 methylaminomethyluracil, 5-methoxyaminomethyl 2 thiouracil, beta D mannosylqueosine, 5' methoxycarbonylmethyluracil, 5 methoxyuracil, 2 methylthio N6 isopentenyladenine, uracil 5 oxyacetic acid methylester, uracil 5 oxyacetic acid, oxybutoxosine, pseudouracil, queosine, 2 thiocytosine, 5-methyl-2 thiouracil, 2-thiouracil, 4 thiouracil, 5-methyluracil, N-uracil 5 oxyacetic acid methylester, uracil 5 oxyacetic acid, pseudouracil, queosine, 2-thiocytosine, and 2,6 diaminopurine.

The phrase "stringent hybridization conditions" refers to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Probes, "Overview of principles of hybridization and the strategy of nucleic acid assays" (1993). Generally, stringent conditions are selected to be about 5-10° C. lower than the thermal melting point (Tm) for the specific sequence at a defined ionic strength pH. The Tm is the temperature (under defined ionic strength, pH, and nucleic concentration) at which 50% of the probes complementary to the target hybridize to the target sequence at equilibrium (as the target sequences are present in excess, at Tm, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

The term "gene" refers to a nucleic acid (e.g., DNA) sequence that comprises coding sequences necessary for the production of a polypeptide, precursor, or RNA (e.g., rRNA, tRNA). The polypeptide can be encoded by a full length coding sequence or by any portion of the coding sequence so long as the desired activity or functional properties (e.g., enzymatic activity, ligand binding, signal transduction, immunogenicity, etc.) of the full-length or fragment are retained. The term also encompasses the coding region of a structural gene and the sequences located adjacent to the coding region on both the 5' and 3' ends for a distance of about 1 kb or more on either end such that the gene corresponds to the length of the full-length mRNA. Sequences located 5' of the coding region and present on the mRNA are referred to as 5' non-translated sequences. Sequences located 3' or downstream of the coding region and present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns can contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide. In addition to containing introns, genomic forms of a gene can also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region can contain regulatory sequences such as promoters and enhancers that control or influence the transcription of the gene. The 3' flanking region can contain sequences that direct the termination of transcription, post transcriptional cleavage and polyadenylation.

The term "recombinant" when used with reference to a cell, nucleic acid, protein or vector indicates that the cell, nucleic acid, protein or vector has been modified by the introduction of a heterologous nucleic acid or protein, the alteration of a native nucleic acid or protein, or that the cell is derived from a cell so modified. Thus, e.g., recombinant cells express genes that are not found within the native (non-recombinant) form of the cell or express native genes that are overexpressed or otherwise abnormally expressed such as, for example, expressed as non-naturally occurring fragments or splice variants. By the term "recombinant nucleic acid"

herein is meant nucleic acid, originally formed in vitro, in general, by the manipulation of nucleic acid, e.g., using polymerases and endonucleases, in a form not normally found in nature. In this manner, operably linkage of different sequences is achieved. Thus an isolated nucleic acid, in a linear form, or an expression vector formed in vitro by ligating DNA molecules that are not normally joined, are both considered recombinant for the purposes of this invention. It is understood that once a recombinant nucleic acid is made and introduced into a host cell or organism, it will replicate non-recombinantly, i.e., using the in vivo cellular machinery of the host cell rather than in vitro manipulations; however, such nucleic acids, once produced recombinantly, although subsequently replicated non-recombinantly, are still considered recombinant for the purposes of the invention. Similarly, a "recombinant protein" is a protein made using recombinant techniques, i.e., through the expression of a recombinant nucleic acid as depicted above.

As used herein, the term "heterologous gene" refers to a gene that is not in its natural environment. For example, a heterologous gene includes a gene from one species introduced into another species. A heterologous gene also includes a gene native to an organism that has been altered in some way (e.g., mutated, added in multiple copies, linked to non-native regulatory sequences, etc). Heterologous genes are distinguished from endogenous genes in that the heterologous gene sequences are typically joined to DNA sequences that are not found naturally associated with the gene sequences in the chromosome or are associated with portions of the chromosome not found in nature (e.g., genes expressed in loci where the gene is not normally expressed).

As used herein, the term "vector" is used in reference to nucleic acid molecules that transfer DNA segment(s) from one cell to another. The term "vehicle" is sometimes used interchangeably with "vector." Vectors are often derived from plasmids, bacteriophages, or plant or animal viruses.

"Ligation" refers to the process of forming phosphodiester bonds between two double stranded nucleic acid fragments. Unless otherwise provided, ligation can be accomplished using known buffers and conditions with 10 units to T4 DNA ligase ("ligase") per 0.5 ug of approximately equimolar amounts of the DNA fragments to be ligated. Ligation of nucleic acid can serve to link two proteins together in-frame to produce a single protein, or fusion protein.

As used herein, the term "gene expression" refers to the process of converting genetic information encoded in a gene into RNA (e.g., mRNA, rRNA, tRNA, or snRNA) through "transcription" of the gene (e.g., via the enzymatic action of an RNA polymerase), and for protein encoding genes, into protein through "translation" of mRNA. Gene expression can be regulated at many stages in the process. "Up-regulation" or "activation" refers to regulation that increases the production of gene expression products (e.g., RNA or protein), while "down-regulation" or "repression" refers to regulation that decrease production. Molecules (e.g., transcription factors) that are involved in up-regulation or down-regulation are often called "activators" and "repressors," respectively.

The terms "polypeptide," "peptide," "protein," and "protein fragment" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers.

The term "amino acid" refers to naturally occurring and synthetic amino acids, as well as amino acid analogs and amino acid mimetics that function similarly to the naturally occurring amino acids. Naturally occurring amino acids are those encoded by the genetic code, as well as those amino acids that are later modified, e.g., hydroxyproline, gamma-carboxyglutamate, and O-phosphoserine. Amino acid analogs refers to compounds that have the same basic chemical structure as a naturally occurring amino acid, e.g., an alpha carbon that is bound to a hydrogen, a carboxyl group, an amino group, and an R group, e.g., homoserine, norleucine, methionine sulfoxide, methionine methyl sulfonium. Such analogs can have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions similarly to a naturally occurring amino acid.

"Conservatively modified variants" applies to both amino acid and nucleic acid sequences. "Amino acid variants" refers to amino acid sequences. With respect to particular nucleic acid sequences, conservatively modified variants refers to those nucleic acids which encode identical or essentially identical amino acid sequences, or where the nucleic acid does not encode an amino acid sequence, to essentially identical or associated (e.g., naturally contiguous) sequences. Because of the degeneracy of the genetic code, a large number of functionally identical nucleic acids encode most proteins. For instance, the codons GCA, GCC, GCG and GCU all encode the amino acid alanine. Thus, at every position where an alanine is specified by a codon, the codon can be altered to another of the corresponding codons described without altering the encoded polypeptide. Such nucleic acid variations are "silent variations," which are one species of conservatively modified variations. Every nucleic acid sequence herein which encodes a polypeptide also describes silent variations of the nucleic acid. One of skill will recognize that in certain contexts each codon in a nucleic acid (except AUG, which is ordinarily the only codon for methionine, and TGG, which is ordinarily the only codon for tryptophan) can be modified to yield a functionally identical molecule. Accordingly, silent variations of a nucleic acid which encodes a polypeptide is implicit in a described sequence with respect to the expression product, but not with respect to actual probe sequences. As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" including where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention. Typically conservative substitutions include: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

The term "epitope tagged" as used herein refers to a chimeric polypeptide comprising a cancer stem cell marker protein, or a domain sequence or portion thereof, fused to an "epitope tag". The epitope tag polypeptide comprises enough amino acid residues to provide an epitope for recognition by an antibody, yet is short enough such that it does not interfere with the activity of the cancer stem cell marker protein. Suitable epitope tags generally have at least six amino acid residues, usually between about 8 to about 50 amino acid residues, and at times between about 10 to about 20 residues. Commonly used epitope tags include Fc, HA, His, and FLAG tags.

The present invention provides compositions and methods for studying, diagnosing, characterizing, and treating cancer. In particular, the present invention provides antibodies against solid tumor stem cell markers and methods of using these antibodies to inhibit tumor growth and treat cancer in human patients. In certain embodiments, antibodies of the present invention include antagonist antibodies that specifically bind to a cancer stem cell marker protein and interfere with, for example, ligand binding, receptor dimerization, expression of a cancer stem cell marker protein, and/or signaling of a cancer stem cell marker protein. In certain embodiments, disclosed antibodies include agonist antibodies that specifically bind to a cancer stem cell marker protein and promote, for example, ligand binding, receptor dimerization, and/or signaling by a cancer stem cell marker protein. In certain embodiments, disclosed antibodies do not interfere with or promote the biological activity of a cancer stem cell marker protein but inhibit tumor growth by, for example, internalization and/or recognition by the immune system. In certain embodiments, the antibodies specifically recognize more than one solid tumor tem cells marker protein.

Provided is an isolated antibody that specifically binds to a human DLL4 epitope formed by a combination of the human DLL4 N-terminal region (SEQ ID NO: 27) and human DSL (SEQ ID NO: 26), wherein the antibody affects growth of a tumor. In certain embodiments the antibody is a monoclonal antibody. In certain embodiments the antibody is a chimeric antibody. In certain embodiments the antibody is a humanized antibody. In certain embodiments the antibody is a human antibody. Further provided is a pharmaceutical composition comprising an antibody of the present disclosure and a pharmaceutically acceptable vehicle.

Further provided is a method of treating cancer comprising administering an therapeutically effective amount of an antibody or a pharmaceutical composition of the present disclosure. In certain embodiments the antibody is conjugated to a cytotoxic moiety. In certain embodiments the method further comprises administering at least one additional therapeutic agent appropriate for effecting combination therapy. In certain embodiments the tumor cells are chosen from a breast tumor, colorectal tumor, lung tumor, prostate tumor, pancreatic tumor, and a head and neck tumor.

Like the tissues in which they originate, solid tumors consist of a heterogeneous population of cells. That the majority of these cells lack tumorigenicity suggested that the development and maintenance of solid tumors also relies on a small population of stem cells (i.e., tumorigenic cancer cells) with the capacity to proliferate and efficiently give rise both to additional tumor stem cells (self-renewal) and to the majority of more differentiated tumor cells that lack tumorigenic potential (i.e., non-tumorigenic cancer cells). The concept of cancer stem cells was first introduced soon after the discovery of hematopoietic stem cells (HSC) and was established experimentally in acute myelogenous leukemia (AML) (Park et al., 1971, *J. Natl. Cancer Inst.* 46:411-22; Lapidot et al., 1994, *Nature* 367:645-8; Bonnet & Dick, 1997, *Nat. Med.* 3:730-7; Hope et al., 2004, *Nat. Immunol.* 5:738-43). Stem cells from solid tumors have more recently been isolated based on their expression of a unique pattern of cell-surface receptors and on the assessment of their properties of self-renewal and proliferation in culture and in xenograft animal models. An ESA+CD44+CD24−/low Lineage-population greater than 50-fold enriched for the ability to form tumors relative to unfractionated tumor cells was discovered (Al-Hajj et al., 2003, *Proc. Nat'l. Acad. Sci.* 100:3983-8). The ability to isolate tumorigenic cancer stem cells from the bulk of non-tumorigenic tumor cells has led to the identification of cancer stem cell markers, genes with differential expression in cancer stem cells compared to non-tumorigenic tumor cells or normal breast epithelium, using microarray analysis. The present invention employs the knowledge of these identified cancer stem cell markers to diagnosis and treat cancer.

The cancer stem cell markers of the present invention relate to human DLL4, a Notch receptor ligand. The Notch signaling pathway is one of several critical regulators of embryonic pattern formation, post-embryonic tissue maintenance, and stem cell biology. More specifically, Notch signaling is involved in the process of lateral inhibition between adjacent cell fates and plays an important role in cell fate determination during asymmetric cell divisions. Unregulated Notch signaling is associated with numerous human cancers where it can alter the developmental fate of tumor cells to maintain them in an undifferentiated and proliferative state (Brennan and Brown, 2003, *Breast Cancer Res.* 5:69). Thus carcinogenesis can proceed by usurping homeostatic mechanisms controlling normal development and tissue repair by stem cell populations (Beachy et al., 2004, *Nature* 432:324).

The Notch receptor was first identified in *Drosophila* mutants. Haploinsufficiency of *Drosophila* Notch results in notches at the wing margin whereas loss-of-function produces an embryonic lethal "neurogenic" phenotype where cells of the epidermis switch fate to neural tissue (Moohr, 1919, Genet. 4:252; Poulson, 1937, *PNAS* 23:133; Poulson, 1940, *J. Exp. Zool.* 83:271). The Notch receptor is a single-pass transmembrane receptor containing numerous tandem epidermal growth factor (EGF)-like repeats and cysteine-rich Notch/LIN-12 repeats within a large extracellular domain (Wharton et al., 1985, *Cell* 43:567; Kidd et al., 1986, *Mol. Cell. Biol.* 6:3094; reviewed in Artavanis et al., 1999, *Science* 284:770). Four mammalian Notch proteins have been identified (NOTCH1, NOTCH2, NOTCH3, and NOTCH4), and mutations in these receptors invariably result in developmental abnormalities and human pathologies including several cancers as described in detail below (Gridley, 1997, *Mol. Cell. Neurosci.* 9:103; Joutel & Tournier-Lasserve, 1998, *Semin. Cell Dev. Biol.* 9:619-25).

The Notch receptor is activated by single-pass transmembrane ligands of the Delta, Serrated, Lag-2 (DSL) family. The known Notch ligands in mammals, Delta-like 1 (Dll1), Delta-like 3 (Dll3), Delta-like 4 (Dll4), Jagged 1 and Jagged 2, are characterized by a DSL domain and tandem EGF-like repeats within the extracellular domain. The extracellular domain of the Notch receptor interacts with that of its ligands, typically on adjacent cells, resulting in two proteolytic cleaveages of Notch, an extracellular cleavage mediated by an ADAM protease and a cleavage within the transmembrane domain mediated by gamma secretase. This latter cleavage generates the Notch intracellular domain (NICD). The NICD then enters the nucleus where it activates the CBF1, Suppressor of Hairless [Su(H)], Lag-2 (CSL) family of transcription factors as the major downstream effectors to increase transcription of nuclear basic helix-loop-helix transcription factors of the Hairy and Enhancer of Split [E(spl)] family (Artavanis et al., 1999, *Science* 284:770; Brennan and Brown, 2003, *Breast Cancer Res.* 5:69; Iso et al., 2003, *Arterioscler. Thromb. Vasc. Biol.* 23:543). Alternative intracellular pathways involving the cytoplasmic protein Deltex identified in *Drosophila* may also exist in mammals (Martinez et al., 2002, *Curr. Opin. Genet. Dev.* 12:524-33), and this Deltex-dependent pathway may act to suppress expression of Wnt target genes (Brennan et al., 1999, *Curr. Biol.* 9:707-710; Lawrence et al., 2001, *Curr. Biol.* 11:375-85).

Hematopoietic stem cells (HSCs) are the best understood stem cells in the body, and Notch signaling is implicated both in their normal maintenance as well as in leukemic transformation (Kopper & Hajdu, 2004, *Pathol. Oncol. Res.* 10:69-73). HSCs are a rare population of cells that reside in a stomal niche within the adult bone marrow. These cells are characterized both by a unique gene expression profile as well as an ability to continuously give rise to more differentiated progenitor cells to reconstitute the entire hematopoietic system. Constitutive activation of Notch1 signaling in HSCs and progenitor cells establishes immortalized cell lines that generate both lymphoid and myeloid cells in vitro and in long-term reconstitution assays (Varnum-Finney et al., 2000, *Nat. Med.* 6:1278-81), and the presence of Jagged 1 increases engraftment of human bone marrow cell populations enriched for HSCs (Karanu et al., 2000, *J. Exp. Med.* 192:1365-72). More recently, Notch signaling has been demonstrated in HSCs in vivo and shown to be involved in inhibiting HSC differentiation. Furthermore, Notch signaling appears to be required for Wnt-mediated HSC self-renewal (Duncan et al., 2005, *Nat. Immunol.* 6:314).

The Notch signaling pathway also plays a central role in the maintenance of neural stem cells and is implicated both in their normal maintenance as well as in brain cancers (Kopper & Hajdu, 2004, *Pathol. Oncol. Res.* 10:69-73; Purow et al., 2005, *Cancer Res.* 65:2353-63; Hallahan et al., 2004, *Cancer Res.* 64:7794-800). Neural stem cells give rise to all neuronal and glial cells in the mammalian nervous system during development, and more recently have been identified in the adult brain (Gage, 2000, *Science* 287:1433-8). Mice deficient for Notch1; the Notch target genes Hes1, 3, and 5; and a regulator of Notch signaling presenilin1 (PS1) show decreased numbers of embryonic neural stem cells. Furthermore, adult neural stem cells are reduced in the brains of PS1 heterozygote mice (Nakamura et al., 2000, *J. Neurosci.* 20:283-93; Hitoshi et al., 2002, *Genes Dev.* 16:846-58). The reduction in neural stem cells appears to result from their premature differentiation into neurons (Hatakeyama et al., 2004, *Dev.* 131:5539-50) suggesting that Notch signaling regulates neural stem cell differentiation and self-renewal.

Aberrant Notch signaling is implicated in a number of human cancers. The NOTCH1 gene in humans was first identified in a subset of T-cell acute lymphoblastic leukemias as a translocated locus resulting in activation of the Notch pathway (Ellisen et al., 1991, *Cell* 66:649-61). Constitutive activation of Notch1 signaling in T-cells in mouse models similarly generates T-cell lymphomas suggesting a causative role (Robey et al., 1996, *Cell* 87:483-92; Pear et al., 1996, *J. Exp. Med.* 183:2283-91; Yan et al., 2001, *Blood* 98:3793-9; Bellavia et al., 2000, *EMBO J.* 19:3337-48). Recently NOTCH1 point mutations, insertions, and deletions producing aberrant NOTCH1 signaling have been found to be frequently present in both childhood and adult T-cell acute lymphoblastic leukemia/lymphoma (Pear & Aster, 2004, *Curr. Opin. Hematol.* 11:416-33).

The frequent insertion of the mouse mammary tumor virus into both the Notch1 and Notch4 locus in mammary tumors and the resulting activated Notch protein fragments first implicated Notch signaling in breast cancer (Gallahan & Callahan, 1987, *J. Virol.* 61:66-74; Brennan & Brown, 2003, *Breast Cancer Res.* 5:69; Politi et al., 2004, *Semin. Cancer Biol.* 14:341-7). Further studies in transgenic mice have confirmed a role for Notch in ductal branching during normal mammary gland development, and a constitutively active form of Notch4 in mammary epithelial cells inhibits epithelial differentiation and results in tumorigenesis (Jhappan et al., 1992, *Genes & Dev.* 6:345-5; Gallahan et al., 1996, *Cancer Res.* 56:1775-85; Smith et al., 1995, *Cell Growth Differ.* 6:563-77; Soriano et al., 2000, *Int. J. Cancer* 86:652-9; Uyttendaele et al., 1998, *Dev. Biol.* 196:204-17; Politi et al., 2004, *Semin. Cancer Biol.* 14:341-7). Currently the evidence for a role for Notch in human breast cancer is limited to the expression of Notch receptors in breast carcinomas and their correlation with clinical outcome (Weijzen et al., 2002, *Nat. Med.* 8:979-86; Parr et al., 2004, *Int. J. Mol. Med.* 14:779-86). Furthermore, overexpression of the Notch pathway has been observed in cervical cancers (Zagouras et al., 1995, *PNAS* 92:6414-8), renal cell carcinomas (Rae et al., 2000, *Int. J. Cancer* 88:726-32), head and neck squamous cell carcinomas (Leethanakul et al., 2000, *Oncogene* 19:3220-4), endometrial cancers (Suzuki et al., 2000, *Int. J. Oncol.* 17:1131-9), and neuroblastomas (van Limpt et al., 2000, *Med. Pediatr. Oncol.* 35:554-8) indicative of a potential role for Notch in the development of a number of neoplasms. Interestingly, Notch signaling might play a role in the maintenance of the undifferentiated state of Apc-mutant neoplastic cells of the colon (van Es & Clevers, 2005, *Trends Mol. Med.* 11:496-502).

The Notch pathway is also involved in multiple aspects of vascular development including proliferation, migration, smooth muscle differentiation, angiogenesis and arterial-venous differentiation (Iso et al., 2003, *Arterioscler. Thromb. Vasc. Biol.* 23:543). For example, homozygous null mutations in Notch-¼ and Jagged-1 as well as heterozygous loss of Dll4 result in severe though variable defects in arterial development and yolk sac vascularization. Furthermore, Dll1-deficient and Notch-2-hypomorphic mice embryos show hemorrhage that likely results from poor development of vascular structures (Gale et al., 2004, *PNAS*, 101:15949-54; Krebs et al., 2000, *Genes Dev.* 14:1343-52; Xue et al., 1999, *Hum. Mel Genet.* 8:723-30; Hrabe de Angelis et al., 1997, *Nature* 386:717-21; McCright et al., 2001, *Dev.* 128:491-502). In humans, mutations in JAGGED1 are associated with Alagille syndrome, a developmental disorder that includes vascular defects, and mutations in NOTCH3 are responsible for an inherited vascular dementia (CADASIL) in which vessel homeostasis is defective (Joutel et al., 1996, *Nature* 383:707-10).

The identification of DLL4 as expressed in cancer stem cells compared to normal breast epithelium suggested targeting the Notch pathway to eliminate not only the majority of non-tumorigenic cancer cells, but also the tumorigenic cells responsible for the formation and reoccurrence of solid tumors. Furthermore, because of the prominent role of angiogenesis in tumor formation and maintenance, targeting the Notch pathway via antibodies against DLL4 can also effectively inhibit angiogenesis, starving a cancer of nutrients and contributing to its elimination.

Thus, present invention provides a cancer stem cell marker, the expression of which can be analyzed to diagnosis or monitor a disease associated with cancer. In some embodiments, expression of a cancer stem cell marker is determined by polynucleotide expression such as, for example, mRNA encoding the cancer stem cell marker. The polynucleotide can be detected and quantified by any of a number of means well known to those of skill in the art. In some embodiments, mRNA encoding a cancer stem cell marker is detected by in situ hybridization of tissue sections from, for example, a patient biopsy. In some embodiments, RNA is isolated from a tissue and detected by, for example, Northern blot, quantitative RT-PCR, or microarrays. For example, total RNA can be extracted from a tissue sample and primers that specifically hybridize and amplify a cancer stem cell marker can be used to detect expression of a cancer stem cell marker polynucleotide using RT-PCR.

In certain embodiments, expression of a cancer stem cell marker can be determined by detection of the corresponding polypeptide. The polypeptide can be detected and quantified by any of a number of means well known to those of skill in the art. In some embodiments, a cancer stem cell marker polypeptide is detected using analytic biochemical methods such as, for example, electrophoresis, capillary electrophoresis, high performance liquid chromatography (HPLC) or thin layer chromatography (TLC). The isolated polypeptide can also be sequenced according to standard techniques. In some embodiments, a cancer stem cell marker protein is detected with antibodies raised against the protein using, for example, immunofluorescence or immunohistochemistry on tissue sections. Alternatively antibodies against a cancer stem cell marker can detect expression using, for example, ELISA, FACS, Western blot, immunoprecipitation or protein microarrays. For example, cancer stem cells can be isolated from a patient biopsy and expression of a cancer stem cell marker protein detected with fluorescently labeled antibodies using FACS. In another method, the cells expressing a cancer stem cell marker can be detected in vivo using labeled antibodies in typical imaging system. For example, antibodies labeled with paramagnetic isotopes can be used for magnetic resonance imaging (MRI).

In some embodiments of the present invention, a diagnostic assay comprises determining the expression or not of a cancer stem cell marker in tumor cells using, for example, immunohistochemistry, in situ hybridization, or RT-PCR. In other embodiments, a diagnostic assay comprises determining expression levels of a cancer stem cell marker using, for example, quantitative RT-PCR. In some embodiments, a diagnostic assay further comprises determining expression levels of a cancer stem cell marker compared to a control tissue such as, for example, normal epithelium.

Detection of a cancer stem cell marker expression can then be used to provide a prognosis and select a therapy. A prognosis can be based on any known risk expression of a cancer stem cell marker indicates. Furthermore, detection of a cancer stem cell marker can be used to select an appropriate therapy including, for example, treatment with antibodies against the detected cancer stem cell marker protein. In certain embodiments, the antibody specifically binds to the extracellular domain of a cancer stem cell marker protein such as the Notch receptor ligand, DLL4.

In the context of the present invention, a suitable antibody is an agent that can have one or more of the following effects, for example: interfere with the expression of a cancer stem cell marker; interfere with activation of a cancer stem cell signal transduction pathway by, for example, sterically inhibiting interactions between a cancer stem cell marker and its ligand, receptor or co-receptors; activate a cancer stem cell signal transduction pathway by, for example, acting as a ligand or promoting the binding of an endogenous ligand; or bind to a cancer stem cell marker and inhibit tumor cell proliferation.

In certain embodiments, antibodies against a cancer stem cell marker act extracellularly to modulate the function of a cancer stem cell marker protein. In some embodiments, extracellular binding of an antibody against a cancer stem cell marker can inhibit the signaling of a cancer stem cell marker protein by, for example, inhibiting intrinsic activation (e.g. kinase activity) of a cancer stem cell marker and/or by sterically inhibiting the interaction, for example, of a cancer stem cell marker with its ligand, with its receptor, with a co-receptor, or with the extracellular matrix. In some embodiments, extracellular binding of an antibody against a cancer stem cell marker can downregulate cell-surface expression of a cancer stem cell marker such as, for example, by internalization of a cancer stem cell marker protein or decreasing cell surface trafficking of a cancer stem cell marker. In some embodiments, extracellular binding of an antibody against a cancer stem cell marker can promote the signaling of a cancer stem cell marker protein by, for example, acting as a decoy ligand or increasing ligand binding.

In certain embodiments, antibodies against a cancer stem cell marker bind to a cancer stem cell marker protein and have one or more of the following effects inhibit proliferation of tumor cells, trigger cell death of tumor cells, promote differentiation of tumor cells into a less tumorigenic cell type, or prevent metastasis of tumor cells. In certain embodiments, antibodies against a cancer stem cell marker trigger cell death via a conjugated toxin, chemotherapeutic agent, radioisotope, or other such agent. For example, an antibody against a cancer stem cell marker is conjugated to a toxin that is activated in tumor cells expressing the cancer stem cell marker by protein internalization.

In certain embodiments, antibodies against a cancer stem cell marker mediate cell death of a cell expressing the cancer stem cell marker protein via antibody-dependent cellular cytotoxicity (ADCC). ADCC involves cell lysis by effector cells that recognize the Fc portion of an antibody. Many lymphocytes, monocytes, tissue macrophages, granulocytes and eosinophiles, for example, have Fc receptors and can mediate cytolysis (Dillman, 1994, *J. Clin. Oncol.* 12:1497).

In certain embodiments, antibodies against a cancer stem cell marker trigger cell death of a cell expressing a cancer stem cell marker protein by activating complement-dependent cytotoxicity (CDC). CDC involves binding of serum complement to the Fc portion of an antibody and subsequent activation of the complement protein cascade, resulting in cell membrane damage and eventual cell death. Biological activity of antibodies is known to be determined, to a large extent, by the constant domains or Fc region of the antibody molecule (Uananue and Benacerraf, Textbook of Immunology, 2nd Edition, Williams & Wilkins, p. 218 (1984)). Antibodies of different classes and subclasses differ in this respect, as do antibodies of the same subclass but from different species. Of human antibodies, IgM is the most efficient class of antibodies to bind complement, followed by IgG1, IgG3, and IgG2 whereas IgG4 appears quite deficient in activating the complement cascade (Dillman, 1994, *J. Clin. Oncol.* 12:1497; Jefferis et al., 1998, *Immunol. Rev.* 163:59-76). According to the present invention, antibodies of those classes having the desired biological activity are prepared.

The ability of any particular antibody against a cancer stem cell to mediate lysis of the target cell by complement activation and/or ADCC can be assayed. The cells of interest are grown and labeled in vitro; the antibody is added to the cell culture in combination with either serum complement or immune cells which can be activated by the antigen antibody complexes. Cytolysis of the target cells is detected, for example, by the release of label from the lysed cells. In fact, antibodies can be screened using the patient's own serum as a source of complement and/or immune cells. The antibody that is capable of activating complement or mediating ADCC in the in vitro test can then be used therapeutically in that particular patient.

In certain embodiments, antibodies against a cancer stem cell marker can trigger cell death inhibiting angiogenesis.

Angiogenesis is the process by which new blood vessels form from pre-existing vessels and is a fundamental process required for normal growth, for example, during embryonic development, wound healing, and in response to ovulation. Solid tumor growth larger than 1-2 mm$^2$ also requires angiogenesis to supply nutrients and oxygen without which tumor cells die. In certain embodiments, an antibody against a cancer stem cell marker targets vascular cells that express the cancer stem cell marker including, for example, endothelial cells, smooth muscle cells, or components of the extracellular matrix required for vascular assembly. In certain embodiments, an antibody against a cancer stem cell marker inhibits growth factor signaling required by vascular cell recruitment, assembly, maintenance, or survival.

The antibodies against a cancer stem cell marker find use in the diagnostic and therapeutic methods described herein. In certain embodiments, the antibodies of the present invention are used to detect the expression of a cancer stem cell marker protein in biological samples such as, for example, a patient tissue biopsy, pleural effusion, or blood sample. Tissue biopsies can be sectioned and protein detected using, for example, immunofluorescence or immunohistochemistry. In addition, individual cells from a sample can be isolated, and protein expression detected on fixed or live cells by FACS analysis. In certain embodiments, antibodies can be used on protein arrays to detect expression of a cancer stem cell marker, for example, on tumor cells, in cell lysates, or in other protein samples. In certain embodiments, the antibodies of the present invention are used to inhibit the growth of tumor cells by contacting the antibodies with tumor cells in in vitro cell based assays, in vivo animal models, etc. In certain embodiments, the antibodies are used to treat cancer in a patient by administering a therapeutically effective amount of an antibody against a cancer stem cell marker.

The antibodies of the invention can be prepared by any conventional means known in the art. For example, polyclonal antibodies can be prepared by immunizing an animal (e.g. a rabbit, rat, mouse, donkey, etc) by multiple subcutaneous or intraperitoneal injections of the relevant antigen (a purified peptide fragment, full-length recombinant protein, fusion protein, etc) optionally conjugated to keyhole limpet hemocyanin (KLH), serum albumin, etc. diluted in sterile saline and combined with an adjuvant (e.g. Complete or Incomplete Freund's Adjuvant) to form a stable emulsion. The polyclonal antibody is then recovered from blood, ascites and the like, of an animal so immunized. Collected blood is clotted, and the serum decanted, clarified by centrifugation, and assayed for antibody titer. The polyclonal antibodies can be purified from serum or ascites according to standard methods in the art including affinity chromatography, ion-exchange chromatography, gel electrophoresis, dialysis, etc.

Monoclonal antibodies can be prepared using hybridoma methods, such as those described by Kohler and Milstein (1975) *Nature* 256:495. Using the hybridoma method, a mouse, hamster, or other appropriate host animal, is immunized as described above to elicit the production by lymphocytes of antibodies that will specifically bind to an immunizing antigen. Lymphocytes can also be immunized in vitro. Following immunization, the lymphocytes are isolated and fused with a suitable myeloma cell line using, for example, polyethylene glycol, to form hybridoma cells that can then be selected away from unfused lymphocytes and myeloma cells. Hybridomas that produce monoclonal antibodies directed specifically against a chosen antigen as determined by immunoprecipitation, immunoblotting, or by an in vitro binding assay (e.g. radioimmunoassay (RIA); enzyme-linked immunosorbent assay (ELISA)) can then be propagated either in vitro culture using standard methods (Goding, Monoclonal Antibodies: Principles and Practice, Academic Press, 1986) or in vivo as ascites tumors in an animal. The monoclonal antibodies can then be purified from the culture medium or ascites fluid as described for polyclonal antibodies above.

Alternatively monoclonal antibodies can also be made using recombinant DNA methods as described in U.S. Pat. No. 4,816,567. The polynucleotides encoding a monoclonal antibody are isolated from mature B-cells or hybridoma cell, such as by RT-PCR using oligonucleotide primers that specifically amplify the genes encoding the heavy and light chains of the antibody, and their sequence is determined using conventional procedures. The isolated polynucleotides encoding the heavy and light chains are then cloned into suitable expression vectors, which when transfected into host cells such as *E. coli* cells, simian COS cells, Chinese hamster ovary (CHO) cells, or myeloma cells that do not otherwise produce immunoglobulin protein, monoclonal antibodies are generated by the host cells. Also, recombinant monoclonal antibodies or fragments thereof of the desired species can be isolated from phage display libraries expressing CDRs of the desired species as described (McCafferty et al., 1990, *Nature,* 348:552-554; Clackson et al., 1991, *Nature,* 352:624-628; and Marks et al., 1991, *J. Mol. Biol.,* 222:581-597).

The polynucleotide(s) encoding a monoclonal antibody can further be modified in a number of different manners using recombinant DNA technology to generate alternative antibodies. In some embodiments, the constant domains of the light and heavy chains of, for example, a mouse monoclonal antibody can be substituted 1) for those regions of, for example, a human antibody to generate a chimeric antibody or 2) for a non-immunoglobulin polypeptide to generate a fusion antibody. In some embodiments, the constant regions are truncated or removed to generate the desired antibody fragment of a monoclonal antibody. Site-directed or high-density mutagenesis of the variable region can be used to optimize specificity, affinity, etc. of a monoclonal antibody.

In some embodiments of the present invention, the monoclonal antibody against a cancer stem cell marker is a humanized antibody. Humanized antibodies are antibodies that contain minimal sequences from non-human (e.g murine) antibodies within the variable regions. Such antibodies are used therapeutically to reduce antigenicity and HAMA (human anti-mouse antibody) responses when administered to a human subject. In practice, humanized antibodies are typically human antibodies with minimum to no non-human sequences. A human antibody is an antibody produced by a human or an antibody having an amino acid sequence corresponding to an antibody produced by a human.

Humanized antibodies can be produced using various techniques known in the art. An antibody can be humanized by substituting the CDRs of a human antibody with that of a non-human antibody (e.g. mouse, rat, rabbit, hamster, etc.) having the desired specificity, affinity, and capability following the methods of (Jones et al., 1986, *Nature,* 321:522-525; Riechmann et al., 1988, *Nature,* 332:323-327; Verhoeyen et al., 1988, *Science,* 239:1534-1536). The humanized antibody can be further modified by the substitution of additional residue either in the variable human framework region and/or within the replaced non-human residues to refine and optimize antibody specificity, affinity, and/or capability.

The choice of human heavy and/or light chain variable domains to be used in making humanized antibodies can be important for reducing antigenicity. According to the "best-fit" method, the sequence of the variable domain of a rodent antibody is screened against the entire library of known human variable-domain amino acid sequences. Thus in certain embodiments, the human amino acid sequence which is most homologous to that of the rodent antibody from which the CDRs are taken is used as the human framework region (FR) for the humanized antibody (Sims et al., 1993, *J. Immunol.*, 151: 2296; Chothia et al., 1987, *J. Mol. Biol.*, 196: 901). Another method uses a particular FR derived from the consensus sequence of all human antibodies of a particular subgroup of light or heavy chains and can be used for several difference humanized antibodies (Carter et al., 1992, *PNAS*, 89; 4285; Presta et al., 1993, *J. Immunol.*, 151: 2623). In certain embodiments, a combination of methods is used to pick the human variable FR to use in generation of humanized antibodies.

It is further understood that antibodies (e.g. rodent) to be humanized must retain high affinity for the antigen as well as other favorable biological properties. To achieve this goal, humanized antibodies can be prepared by a process of analysis of the parental sequence from the rodent antibody to be humanized and the various candidate humanizing sequences. Three-dimensional immunoglobulin models are available and familiar to those skilled in the art. Computer programs can be used to illustrate and display probable three-dimensional conformational structures of selected candidate antibody sequences. Use of such models permits analysis of the likely role of the residues in the function of the antibody to be humanized, i.e., the analysis of residues that influence the ability of the candidate antibody to bind its antigen. In this way, FR residues can be selected and combined from the parental antibody to the recipient humanized antibody so that the desired antibody characteristics are achieved. In general, the residues in the CDRs of the antigen determination region (or hypervariable region) are retained from the parental antibody (e.g. the rodent antibody with the desired antigen binding properties) in the humanized antibody for antigen binding. In certain embodiments, at least one additional residue within the variable FR is retained from the parental antibody in the humanized antibody. In certain embodiments, up to six additional residues within the variable FR are retained from the parental antibody in the humanized antibody.

Amino acids from the variable regions of the mature heavy and light chains of immunoglobulins are designated Hx and Lx respectively, where x is a number designating the position of an amino acid according to the scheme of Kabat, Sequences of Proteins of Immunological Interest, U.S. Department of Health and Human Services, 1987, 1991. Kabat lists many amino acid sequences for antibodies for each subgroup, and lists the most commonly occurring amino acid for each residue position in that subgroup to generate a consensus sequence. Kabat uses a method for assigning a residue number to each amino acid in a listed sequence, and this method for assigning residue numbers has become standard in the field. Kabat's scheme is extendible to other antibodies not included in his compendium by aligning the antibody in question with one of the consensus sequences in Kabat by reference to conserved amino acids. The use of the Kabat numbering system readily identifies amino acids at equivalent positions in different antibodies. For example, an amino acid at the L50 position of a human antibody occupies the equivalent position to an amino acid position L50 of a mouse antibody. Moreover, any two antibody sequences can be uniquely aligned, for example to determine percent identity, by using the Kabat numbering system so that each amino acid in one antibody sequence is aligned with the amino acid in the other sequence that has the same Kabat number. After alignment, if a subject antibody region (e.g., the entire mature variable region of a heavy or light chain) is being compared with the same region of a reference antibody, the percentage sequence identity between the subject and reference antibody regions is the number of positions occupied by the same amino acid in both the subject and reference antibody region divided by the total number of aligned positions of the two regions, with gaps not counted, multiplied by 100 to convert to percentage.

Example 1 below describes the production of exemplary humanized anti-DLL4 antibodies which specifically bind human DLL4, a cancer stem cell marker of the present disclosure (21M18 H9L2, ATCC deposit no. PTA-8427 and 21M18 H7L2, ATCC deposit no. PTA-8425, deposited May 10, 2007 under the terms of the Budapest Treaty with American Type Culture Collection (ATCC), located at 10801 University Blvd., Manassas, Va. 20110-2209). In certain embodiments, the humanized antibodies comprise nonhuman antigen determination regions derived from murine monoclonal antibody 21M18. Specifically, in certain embodiments, one or more of the heavy chain CDRs from the parental rodent antibody, CDR1 (SEQ ID NO: 1), CDR2 (SEQ ID NO: 2; SEQ ID NO: 3; or SEQ ID NO: 4, which vary at Kabat position 52a), and CDR3 (SEQ ID NO: 5) are retained in the humanized 21M18 antibody. In certain embodiments, one or more of the light chain CDRs from the parental rodent antibody, CDR1 (SEQ ID NO: 9), CDR2 (SEQ ID NO: 10), and CDR3 (SEQ ID NO: 11), are retained in the humanized 21M18 antibody. In certain embodiments, the humanized antibodies further comprise at least one FR substitution within either the heavy or light chain human variable region.

In certain embodiments, the present invention provides a humanized antibody which specifically binds to a human DLL4 epitope formed by a combination of the human DLL4 N-terminal region (SEQ ID NO: 27) and human DSL (SEQ ID NO: 26), wherein the antibody affects growth of a tumor. In certain embodiments, the humanized antibody is an intact IgG antibody. In certain embodiments, the humanized antibody is an intact IgG$_2$ antibody. In certain embodiments, the humanized antibody is an antibody fragment. In certain embodiments, the humanized antibody is a Fab fragment.

In certain embodiments, the humanized antibody of the present invention comprises a heavy chain variable (V$_H$) region comprising a nonhuman antigen determination region and a human variable framework region. In certain embodiments, the nonhuman antigen determination region comprises complementarity determination regions (CDRs) of rodent origin. In certain embodiments, the nonhuman antigen determination region comprises CDRs from a mouse antibody. In certain embodiments, the rodent CDRs derive from monoclonal antibody 21M18, wherein 21M18 comprises a heavy chain variable region designated SEQ ID NO: 6. In certain embodiments, wherein the humanized antibody comprises a V$_H$ region comprising an amino acid sequence of (a) CDR1 (SEQ ID NO: 1), CDR2 (SEQ ID NO: 2; SEQ ID NO: 3; or SEQ ID NO: 4), and CDR3 (SEQ ID NO: 5) or (b) SEQ ID NO: 6, SEQ ID NO: 7, or SEQ ID NO: 8.

In certain embodiments, the human heavy chain variable framework region comprises expressed human sequences. In certain embodiments, at least one residue in the human variable framework region is substituted. In certain embodiments, at least one residue in the human heavy chain variable framework region is at a position selected from the group consisting of 16, 20, 27, 28, 38, and 48 based on the Kabat numbering system. In certain embodiments, positions 16, 20, 27, 28, 38, and 48 are substituted based on the Kabat numbering system. In certain embodiments, at least one residue in the human variable framework region is substituted with a residue occupying the corresponding position in an antibody comprising the nonhuman antigen determination region.

In certain embodiments, the human heavy chain variable framework region comprises IGH(V)1-18. In certain embodiments, at least one residue in the human variable framework region is substituted. In certain embodiments, at least one residue in the human heavy chain variable framework region is at a position selected from the group consisting of 20H, 28H, 38H, 48H, and 69H based on the Kabat numbering system. In certain embodiments, positions 20H, 28H, 38H, 48H, and 69H are substituted based on the Kabat numbering system. In certain embodiments, at least one residue in the human variable framework region is substituted with a residue occupying the corresponding position in an antibody comprising the nonhuman antigen determination region.

In certain embodiments, the humanized antibody of the present invention comprises a light chain variable ($V_L$) region comprising a nonhuman antigen determination region and a human variable framework region. In certain embodiments, the nonhuman antigen determination region comprises CDRs of rodent origin. In certain embodiments, the nonhuman antigen determination region comprises CDRs from a mouse antibody. In certain embodiments, the CDRs derive from monoclonal antibody 21M18, wherein 21M18 comprises a $V_L$ region designated SEQ ID NO: 12. In certain embodiments, the $V_L$ region comprises an amino acid sequence of (a) CDR1 (SEQ ID NO: 9), CDR2 (SEQ ID NO: 10), and CDR3 (SEQ ID NO: 11) or (b) SEQ ID NO: 12.

In certain embodiments, the human light chain variable framework region comprises IGK(V)4-1. In certain embodiments, at least one residue in the human light chain variable framework region is substituted. In certain embodiments, at least one residue in the human variable framework region is at a position selected from the group consisting of 22L and 36L based on the Kabat numbering system. In certain embodiments, positions 22L and 36L are substituted based on the Kabat numbering system. In certain embodiments, at least one residue from the human variable framework region is substituted with a residue occupying the corresponding position in an antibody comprising the nonhuman antigen determination region.

In certain embodiments, the antibody of the present invention is an antibody that competes with the antibody 21M18 for specific binding to human DLL4, wherein the 21M18 antibody comprises: (a) a heavy chain with a variable region designated SEQ ID NO: 6, SEQ ID NO: 7, or SEQ ID NO: 8 and (b) a light chain with a variable region designated SEQ ID NO: 12. In certain embodiments, the antibody is a humanized antibody or a human antibody.

In certain embodiments, the humanized antibody that specifically binds to a human DLL4 epitope formed by a combination of the human DLL4 N-terminal region (SEQ ID NO: 27) and human DSL domain (SEQ ID NO: 26), wherein the antibody comprises a heavy chain variable region having at least 90% sequence identity to SEQ ID NO: 6, SEQ ID NO: 7, or SEQ ID NO: 8 and a light chain variable region having at least 90% sequence identity to SEQ ID NO: 12. In some embodiments, the heavy chain variable region has at least 95% sequence identity to SEQ ID NO: 6, SEQ ID NO: 7, or SEQ ID NO: 8 and the light chain variable region has at least 95% sequence identity to SEQ ID NO: 12. In some embodiments, the heavy chain variable region has at least 99% sequence identity to SEQ ID NO: 6, SEQ ID NO: 7, or SEQ ID NO: 8 and the light chain variable region has at least 99% sequence identity to SEQ ID NO: 12.

In certain embodiments, the present invention provides an isolated polynucleotide molecule encoding a humanized antibody that specifically binds to a human DLL4 epitope formed by a combination of the human DLL4 N-terminal region (SEQ ID NO: 27) and human DSL (SEQ ID NO: 26), wherein the antibody comprises a $V_H$ region that comprises a nonhuman antigen determination region encoding CDR1 (SEQ ID NO: 1); CDR2 (SEQ ID NO: 2, SEQ ID NO: 3, or SEQ ID NO: 4); and CDR3 (SEQ ID NO: 5) and a human variable framework region encoding IGH(V)1-18. In certain embodiments, the present invention provides an isolated polynucleotide molecule encoding a humanized antibody that specifically binds to a human DLL4 epitope formed by a combination of the human DLL4 N-terminal region (SEQ ID NO: 27) and human DSL (SEQ ID NO: 26), wherein the polynucleotide molecule is selected from the group consisting of: (a) a polynucleotide molecule encoding the amino acid sequence of SEQ ID NO: 6, SEQ ID NO: 7, or SEQ ID NO: 8 and (b) a polynucleotide molecule which hybridizes to the complement of the polynucleotide molecule according to (a) under stringent hybridization conditions. In certain embodiments, the present invention provides an isolated polynucleotide molecule encoding a humanized antibody that specifically binds to a human DLL4 epitope formed by a combination of the human DLL4 N-terminal region (SEQ ID NO: 27) and human DSL (SEQ ID NO: 26), wherein the polynucleotide molecule is selected from the group consisting of (a) SEQ ID NO: 13, SEQ ID NO: 14, or SEQ ID NO: 15 and (b) a polynucleotide molecule which hybridizes to the complement of the polynucleotide molecule according to (a) under stringent hybridization conditions.

In certain embodiments, the present invention provides an isolated polynucleotide molecule encoding a humanized antibody that specifically binds to a human DLL4 epitope formed by a combination of the human DLL4 N-terminal region (SEQ ID NO: 27) and human DSL (SEQ ID NO: 26), wherein the antibody comprises a $V_L$ region that comprises a nonhuman antigen determination region encoding CDR1 (SEQ ID NO: 9); CDR2 (SEQ ID NO: 10); and CDR3 (SEQ ID NO: 11) and a human variable framework region comprising IGK(V)4-1. In certain embodiments, the present invention provides an isolated polynucleotide molecule encoding a humanized antibody that specifically binds to a human DLL4 epitope formed by a combination of the human DLL4 N-terminal region (SEQ ID NO: 27) and human DSL (SEQ ID NO: 26), wherein the polynucleotide molecule is selected from the group consisting of: (a) a polynucleotide molecule encoding the amino acid sequence of SEQ ID NO: 12 and (b) a polynucleotide molecule which hybridizes to the complement of the polynucleotide molecule according to (a) under stringent hybridization conditions. In certain embodiments, the present invention provides an isolated polynucleotide molecule encoding a humanized antibody that specifically binds to a human DLL4 epitope formed by a combination of the human DLL4 N-terminal region (SEQ ID NO: 27) and human DSL (SEQ ID NO: 26), wherein the polynucleotide molecule is selected from the group consisting of (a) SEQ ID NO: 16 and (b) a polynucleotide molecule which hybridizes to the complement of the polynucleotide molecule according to (a) under stringent hybridization conditions.

In certain embodiments is provided an expression vector comprising an isolated polynucleotide molecule of the present invention. In certain embodiments is provided a host cell comprising an expression vector comprising an isolated polynucleotide molecule of the present invention.

In certain embodiments, the present invention provides a method of treating cancer in a patient comprising administering to the patient a therapeutically effective amount of a humanized antibody of the present disclosure. In certain embodiments, the cancer comprises breast cancer, colorectal cancer, lung cancer, pancreatic cancer, prostate cancer, or head and neck cancer.

In certain embodiments, the present invention provides a kit comprising a container and a composition contained therein, wherein the composition comprises a humanized antibody of the present disclosure, and further comprises a package insert indicating that the composition can be used to treat cancer.

In addition, fully human antibodies can be directly prepared using various techniques known in the art. Immortalized human B lymphocytes immunized in vitro or isolated from an immunized individual that produce an antibody directed against a target antigen can be generated (See, e.g., Cole et al., Monoclonal Antibodies and Cancer Therapy, Alan R. Liss, p. 77 (1985); Boerner et al., 1991, *J. Immunol.*, 147 (1):86-95; and U.S. Pat. No. 5,750,373). Also, the human antibody can be selected from a phage library, where that phage library expresses human antibodies (Vaughan et al., 1996, *Nat. Biotech.*, 14:309-314; Sheets et al., 1998, *Proc. Nat'l. Acad. Sci.*, 95:6157-6162; Hoogenboom and Winter, 1991, *J. Mol. Biol.*, 227:381; Marks et al., 1991, *J. Mol. Biol.*, 222:581). Human antibodies can also be made in transgenic mice containing human immunoglobulin loci that are capable upon immunization of producing the full repertoire of human antibodies in the absence of endogenous immunoglobulin production. This approach is described in U.S. Pat. Nos. 5,545,807; 5,545,806; 5,569,825; 5,625,126; 5,633,425; and 5,661,016.

This invention also encompasses bispecific antibodies that specifically recognize a cancer stem cell marker. Bispecific antibodies are antibodies that are capable of specifically recognizing and binding at least two different epitopes. The different epitopes can either be within the same molecule (e.g. the same cancer stem cell marker polypeptide) or on different molecules such that both, for example, the antibodies can specifically recognize and bind a cancer stem cell marker as well as, for example, 1) an effector molecule on a leukocyte such as a T-cell receptor (e.g. CD3) or Fc receptor (e.g. CD64, CD32, or CD16) or 2) a cytotoxic agent as described in detail below. Bispecific antibodies can be intact antibodies or antibody fragments.

Exemplary bispecific antibodies can bind to two different epitopes, at least one of which originates in a polypeptide of the invention. Alternatively, an anti-antigenic arm of an immunoglobulin molecule can be combined with an arm which binds to a triggering molecule on a leukocyte such as a T cell receptor molecule (e.g. CD2, CD3, CD28, or B7), or Fc receptors for IgG so as to focus cellular defense mechanisms to the cell expressing the particular antigen. Bispecific antibodies can also be used to direct cytotoxic agents to cells which express a particular antigen. These antibodies possess an antigen-binding arm and an arm which binds a cytotoxic agent or a radionuclide chelator, such as EOTUBE, DPTA, DOTA, or TETA. Techniques for making bispecific antibodies are common in the art (Millstein et al., 1983, *Nature* 305:537-539; Brennan et al., 1985, *Science* 229:81; Suresh et al, 1986, *Methods in Enzymol.* 121:120; Traunecker et al., 1991, *EMBO J.* 10:3655-3659; Shalaby et al., 1992, *J. Exp. Med.* 175:217-225; Kostelny et al., 1992, *J. Immunol.* 148: 1547-1553; Gruber et al., 1994, *J. Immunol.* 152:5368; and U.S. Pat. No. 5,731,168). Antibodies with more than two valencies are also contemplated. For example, trispecific antibodies can be prepared (Tutt et al., *J. Immunol.* 147:60 (1991))

In certain embodiments are provided an antibody fragment to, for example, increase tumor penetration. Various techniques are known for the production of antibody fragments: Traditionally, these fragments are derived via proteolytic digestion of intact antibodies (for example Morimoto et al., 1993, Journal of Biochemical and Biophysical Methods 24:107-117; Brennan et al., 1985, *Science,* 229:81). In certain embodiments, antibody fragments are produced recombinantly. Fab, Fv, and scFv antibody fragments can all be expressed in and secreted from *E. coli* or other host cells, thus allowing the production of large amounts of these fragments. Such antibody fragments can also be isolated from the antibody phage libraries discussed above. The antibody fragment can also be linear antibodies as described in U.S. Pat. No. 5,641,870, for example, and can be monospecific or bispecific. Other techniques for the production of antibody fragments will be apparent to the skilled practitioner.

According to the present invention, techniques can be adapted for the production of single-chain antibodies specific to a polypeptide of the invention (see U.S. Pat. No. 4,946, 778). In addition, methods can be adapted for the construction of Fab expression libraries (Huse, et al., *Science* 246:1275-1281 (1989)) to allow rapid and effective identification of monoclonal Fab fragments with the desired specificity for the Notch receptor ligand DLL4, or derivatives, fragments, or homologs thereof. Antibody fragments that contain the idiotypes to a polypeptide of the invention may be produced by techniques in the art including, but not limited to: (a) an F(ab')2 fragment produced by pepsin digestion of an antibody molecule; (b) an Fab fragment generated by reducing the disulfide bridges of an F(ab')2 fragment, (c) an Fab fragment generated by the treatment of the antibody molecule with papain and a reducing agent, and (d) Fv fragments.

It can further be desirable, especially in the case of antibody fragments, to modify an antibody in order to increase its serum half-life. This can be achieved, for example, by incorporation of a salvage receptor binding epitope into the antibody fragment by mutation of the appropriate region in the antibody fragment or by incorporating the epitope into a peptide tag that is then fused to the antibody fragment at either end or in the middle (e.g., by DNA or peptide synthesis).

Heteroconjugate antibodies are also within the scope of the present invention. Heteroconjugate antibodies are composed of two covalently joined antibodies. Such antibodies have, for example, been proposed to target immune cells to unwanted cells (U.S. Pat. No. 4,676,980). It is contemplated that the antibodies can be prepared in vitro using known methods in synthetic protein chemistry, including those involving crosslinking agents. For example, immunotoxins can be constructed using a disulfide exchange reaction or by forming a thioether bond. Examples of suitable reagents for this purpose include iminothiolate and methyl-4-mercaptobutyrimidate.

For the purposes of the present invention, it should be appreciated that modified antibodies can comprise any type of variable region that provides for the association of the antibody with the polypeptides of human DLL4. In this regard, the variable region may comprise or be derived from any type of mammal that can be induced to mount a humoral response and generate immunoglobulins against the desired tumor associated antigen. As such, the variable region of the modified antibodies can be, for example, of human, murine, non-human primate (e.g. cynomolgus monkeys, macaques, etc.) or lupine origin. In some embodiments both the variable and constant regions of the modified immunoglobulins are human. In other embodiments the variable regions of compatible antibodies (usually derived from a non-human source) can be engineered or specifically tailored to improve the binding properties or reduce the immunogenicity of the molecule. In this respect, variable regions useful in the present invention can be humanized or otherwise altered through the inclusion of imported amino acid sequences.

The variable domains in both the heavy and light chains are altered by at least partial replacement of one or more CDRs and, if necessary, by partial framework region replacement and sequence changing. Although the CDRs may be derived from an antibody of the same class or even subclass as the antibody from which the framework regions are derived, it is envisaged that the CDRs will be derived from an antibody of different class and preferably from an antibody from a different species. It may not be necessary to replace all of the CDRs with the complete CDRs from the donor variable region to transfer the antigen binding capacity of one variable domain to another. Rather, it may only be necessary to transfer those residues that are necessary to maintain the activity of the antigen binding site. Given the explanations set forth in U.S. Pat. Nos. 5,585,089, 5,693,761 and 5,693,762, it will be well within the competence of those skilled in the art, either by carrying out routine experimentation or by trial and error testing to obtain a functional antibody with reduced immunogenicity.

Alterations to the variable region notwithstanding, those skilled in the art will appreciate that the modified antibodies of this invention will comprise antibodies, or immunoreactive fragments thereof, in which at least a fraction of one or more of the constant region domains has been deleted or otherwise altered so as to provide desired biochemical characteristics such as increased tumor localization or reduced serum half-life when compared with an antibody of approximately the same immunogenicity comprising a native or unaltered constant region. In some embodiments, the constant region of the modified antibodies will comprise a human constant region. Modifications to the constant region compatible with this invention comprise additions, deletions or substitutions of one or more amino acids in one or more domains. That is, the modified antibodies disclosed herein may comprise alterations or modifications to one or more of the three heavy chain constant domains (CH1, CH2 or CH3) and/or to the light chain constant domain (CL). In some embodiments of the invention modified constant regions wherein one or more domains are partially or entirely deleted are contemplated. In some embodiments the modified antibodies will comprise domain deleted constructs or variants wherein the entire CH2 domain has been removed (ΔCH2 constructs). In some embodiments the omitted constant region domain will be replaced by a short amino acid spacer (e.g. 10 residues) that provides some of the molecular flexibility typically imparted by the absent constant region.

Besides their configuration, it is known in the art that the constant region mediates several effector functions. For example, binding of the C1 component of complement to antibodies activates the complement system. Activation of complement is important in the opsonisation and lysis of cell pathogens. The activation of complement also stimulates the inflammatory response and can also be involved in autoimmune hypersensitivity. Further, antibodies bind to cells via the Fc region, with a Fc receptor site on the antibody Fc region binding to a Fc receptor (FcR) on a cell. There are a number of Fc receptors which are specific for different classes of antibody, including IgG (gamma receptors), IgE (eta receptors), IgA (alpha receptors) and IgM (mu receptors). Binding of antibody to Fc receptors on cell surfaces triggers a number of important and diverse biological responses including engulfment and destruction of antibody-coated particles, clearance of immune complexes, lysis of antibody-coated target cells by killer cells (called antibody-dependent cell-mediated cytotoxicity, or ADCC), release of inflammatory mediators, placental transfer and control of immunoglobulin production. Although various Fc receptors and receptor sites have been studied to a certain extent, there is still much which is unknown about their location, structure and functioning.

While not limiting the scope of the present invention, it is believed that antibodies comprising constant regions modified as described herein provide for altered effector functions that, in turn, affect the biological profile of the administered antibody. For example, the deletion or inactivation (through point mutations or other means) of a constant region domain may reduce Fc receptor binding of the circulating modified antibody thereby increasing tumor localization. In other cases it may be that constant region modifications, consistent with this invention, moderate complement binding and thus reduce the serum half life and nonspecific association of a conjugated cytotoxin. Yet other modifications of the constant region may be used to eliminate disulfide linkages or oligosaccharide moieties that allow for enhanced localization due to increased antigen specificity or antibody flexibility. Similarly, modifications to the constant region in accordance with this invention may easily be made using well known biochemical or molecular engineering techniques well within the purview of the skilled artisan.

It will be noted that the modified antibodies may be engineered to fuse the CH3 domain directly to the hinge region of the respective modified antibodies. In other constructs it may be desirable to provide a peptide spacer between the hinge region and the modified CH2 and/or CH3 domains. For example, compatible constructs could be expressed wherein the CH2 domain has been deleted and the remaining CH3 domain (modified or unmodified) is joined to the hinge region with a 5-20 amino acid spacer. Such a spacer may be added, for instance, to ensure that the regulatory elements of the constant domain remain free and accessible or that the hinge region remains flexible. However, it should be noted that amino acid spacers can, in some cases, prove to be immunogenic and elicit an unwanted immune response against the construct. Accordingly, any spacer added to the construct be relatively non-immunogenic or, even omitted altogether if the desired biochemical qualities of the modified antibodies may be maintained.

Besides the deletion of whole constant region domains, it will be appreciated that the antibodies of the present invention may be provided by the partial deletion or substitution of a few or even a single amino acid. For example, the mutation of a single amino acid in selected areas of the CH2 domain may be enough to substantially reduce Fc binding and thereby increase tumor localization. Similarly, it may be desirable to simply delete that part of one or more constant region domains that control the effector function (e.g. complement CLQ binding) to be modulated. Such partial deletions of the constant regions may improve selected characteristics of the antibody (serum half-life) while leaving other desirable functions associated with the subject constant region domain intact. Moreover, as alluded to above, the constant regions of the disclosed antibodies may be modified through the mutation or substitution of one or more amino acids that enhances the profile of the resulting construct. In this respect it may be possible to disrupt the activity provided by a conserved binding site (e.g. Fc binding) while substantially maintaining the configuration and immunogenic profile of the modified antibody. Certain embodiments can comprise the addition of one or more amino acids to the constant region to enhance desirable characteristics such as effector function or provide for more cytotoxin or carbohydrate attachment. In such embodiments it can be desirable to insert or replicate specific sequences derived from selected constant region domains.

The present invention further embraces variants and equivalents which are substantially homologous to the chimeric, humanized and human antibodies, or antibody fragments thereof, set forth herein. These can contain, for example, conservative substitution mutations, i.e. the substitution of one or more amino acids by similar amino acids. For example, conservative substitution refers to the substitution of an amino acid with another within the same general class such as, for example, one acidic amino acid with another acidic amino acid, one basic amino acid with another basic amino acid or one neutral amino acid by another neutral amino acid. What is intended by a conservative amino acid substitution is well known in the art.

The invention also pertains to immunoconjugates comprising an antibody conjugated to a cytotoxic agent. Cytotoxic agents include chemotherapeutic agents, growth inhibitory agents, toxins (e.g., an enzymatically active toxin of bacterial, fungal, plant, or animal origin, or fragments thereof), radioactive isotopes (i.e., a radioconjugate), etc. Chemotherapeutic agents useful in the generation of such immunoconjugates include, for example, methotrexate, adriamicin, doxorubicin, melphalan, mitomycin C, chlorambucil, daunorubicin or other intercalating agents. Enzymatically active toxins and fragments thereof that can be used include diphtheria A chain, nonbinding active fragments of diphtheria toxin, exotoxin A chain, ricin A chain, abrin A chain, modeccin A chain, alpha-sarcin, Aleurites fordii proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin, and the tricothecenes. In some embodiments, the antibodies can be conjugated to radioisotopes, such as $^{90}Y$, $^{125}I$, $^{131}I$, $^{123}I$, $^{111}In$, $^{105}Rh$, $^{153}Sm$, $^{67}Cu$, $^{67}Ga$, $^{166}Ho$, $^{177}Lu$, $^{186}Re$ and $^{188}Re$ using anyone of a number of well known chelators or direct labeling. In other embodiments, the disclosed compositions can comprise antibodies coupled to drugs, prodrugs or lymphokines such as interferon. Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutaraldehyde), bis-azido compounds (such as bis(p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). Conjugates of an antibody and one or more small molecule toxins, such as a calicheamicin, maytansinoids, a trichothene, and CC1065, and the derivatives of these toxins that have toxin activity, can also be used. In some embodiments, the modified antibodies can be complexed with other immunologically active ligands (e.g. antibodies or fragments thereof) wherein the resulting molecule binds to both the neoplastic cell and an effector cell such as a T cell.

Regardless of how useful quantities are obtained, the antibodies of the present invention can be used in any one of a number of conjugated (i.e. an immunoconjugate) or unconjugated forms. Alternatively, the antibodies of this invention can be used in a nonconjugated or "naked" form to harness the subject's natural defense mechanisms including complement-dependent cytotoxicity (CDC) and antibody dependent cellular toxicity (ADCC) to eliminate the malignant cells. The selection of which conjugated or unconjugated modified antibody to use will depend of the type and stage of cancer, use of adjunct treatment (e.g., chemotherapy or external radiation) and patient condition. It will be appreciated that one skilled in the art could readily make such a selection in view of the teachings herein.

The antibodies of the present invention can be assayed for immunospecific binding by any method known in the art. The immunoassays which can be used include, but are not limited to, competitive and non-competitive assay systems using techniques such as BIAcore analysis, FACS analysis, immunofluorescence, immunocytochemistry, Western blots, radioimmunoassays, ELISA, "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, and protein A immunoassays. Such assays are routine and well known in the art (see, e.g., Ausubel et al, eds, 1994, Current Protocols in Molecular Biology, Vol. 1, John Wiley & Sons, Inc., New York, which is incorporated by reference herein in its entirety).

In some embodiments, the immunospecificity of an antibody against a cancer stem cell marker is determined using ELISA. An ELISA assay comprises preparing antigen, coating wells of a 96 well microtiter plate with antigen, adding the antibody against a cancer stem cell marker conjugated to a detectable compound such as an enzymatic substrate (e.g. horseradish peroxidase or alkaline phosphatase) to the well, incubating for a period of time and detecting the presence of the antigen. In some embodiments, the antibody against a cancer stem cell marker is not conjugated to a detectable compound, but instead a second conjugated antibody that recognizes the antibody against a cancer stem cell marker is added to the well. In some embodiments, instead of coating the well with the antigen, the antibody against a cancer stem cell marker can be coated to the well and a second antibody conjugated to a detectable compound can be added following the addition of the antigen to the coated well. One of skill in the art would be knowledgeable as to the parameters that can be modified to increase the signal detected as well as other variations of ELISAs known in the art (see e.g. Ausubel et al, eds, 1994, Current Protocols in Molecular Biology, Vol. 1, John Wiley & Sons, Inc., New York at 11.2.1).

The binding affinity of an antibody to a cancer stem cell marker antigen and the off-rate of an antibody-antigen interaction can be determined by competitive binding assays. One example of a competitive binding assay is a radioimmunoassay comprising the incubation of labeled antigen (e.g. $^3H$ or $^{125}I$), or fragment or variant thereof, with the antibody of interest in the presence of increasing amounts of unlabeled antigen followed by the detection of the antibody bound to the labeled antigen. The affinity of the antibody against a cancer stem cell marker and the binding off-rates can be determined from the data by scatchard plot analysis. In some embodiments, BIAcore kinetic analysis is used to determine the binding on and off rates of antibodies against a cancer stem cell marker. BIAcore kinetic analysis comprises analyzing the binding and dissociation of antibodies from chips with immobilized cancer stem cell marker antigens on their surface.

In certain embodiments, the invention encompasses isolated polynucleotides that encode a polypeptide comprising an antibody, or fragment thereof, against human DLL4. Thus, the term "polynucleotide encoding a polypeptide" encompasses a polynucleotide which includes only coding sequences for the polypeptide as well as a polynucleotide which includes additional coding and/or non-coding sequences. The polynucleotides of the invention can be in the form of RNA or in the form of DNA. DNA includes cDNA, genomic DNA, and synthetic DNA; and can be double-stranded or single-stranded, and if single stranded can be the coding strand or non-coding (anti-sense) strand.

The present invention further relates to variants of the hereinabove described polynucleotides encoding, for example, fragments, analogs, and derivatives. The variant of the polynucleotide can be a naturally occurring allelic variant of the polynucleotide or a non-naturally occurring variant of the polynucleotide. In certain embodiments, the polynucleotide can have a coding sequence which is a naturally occurring allelic variant of the coding sequence of the disclosed polypeptides. As known in the art, an allelic variant is an alternate form of a polynucleotide sequence that have, for example, a substitution, deletion, or addition of one or more nucleotides, which does not substantially alter the function of the encoded polypeptide.

In certain embodiments the polynucleotides comprise the coding sequence for the mature polypeptide fused in the same reading frame to a polynucleotide which aids, for example, in expression and secretion of a polypeptide from a host cell (e.g. a leader sequence which functions as a secretory sequence for controlling transport of a polypeptide from the cell). The polypeptide having a leader sequence is a preprotein and can have the leader sequence cleaved by the host cell to form the mature form of the polypeptide. The polynucleotides can also encode for a proprotein which is the mature protein plus additional 5' amino acid residues. A mature protein having a prosequence is a proprotein and is an inactive form of the protein. Once the prosequence is cleaved an active mature protein remains.

In certain embodiments the polynucleotides comprise the coding sequence for the mature polypeptide fused in the same reading frame to a marker sequence that allows, for example, for purification of the encoded polypeptide. For example, the marker sequence can be a hexa-histidine tag supplied by a pQE-9 vector to provide for purification of the mature polypeptide fused to the marker in the case of a bacterial host, or the marker sequence can be a hemagglutinin (HA) tag derived from the influenza hemagglutinin protein when a mammalian host (e.g. COS-7 cells) is used.

In certain embodiments, the present invention provides isolated nucleic acid molecules having a nucleotide sequence at least 80% identical, at least 85% identical, at least 90% identical, at least 95% identical, and in some embodiments, at least 96%, 97%, 98% or 99% identical to a polynucleotide encoding a polypeptide comprising an antibody, or fragment thereof, against human DLL4.

By a polynucleotide having a nucleotide sequence at least, for example, 95% "identical" to a reference nucleotide sequence is intended that the nucleotide sequence of the polynucleotide is identical to the reference sequence except that the polynucleotide sequence can include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence can be deleted or substituted with another nucleotide, or a number of nucleotides up to 5% of the total nucleotides in the reference sequence can be inserted into the reference sequence. These mutations of the reference sequence can occur at the amino- or carboxy-terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 80% identical, at least 85% identical, at least 90% identical, and in some embodiments, at least 95%, 96%, 97%, 98%, or 99% identical to a reference sequence can be determined conventionally using known computer programs such as the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman, Advances in Applied Mathematics 2: 482 489 (1981), to find the best segment of homology between two sequences. When using Bestfit or any other sequence alignment program to determine whether a particular sequence is, for instance, 95% identical to a reference sequence according to the present invention, the parameters are set such that the percentage of identity is calculated over the full length of the reference nucleotide sequence and that gaps in homology of up to 5% of the total number of nucleotides in the reference sequence are allowed.

The polynucleotide variants can contain alterations in the coding regions, non-coding regions, or both. In some embodiments the polynucleotide variants contain alterations which produce silent substitutions, additions, or deletions, but do not alter the properties or activities of the encoded polypeptide. In some embodiments, nucleotide variants are produced by silent substitutions due to the degeneracy of the genetic code. Polynucleotide variants can be produced for a variety of reasons, e.g., to optimize codon expression for a particular host (change codons in the human mRNA to those preferred by a bacterial host such as E. coli).

The polypeptides of the present invention can be recombinant polypeptides, natural polypeptides, or synthetic polypeptides comprising an antibody, or fragment thereof, against human DLL4. It will be recognized in the art that some amino acid sequences of the invention can be varied without significant effect of the structure or function of the protein. Thus, the invention further includes variations of the polypeptides which show substantial activity or which include regions of an antibody, or fragment thereof, against human DLL4 protein. Such mutants include deletions, insertions, inversions, repeats, and type substitutions.

The polypeptides and analogs can be further modified to contain additional chemical moieties not normally part of the protein. Those derivatized moieties can improve the solubility, the biological half life or absorption of the protein. The moieties can also reduce or eliminate any desirable side effects of the proteins and the like. An overview for those moieties can be found in REMINGTON'S PHARMACEUTICAL SCIENCES, 20th ed., Mack Publishing Co., Easton, Pa. (2000).

The isolated polypeptides described herein can be produced by any suitable method known in the art. Such methods range from direct protein synthetic methods to constructing a DNA sequence encoding isolated polypeptide sequences and expressing those sequences in a suitable transformed host. In some embodiments, a DNA sequence is constructed using recombinant technology by isolating or synthesizing a DNA sequence encoding a wild-type protein of interest. Optionally, the sequence can be mutagenized by site-specific mutagenesis to provide functional analogs thereof. See, e.g. Zoeller et al., Proc. Nat'l. Acad. Sci. USA 81:5662-5066 (1984) and U.S. Pat. No. 4,588,585.

In some embodiments a DNA sequence encoding a polypeptide of interest would be constructed by chemical synthesis using an oligonucleotide synthesizer. Such oligonucleotides can be designed based on the amino acid sequence of the desired polypeptide and selecting those codons that are favored in the host cell in which the recombinant polypeptide of interest will be produced. Standard methods can be applied to synthesize an isolated polynucleotide sequence encoding an isolated polypeptide of interest. For example, a complete amino acid sequence can be used to construct a back-translated gene. Further, a DNA oligomer containing a nucleotide sequence coding for the particular isolated polypeptide can be synthesized. For example, several small oligonucleotides coding for portions of the desired polypeptide can be synthesized and then ligated. The individual oligonucleotides typically contain 5' or 3' overhangs for complementary assembly.

Once assembled (by synthesis, site-directed mutagenesis or another method), the polynucleotide sequences encoding a particular isolated polypeptide of interest will be inserted into an expression vector and operatively linked to an expression control sequence appropriate for expression of the protein in a desired host. Proper assembly can be confirmed by nucleotide sequencing, restriction mapping, and expression of a biologically active polypeptide in a suitable host. As is well known in the art, in order to obtain high expression levels of a transfected gene in a host, the gene must be operatively linked to transcriptional and translational expression control sequences that are functional in the chosen expression host.

Recombinant expression vectors are used to amplify and express DNA encoding cancer stem cell marker polypeptide fusions. Recombinant expression vectors are replicable DNA constructs which have synthetic or cDNA-derived DNA fragments encoding a cancer stem cell marker polypeptide fusion or a bioequivalent analog operatively linked to suitable transcriptional or translational regulatory elements derived from mammalian, microbial, viral or insect genes. A transcriptional unit generally comprises an assembly of (1) a genetic element or elements having a regulatory role in gene expression, for example, transcriptional promoters or enhancers, (2) a structural or coding sequence which is transcribed into mRNA and translated into protein, and (3) appropriate transcription and translation initiation and termination sequences, as described in detail below. Such regulatory elements can include an operator sequence to control transcription. The ability to replicate in a host, usually conferred by an origin of replication, and a selection gene to facilitate recognition of transformants can additionally be incorporated. DNA regions are operatively linked when they are functionally related to each other. For example, DNA for a signal peptide (secretory leader) is operatively linked to DNA for a polypeptide if it is expressed as a precursor which participates in the secretion of the polypeptide; a promoter is operatively linked to a coding sequence if it controls the transcription of the sequence; or a ribosome binding site is operatively linked to a coding sequence if it is positioned so as to permit translation. Generally, operatively linked means contiguous and, in the case of secretory leaders, means contiguous and in reading frame. Structural elements intended for use in yeast expression systems include a leader sequence enabling extracellular secretion of translated protein by a host cell. Alternatively, where recombinant protein is expressed without a leader or transport sequence, it can include an N-terminal methionine residue. This residue can optionally be subsequently cleaved from the expressed recombinant protein to provide a final product.

The choice of expression control sequence and expression vector will depend upon the choice of host. A wide variety of expression host/vector combinations can be employed. Useful expression vectors for eukaryotic hosts, include, for example, vectors comprising expression control sequences from SV40, bovine papilloma virus, adenovims and cytomegalovirus. Useful expression vectors for bacterial hosts include known bacterial plasmids, such as plasmids from Esherichia coli, including pCR 1, pBR322, pMB9 and their derivatives, wider host range plasmids, such as M13 and filamentous single-stranded DNA phages.

Suitable host cells for expression of a cancer stem cell marker protein include prokaryotes, yeast, insect or higher eukaryotic cells under the control of appropriate promoters. Prokaryotes include gram negative or gram positive organisms, for example E. coli or bacilli. Higher eukaryotic cells include established cell lines of mammalian origin as described below. Cell-free translation systems could also be employed. Appropriate cloning and expression vectors for use with bacterial, fungal, yeast, and mammalian cellular hosts are described by Pouwels et al. (Cloning Vectors: A Laboratory Manual, Elsevier, N.Y., 1985), the relevant disclosure of which is hereby incorporated by reference.

Various mammalian or insect cell culture systems are also advantageously employed to express recombinant protein. Expression of recombinant proteins in mammalian cells can be performed because such proteins are generally correctly folded, appropriately modified and completely functional. Examples of suitable mammalian host cell lines include the COS-7 lines of monkey kidney cells, described by Gluzman (Cell 23:175, 1981), and other cell lines capable of expressing an appropriate vector including, for example, L cells, C127, 3T3, Chinese hamster ovary (CHO), HeLa and BHK cell lines. Mammalian expression vectors can comprise nontranscribed elements such as an origin of replication, a suitable promoter and enhancer linked to the gene to be expressed, and other 5' or 3' flanking nontranscribed sequences, and 5' or 3' nontranslated sequences, such as necessary ribosome binding sites, a polyadenylation site, splice donor and acceptor sites, and transcriptional termination sequences. Baculovirus systems for production of heterologous proteins in insect cells are reviewed by Luckow and Summers, Bio/Technology 6:47 (1988).

The proteins produced by a transformed host can be purified according to any suitable method. Such standard methods include chromatography (e.g., ion exchange, affinity and sizing column chromatography), centrifugation, differential solubility, or by any other standard technique for protein purification. Affinity tags such as hexahistidine, maltose binding domain, influenza coat sequence and glutathione-S-transferase can be attached to the protein to allow easy purification by passage over an appropriate affinity column. Isolated proteins can also be physically characterized using such techniques as proteolysis, nuclear magnetic resonance and x-ray crystallography.

For example, supernatants from systems which secrete recombinant protein into culture media can be first concentrated using a commercially available protein concentration filter, for example, an Amicon or Millipore Pellicon ultrafiltration unit. Following the concentration step, the concentrate can be applied to a suitable purification matrix. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Finally, one or more reversed-phase high performance liquid chromatography (RP-HPLC) steps employing hydrophobic RP-HPLC media, e.g., silica gel having pendant methyl or other aliphatic groups, can be employed to further purify a cancer stem cell protein-Fc composition. Some or all of the foregoing purification steps, in various combinations, can also be employed to provide a homogeneous recombinant protein.

Recombinant protein produced in bacterial culture can be isolated, for example, by initial extraction from cell pellets, followed by one or more concentration, salting-out, aqueous ion exchange or size exclusion chromatography steps. High performance liquid chromatography (HPLC) can be employed for final purification steps. Microbial cells employed in expression of a recombinant protein can be disrupted by any convenient method, including freeze-thaw cycling, sonication, mechanical disruption, or use of cell lysing agents.

The present invention provides methods for inhibiting the growth of tumorigenic cells expressing a cancer stem cell marker using the antibodies against a cancer stem cell marker described herein. In certain embodiments, the method of inhibiting the growth of tumorigenic cells expressing a cancer stem cell marker comprises contacting the cell with an antibody against a cancer stem cell marker in vitro. For example, an immortalized cell line or a cancer cell line that expresses a cancer stem cell marker is cultured in medium to which is added an antibody against the expressed cancer stem cell marker to inhibit cell growth. In some embodiments, tumor cells comprising tumor stem cells are isolated from a patient sample such as, for example, a tissue biopsy, pleural effusion, or blood sample and cultured in medium to which is added an antibody against a cancer stem cell marker to inhibit cell growth.

In some embodiments, the method of inhibiting the growth of tumorigenic cells expressing a cancer stem cell marker comprises contacting the cell with an antibody against a cancer stem cell marker in vivo. In certain embodiments, contacting a tumorigenic cell with an antibody against a cancer stem cell marker is undertaken in an animal model. For example, xenografts expressing a cancer stem cell marker are grown in immunocompromised mice (e.g. NOD/SCID mice) that are administered an antibody against a cancer stem cell marker to inhibit tumor growth. In some embodiments, cancer stem cells that express a cancer stem cell marker are isolated from a patient sample such as, for example, a tissue biopsy, pleural effusion, or blood sample and injected into immunocompromised mice that are then administered an antibody against the cancer stem cell marker to inhibit tumor cell growth. In some embodiments, the antibody against a cancer stem cell marker is administered at the same time or shortly after introduction of tumorigenic cells into the animal to prevent tumor growth. In some embodiments, the antibody against a cancer stem cell marker is administered as a therapeutic after the tumorigenic cells have grown to a specified size.

The present invention further provides pharmaceutical compositions comprising antibodies that target a cancer stem cell marker. These pharmaceutical compositions find use in inhibiting tumor cell growth and treating cancer in human patients.

Formulations are prepared for storage and use by combining a purified antibody of the present invention with a pharmaceutically acceptable vehicle (e.g. carrier, excipient) (Remington, The Science and Practice of Pharmacy 20th Edition Mack Publishing, 2000). Suitable pharmaceutically acceptable vehicles include, but are not limited to, nontoxic buffers such as phosphate, citrate, and other organic acids; salts such as sodium chloride; antioxidants including ascorbic acid and methionine; preservatives (e.g. octadecyldimethylbenzyl ammonium chloride; hexamethonium chloride; benzalkonium chloride; benzethonium chloride; phenol, butyl or benzyl alcohol; alkyl parabens, such as methyl or propyl paraben; catechol; resorcinol; cyclohexanol; 3-pentanol; and m-cresol); low molecular weight polypeptides (e.g. less than about 10 amino acid residues); proteins such as serum albumin, gelatin, or immunoglobulins; hydrophilic polymers such as polyvinylpyrrolidone; amino acids such as glycine, glutamine, asparagine, histidine, arginine, or lysine; carbohydrates such as monosacchandes, disaccharides, glucose, mannose, or dextrins; chelating agents such as EDTA; sugars such as sucrose, mannitol, trehalose or sorbitol; salt-forming counter-ions such as sodium; metal complexes (e.g. Zn-protein complexes); and non-ionic surfactants such as TWEEN or polyethylene glycol (PEG).

The pharmaceutical composition of the present invention can be administered in any number of ways for either local or systemic treatment. Administration can be topical (such as to mucous membranes including vaginal and rectal delivery) such as transdermal patches, ointments, lotions, creams, gels, drops, suppositories, sprays, liquids and powders; pulmonary (e.g., by inhalation or insufflation of powders or aerosols, including by nebulizer; intratracheal, intranasal, epidermal and transdermal); oral; or parenteral including intravenous, intraarterial, subcutaneous, intraperitoneal or intramuscular injection or infusion; or intracranial (e.g., intrathecal or intraventricular) administration.

The therapeutic formulation can be in unit dosage form. Such formulations include tablets, pills, capsules, powders, granules, solutions or suspensions in water or non-aqueous media, or suppositories for oral, parenteral, or rectal administration or for administration by inhalation. In solid compositions such as tablets the principal active ingredient is mixed with a pharmaceutical carrier. Conventional tableting ingredients include corn starch, lactose, sucrose, sorbitol, talc, stearic acid, magnesium stearate, dicalcium phosphate or gums, and other diluents (e.g. water) to form a solid preformulation composition containing a homogeneous mixture of a compound of the present invention, or a non-toxic pharmaceutically acceptable salt thereof. The solid preformulation composition is then subdivided into unit dosage forms of the type described above. The tablets, pills, etc of the novel composition can be coated or otherwise compounded to provide a dosage form affording the advantage of prolonged action. For example, the tablet or pill can comprise an inner composition covered by an outer component. Furthermore, the two components can be separated by an enteric layer that serves to resist disintegration and permits the inner component to pass intact through the stomach or to be delayed in release. A variety of materials can be used for such enteric layers or coatings, such materials including a number of polymeric acids and mixtures of polymeric acids with such materials as shellac, cetyl alcohol and cellulose acetate.

Pharmaceutical formulations include antibodies of the present invention complexed with liposomes (Epstein, et al., 1985, *Proc. Natl. Acad. Sci. USA* 82:3688; Hwang, et al., 1980, *Proc. Natl. Acad. Sci. USA* 77:4030; and U.S. Pat. Nos. 4,485,045 and 4,544,545). Liposomes with enhanced circulation time are disclosed in U.S. Pat. No. 5,013,556. Some liposomes can be generated by the reverse phase evaporation with a lipid composition comprising phosphatidylcholine, cholesterol, and PEG-derivatized phosphatidylethanolamine (PEG-PE). Liposomes are extruded through filters of defined pore size to yield liposomes with the desired diameter.

The antibodies can also be entrapped in microcapsules. Such microcapsules are prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions as described in Remington, The Science and Practice of Pharmacy 20th Ed. Mack Publishing (2000).

In addition sustained-release preparations can be prepared. Suitable examples of sustained-release preparations include semipermeable matrices of solid hydrophobic polymers containing the antibody, which matrices are in the form of shaped articles (e.g. films, or microcapsules). Examples of sustained-release matrices include polyesters, hydrogels such as poly (2-hydroxyethyl-methacrylate) or poly(v nylalcohol), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(-)-3-hydroxybutyric acid.

In some embodiments, the treatment involves the combined administration of an antibody of the present invention and a chemotherapeutic agent or cocktail of multiple different chemotherapeutic agents. Treatment with an antibody can occur prior to, concurrently with, or subsequent to administration of chemotherapies. Chemotherapies contemplated by the invention include chemical substances or drugs which are known in the art and are commercially available, such as Doxorubicin, 5-Fluorouracil, Cytosine arabinoside ("Ara-C"), Cyclophosphamide, Thiotepa, Busulfan, Cytoxin, Taxol, Methotrexate, Cisplatin, Melphalan, Vinblastine and Carboplatin. Combined administration can include co-administration, either in a single pharmaceutical formulation or using separate formulations, or consecutive administration in either order but generally within a time period such that all active agents can exert their biological activities simultaneously. Preparation and dosing schedules for such chemotherapeutic agents can be used according to manufacturers' instructions or as determined empirically by the skilled practitioner. Preparation and dosing schedules for such chemotherapy are also described in Chemotherapy Service Ed., M. C. Perry, Williams & Wilkins, Baltimore, Md. (1992).

In certain embodiments of the invention, the treatment involves the combined administration of an antibody of the present invention and a second therapeutic agent. As used herein, "a second therapeutic agent" includes, but is not limited to, chemotherapeutic agent, radiation therapy, cytokine and antibody against other tumor associated antigen.

In other embodiments, the treatment involves the combined administration of an antibody of the present invention and radiation therapy. Treatment with the antibody can occur prior to, concurrently with, or subsequent to administration of radiation therapy. Any dosing schedules for such radiation therapy can be used as determined by the skilled practitioner.

In other embodiments, the treatment can involve the combined administration of antibodies of the present invention with other antibodies against additional tumor associated antigens including, but not limited to, antibodies that bind to the EGF receptor (EGFR) (Erbitux®), the erbB2 receptor (HER2) (Herceptin®), and vascular endothelial growth factor (VEGF) (Avastin®). Furthermore, treatment can include administration of one or more cytokines, can be accompanied by surgical removal of cancer cells or any other therapy deemed necessary by a treating physician.

For the treatment of the disease, the appropriate dosage of an antibody of the present invention depends on the type of disease to be treated, the severity and course of the disease, the responsiveness of the disease, whether the antibody is administered for therapeutic or preventative purposes, previous therapy, patient's clinical history, and so on all at the discretion of the treating physician. The antibody can be administered one time or over a series of treatments lasting from several days to several months, or until a cure is effected or a diminution of the disease state is achieved (e.g. reduction in tumor size). Optimal dosing schedules can be calculated from measurements of drug accumulation in the body of the patient and will vary depending on the relative potency of an individual antibody. The administering physician can easily determine optimum dosages, dosing methodologies and repetition rates. In general, dosage is from 0.01 µg to 100 mg per kg of body weight, and can be given once or more daily, weekly, monthly or yearly. The treating physician can estimate repetition rates for dosing based on measured residence times and concentrations of the drug in bodily fluids or tissues.

The present invention provides kits comprising the antibodies described herein and that can be used to perform the methods described herein. In certain embodiments, a kit comprises at least one purified antibody against a cancer stem cell marker in one or more containers. In some embodiments, the kits contain all of the components necessary and/or sufficient to perform a detection assay, including all controls, directions for performing assays, and any necessary software for analysis and presentation of results. One skilled in the art will readily recognize that the disclosed antibodies of the present invention can be readily incorporated into one of the established kit formats which are well known in the art.

Embodiments of the present disclosure can be further defined by reference to the following examples, which describe in detail preparation of antibodies of the present disclosure and methods for using antibodies of the present disclosure. It will be apparent to those skilled in the art that many modifications, both to materials and methods, may be practiced without departing from the scope of the present disclosure. Wherever possible, the same reference numbers will be used throughout the drawings to refer to the same or like parts. As used herein and in the appended claims, the singular forms "a," "or," and "the" include plural referents unless the context clearly dictates otherwise. Thus, for example, reference to "an antibody" includes a plurality of such antibodies or one or more antibodies and equivalents thereof known to those skilled in the art. Furthermore, all numbers expressing quantities of ingredients, reaction conditions, purity, polypeptide and polynucleotide lengths, and so forth, used in the specification, are modified by the term "about," unless otherwise indicated. Accordingly, the numerical parameters set forth in the specification and claims are approximations that may vary depending upon the desired properties of the present invention.

EXAMPLES

Example 1

Production of Monoclonal and Humanized DLL4 Antibodies

Antigen Production

A recombinant polypeptide fragment of the extracellular domain of human DLL4 was generated as an antigen for antibody production. Standard recombinant DNA technology was used to isolate a polynucleotide encoding amino acids 1-522 of DLL4 (SEQ ID NO: 25). This polynucleotide was ligated in-frame N-terminal to either a human Fc-tag or histidine-tag and cloned into a transfer plasmid vector for baculovirus mediated expression in insect cells. Standard transfection, infection, and cell culture protocols were used to produce recombinant insect cells expressing the corresponding DLL4 polypeptide (O'Reilley et al., *Baculovirus expression vectors: A Laboratory Manual*, Oxford: Oxford University Press (1994)).

Cleavage of the endogenous signal sequence of human DLL4 was approximated using cleavage prediction software SignalP 3.0, however the actual in vivo cleavage point can differ by a couple of amino acids either direction. The predicated cleavage of DLL4 is between amino acids 1 and 26, thus DLL4 antigen protein comprises approximately amino acid 27 through amino acid 522. Antigen protein was purified from insect cell conditioned medium using Protein A and $Ni^{++}$-chelate affinity chromatography. Purified antigen protein was then dialyzed against PBS (pH=7), concentrated to approximately 1 mg/ml, and sterile filtered in preparation for immunization.

Immunization

Mice (n=3) were immunized with purified DLL4 antigen protein (Antibody Solutions; Mountain View, Calif.) using standard techniques. Blood from individual mice was screened approximately 70 days after initial immunization for antigen recognition using ELISA and FACS analysis (described in detail below). The two animals with the highest antibody titers were selected for final antigen boost after which spleen cells were isolated for hybridoma production. Hybridoma cells were plated at 1 cell per well in 96 well plates, and the supernatant from each well screened by ELISA and FACS analysis against antigen protein. Several hybridomas with high antibody titer were selected and scaled up in static flask culture. Antibodies were purified from the hybridoma supernatant using protein A or protein G agarose chromatography. Purified monoclonal antibodies were again tested by FACS and are isotyped to select for IgG and IgM antibodies.

FACS Analysis

To select monoclonal antibodies produced by hybridomas clones that recognize native cell-surface DLL4 protein, FACs analysis was used. HEK293 cells were co-transfected with expression vectors encoding a full-length cDNA clone of DLL4 and the transfection marker GFP. Twenty-four to forty-eight hours post-transfection, cells were collected in suspension and incubated on ice with anti-DLL4 antibodies or control IgG to detect background antibody binding. The cells were washed and primary antibodies detected with anti-mouse secondary antibodies conjugated to a fluorescent chromophore. Labeled cells were then sorted by FACS to identify anti-DLL4 antibodies that specifically recognize cell surface expression of native cell-surface DLL4 protein. Monoclonal antibodies 21M14 and 21M18 recognized DLL4 on transfected cells (FIG. 1). Murine antibody 21M18 was deposited on Sep. 28, 2007 with American Tissue Culture Collection (No. PTA-8670), located at 10801 University Blvd., Manassas, Va. 20110-2209, under the terms of the Budapest Treaty.

The ability of antibodies directed towards DLL4 to interfere with the interaction between DLL4 and Notch was next determined using flow cytometry. HEK 293 cells stably transduced with DLL4 cDNA were incubated with either Notch1-EGF10-15-Fc or control protein-Fc in the presence of anti-DLL4 or control antibodies. Binding of Fc fusion proteins to cells expressing DLL4 was detected by PE-conjugated goat anti-Fc antibody and flow cytometry. The ability of anti-DLL4 antibodies inhibit the binding of Notch to DLL4 was thus determined by a decrease in fluorescence intensity. As shown in FIG. 2A, inhibition of Notch binding was observed with murine antibodies 21M14 and 21M18, but not 21M12. Furthermore, murine 21M18 specifically binds human not murine DLL4, and blocks binding of human DLL4 but not murine DLL4 binding to cells expressing Notch1 (FIG. 2B). These data indicate that 21M18 in xenograft experiments targets human DLL4 expressed on the tumor cells and not murine DLL4 expressed on the vasculature.

Epitope Mapping

Figure 3:
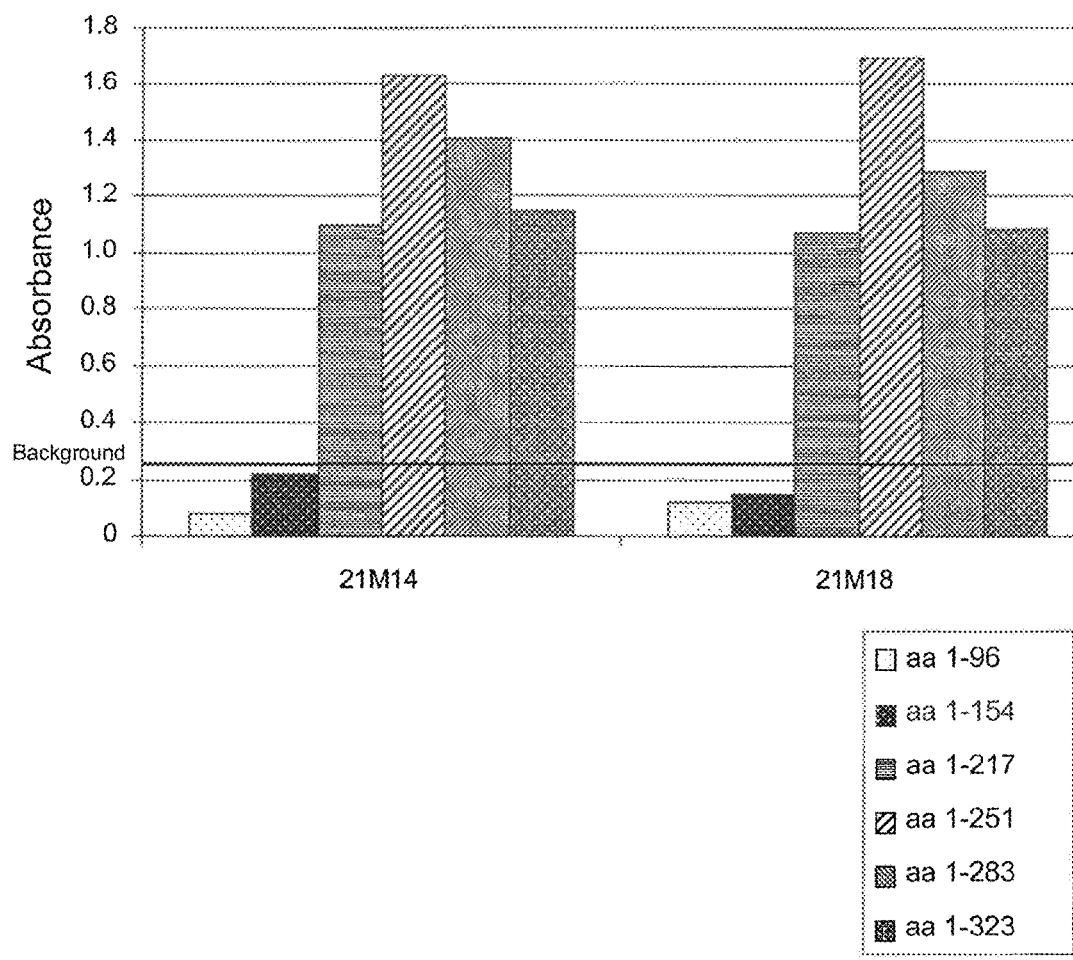
FIG. 3: Epitope Mapping of Anti-DLL4 Antibodies. A) Fusion proteins with nested deletions of the extracellular domain of human DLL4 were incubated in an ELISA assay with 21M14 and 21M18 anti-DLL4 antibodies. No binding above background was detected in the presence of fusion proteins containing between amino acids 1 to 154 (aa 1-96, white bar with black dots; aa 1-154, black bar with white dots). In contrast, binding was detected between anti-DLL4 antibodies and all fusion proteins containing between amino acids 1 to 217, including the DSL domain, of DLL4 (aa 1-217, horizontal striped bar; aa 1-251, diagonal striped bar; aa 1-283, hatched bar; aa 1-323, gray bar with white dots). B) Western blots show expression of human DLL4 (h-DLL4) C-terminal deletion proteins and murine-human DLL4 chimeric fusion proteins (anti-hFc; top). The DLL4 fusion proteins comprise one or more of domains 1 to 6, where domains 1 and 2 are N-terminal amino acids 1 to 154; domain 3 is the DSL domain from amino acids 155 to 217; and domains 4, 5, and 6 are each an EGF domain as depicted graphically in C. 21M18 antibodies recognize h-DLL4 protein only in the presence of amino acids 1-217 (hDLL4dom1-3). In contrast to the human protein, fusion proteins comprising murine DLL4 (m-DLL4) amino acids 1-217 (dom1-3) are not recognized by 21M18 (m-DLL4 dom1-3:h-DLL4dom4-6). Yet fusion proteins comprising h-DLL4 amino acids 1-154 (dom1-2) in the presence of murine dom3 are recognized by 21M18 (h-DLL4 dom1-2:mDLL4dom3-6). C) A schematic summary of the binding data of B is shown. The domain structure of DLL4 is shown at top with the DLL4 fusion proteins listed and shown schematically on the left side with human protein represented by light gray and mouse protein represented by dark gray. 21M18 binding to each DLL4 fragment is indicated by a "+" versus a "−". D) ELISA analysis of 21M18 binding to DLL4 protein fragments containing substitution of corresponding murine residues for human residues at select positions. 21M18 displays impaired binding to DLL4 protein fragments with substitutions at amino acids 68, 69, and 71 (replacement of valine, valine, and proline) or at amino acids 142 and 144 (replacement of lysine and alanine) E) ELISA analysis of the binding of antibodies 21M18 and 21M21 to DLL4 protein fragments containing substitution of corresponding murine residues for human residues at select positions within the DSL domain. Antibody 21M21 displays impaired binding to human DLL4 protein fragments containing amino acid substitutions at amino acids 161 and 162 (replacement of threonine and serine). As 21M21 does not impair DLL4 function in signaling assays (see FIG. 6), this demonstrates that not all antibodies that bind to the DSL region impact DLL4 function.
Figure 3B:
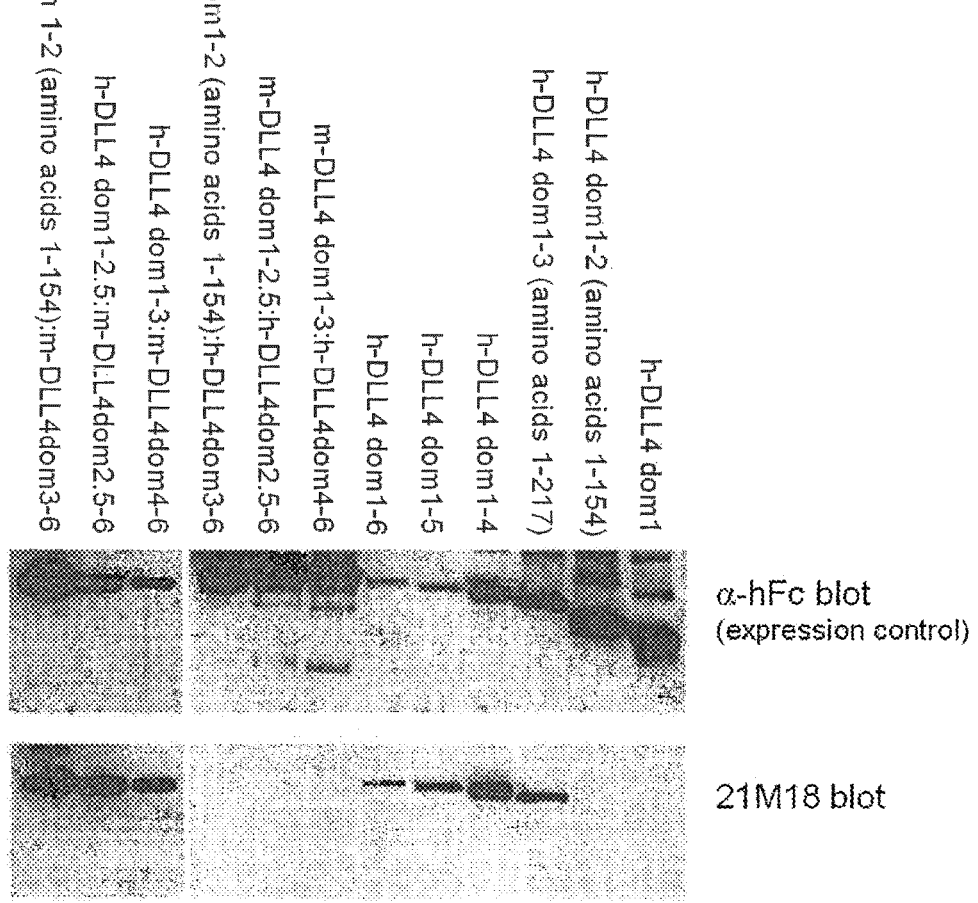
Figure 3C:
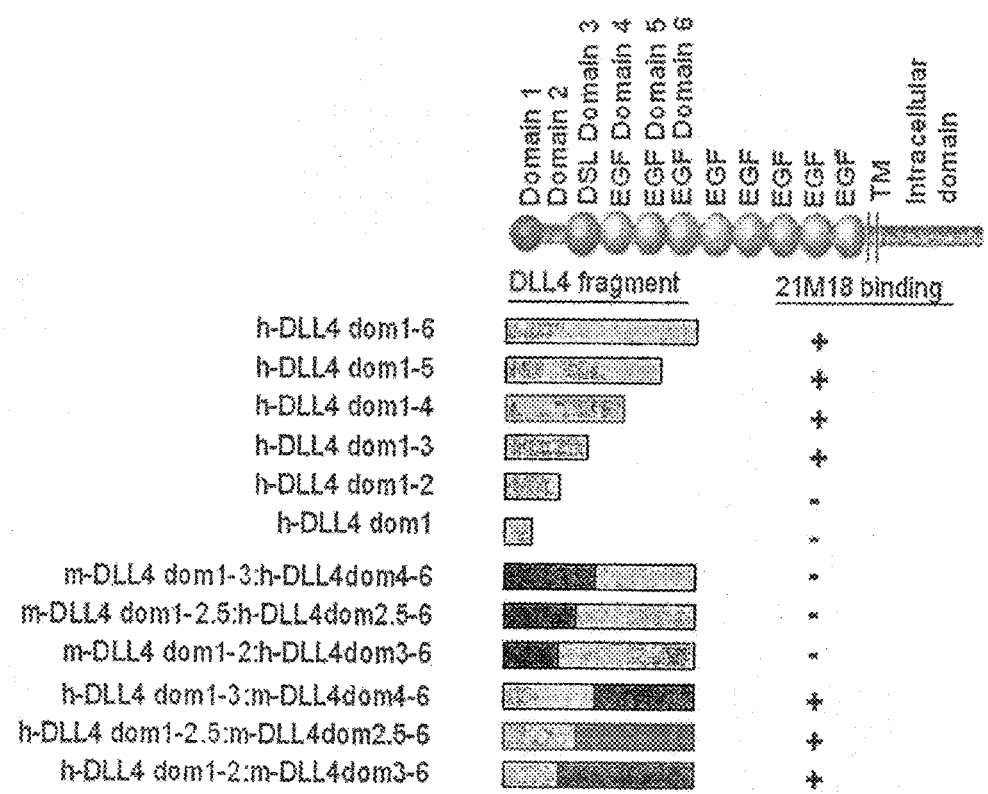
Figure 3D:
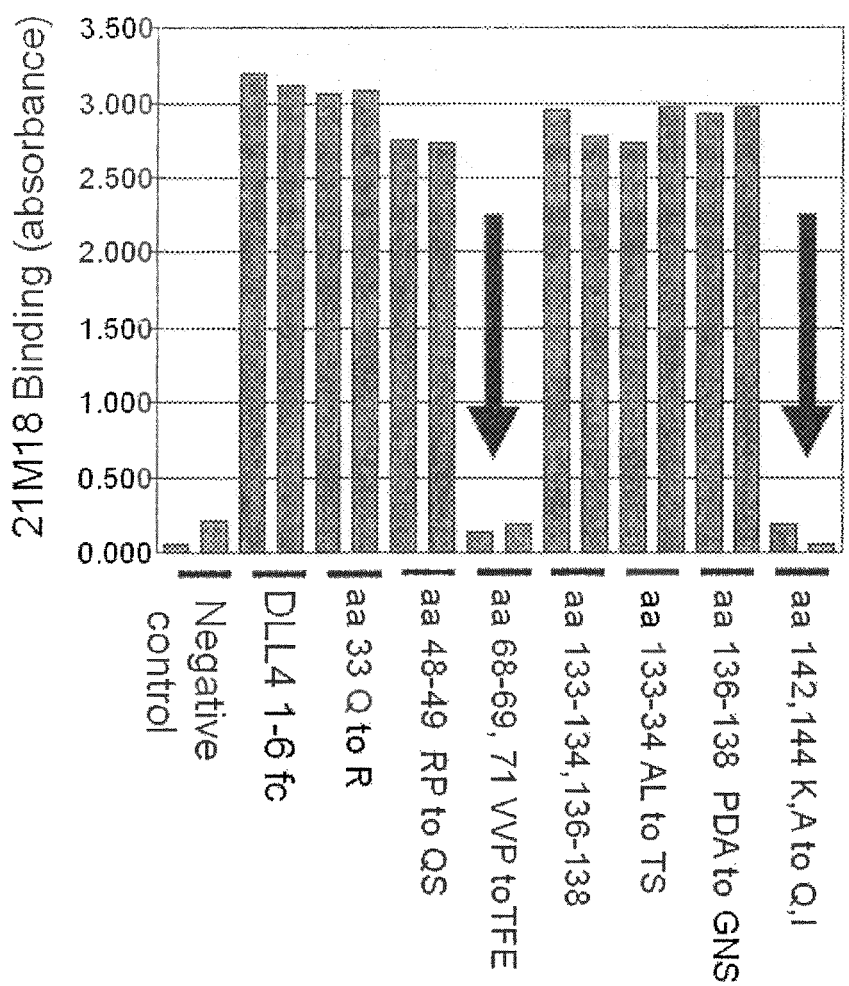
Figure 6:
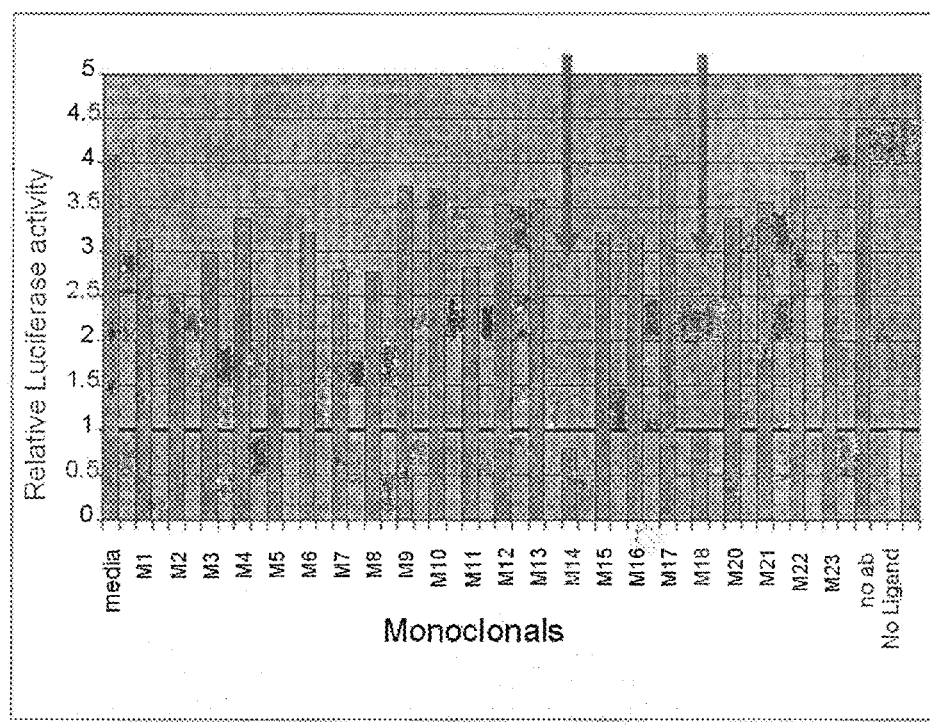
FIG. 6: DLL4 Antibodies Block Notch Signaling. HeLa cells co-transfected with Hes1-Luc reporter and *Renilla* luciferase reporter vectors were incubated with DLL4-Fc protein in the presence or absence of anti-DLL4 antibodies. Decreased luciferase levels demonstrate loss of DLL4 Notch pathway activation by 21M14 and 21M18 antibodies.

To identify antibodies that recognize specific regions of the DLL4 extracellular domain, epitope mapping was performed. Mammalian expression plasmid vectors comprising a CMV promoter upstream of polynucleotides that encode a nested series of deletion fragments of the extracellular domain of DLL4 fused to Fc protein were generated using standard recombinant DNA technology. Additional constructs that encoded fragments of DLL4 that were chimera of human and mouse DLL4 fused to Fc protein were also generated using standard recombinant DNA technology. A further series of DLL4-fc fusion proteins were designed that included specific amino acid substitutions. These recombinant fusion proteins were expressed in transiently transfected HEK 293 cells from which conditioned medium was collected twenty-four to forty-eight hours post-transfection for ELISA. The DLL4 fusion protein fragments were captured on plates coated with anti-human Fc antibodies. Anti-DLL4 antibodies were then allowed to interact with the bound DLL4 fragments and binding was measured by subsequent incubation with HRP conjugated anti-mouse antibody and detection of HRP activity (FIG. 3A). As shown in FIG. 3, monoclonal murine antibodies 21M14 and 21M18 recognize the epitope contained within amino acids 1-217 of DLL4. This region contains a motif termed the "DSL (Delta/Serrate/lag-2)" domain present in several Notch ligands (Tax et al., 1994, *Nature* 368:150-4). Additionally, anti-DLL4 mAbs were examined for binding to DLL4 fusion protein fragments by western blot analysis (FIG. 3B). This work demonstrates the human specific binding of 21M18 to DLL4 within amino acids 1-154 in the presence of a DSL domain present within amino acids 155-217. This demonstrates a previously unappreciated importance of this N-terminal sequence to DLL4 function. This work is summarized in schematic form (FIG. 3C) with 21M18 binding or lack of binding denoted by a "+" or "−" respectively. The binding of 21M18 was further characterized by examination of binding of 21M18 to a series of DLL4 protein fragments (DLL4dom1-6) containing specific amino acid substitutions swapping the human DLL4 amino acids for the corresponding murine amino acids. These fusion proteins were screened for binding to 21M18 by ELISA. Several positions were identified as important for 21M18 binding as shown (FIG. 3D). 21M18 displays impaired binding to DLL4 protein fragments with substitutions at amino acids 68, 69, and 71 (replacement of valine, valine, and proline) or at amino acids 142 and 144 (replacement of lysine and alanine). In contrast a distinct antibody 21M21 binds to an epitope contained within the DSL region (FIG. 3E), but this antibody does not impact DLL4 function as shown in FIG. 6, demonstrating that binding to DSL does not predict a functional antibody.

Chimeric Antibodies

After monoclonal antibodies that specifically recognize DLL4 are identified, these antibodies are modified to overcome the human anti-mouse antibody (HAMA) immune response when rodent antibodies are used as therapeutics agents. In certain embodiments, the variable regions of the heavy-chain and light-chain of the selected monoclonal antibody are isolated by RT-PCR from hybridoma cells and ligated in-frame to human $IgG_1$ heavy-chain and kappa light chain constant regions, respectively, in mammalian expression vectors. Alternatively a human Ig expression vector such as TCAE 5.3 is used that contains the human IgG$_1$ heavy-chain and kappa light-chain constant region genes on the same plasmid (Preston et al., 1998, *Infection & Immunity* 66:4137-42). Expression vectors encoding chimeric heavy- and light-chains are then co-transfected into Chinese hamster ovary (CHO) cells for chimeric antibody production. Immunoreactivity and affinity of chimeric antibodies are compared to parental murine antibodies by ELISA and FACS.

Humanized Antibodies

In certain embodiments, humanized antibodies against DLL4 are generated. The variable domains of the murine monoclonal antibody 21M18 were isolated and sequenced from the hybridoma line using degenerate PCR essentially as described in Larrick, J. M., et al., 1989, *Biochem. Biophys. Res. Comm.* 160: 1250 and Jones, S. T. & Bendig, M. M., 1991, *Bio/Technology* 9: 88. Human heavy and light chain variable framework regions likely to be structurally similar to the parental 21M18 antibody amino acid sequences are then chosen as the human framework regions for humanization. To identify the candidate human framework regions, the predicted protein sequences encoded by the $V_H$ and $V_L$ murine variable domains of 21M18 are compared with human antibody sequences encoded by expressed human cDNA using BLAST searches for human sequence deposited in Genbank. Using this method, expressed human cDNA sequences (e.g. genbank AY393019, DC295533) are selected for further analysis in designing a heavy chain framework.

The amino acid differences between candidate humanized framework heavy chains and the parent murine monoclonal antibody 21M18 heavy chain are evaluated for likely importance, and a judgment made as to whether each difference in position contributes to proper folding of the 21M18 antibody. This analysis is guided by examination of solved crystal structures of other antibody fragments (e.g. the structure of fab 2E8 as described in Trakhanov et al, *Acta Crystallogr D Biol Crystallogr*, 1999, 55:122-28). Structures are modeled using computer software including Jmol, quick PDB, and Pymol. Consideration is given to the potential impact of an amino acid at a given position on the packing of the β-sheet framework, the interaction between the heavy and light chain variable domains, the degree of solvent exposure of the amino acid side chain, and the likelihood that an amino acid would impact the positioning of the CDR loops. From this analysis, five candidate $V_H$ chains fused in-frame to the human IgG2 constant region are chemically synthesized. The candidate heavy chains comprise: i) of a functional human framework containing selected substitutions within the synthetic framework region based on analysis of likely impact on 21M18 binding function and ii) the parental 21M18 murine antibody CDRs (SEQ ID NOs: 1, 2, and 5).

Similarly, amino acid differences between a selected human framework IGK(V)4-1 light chain and the parent murine monoclonal antibody 21M18 light chain are identified, and a judgment is then made as to whether each difference in position contributes to proper folding of the 21M18 antibody. From this analysis, five candidate $V_L$ chains are chemically synthesized. The first candidate light chain comprises: i) a fully IGK(V)4-1 human framework and ii) the parental 21M18 murine antibody CDRs (SEQ ID NOs: 9, 10, and 11). The four additional candidate light chains comprise: i) the IGK(V)4-1 human framework region with an increasing number of 21M18 murine residues retained in the framework region and ii) the parental 21M18 murine antibody CDRs (SEQ ID NOs: 9, 10, and 11).

Figure 4A:
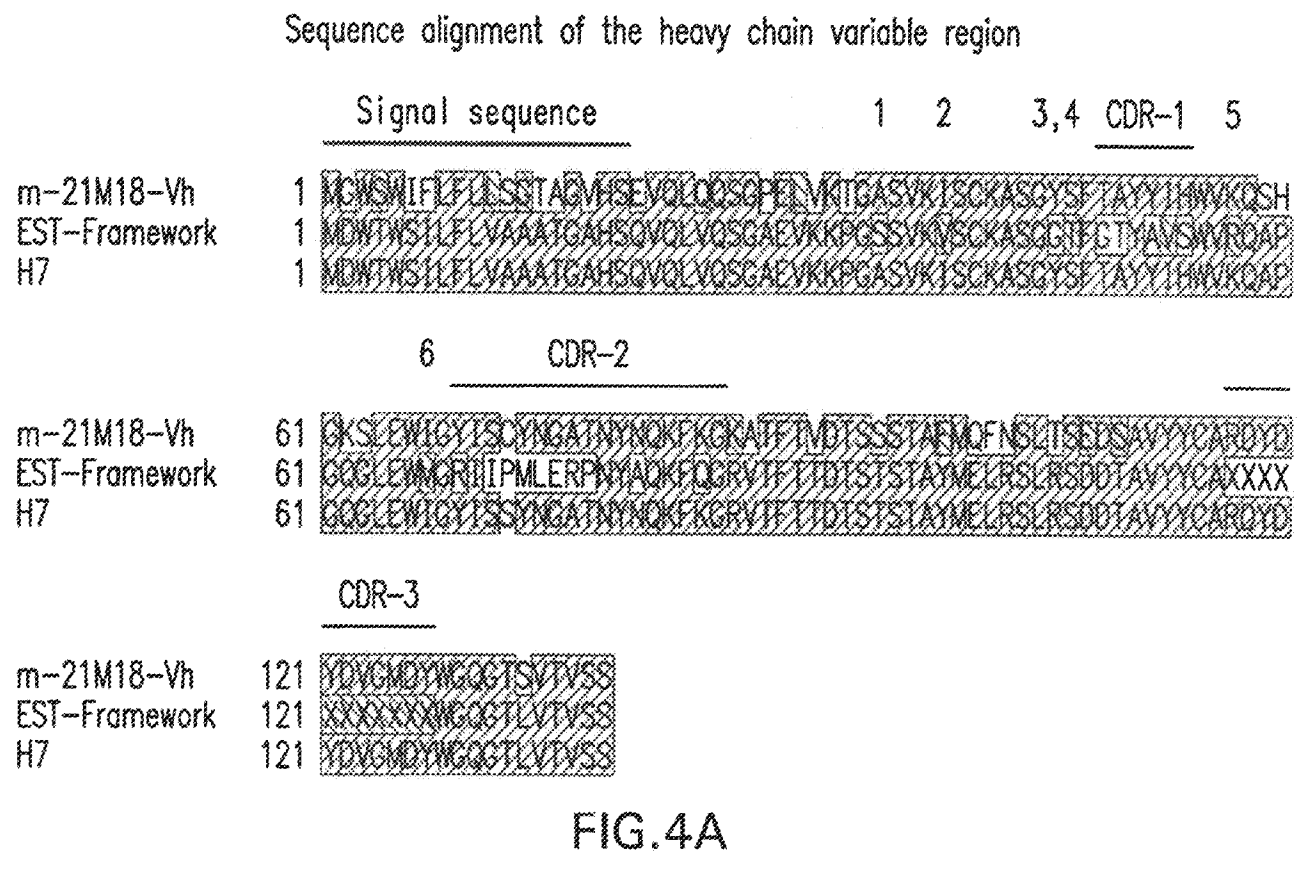
Figure 5:
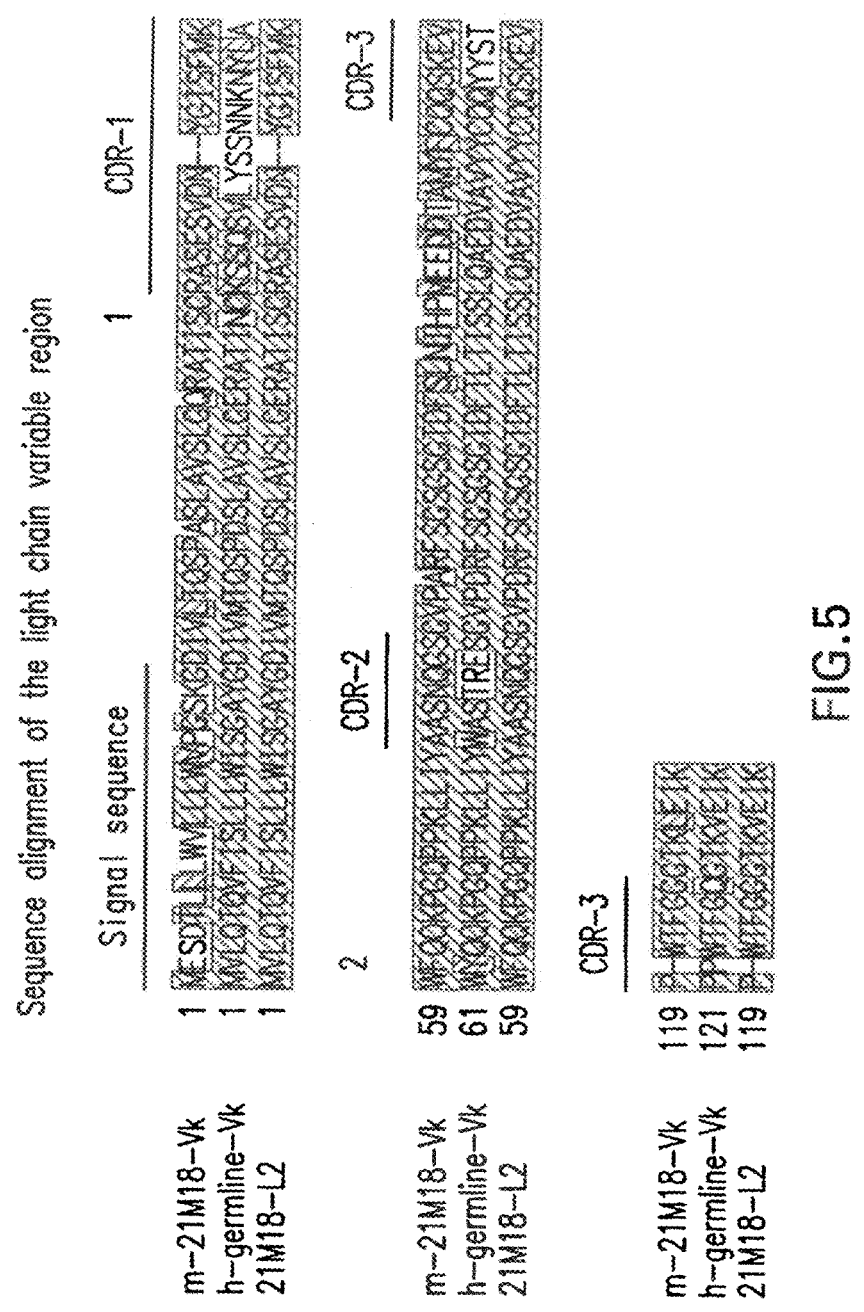
Figure 4B:
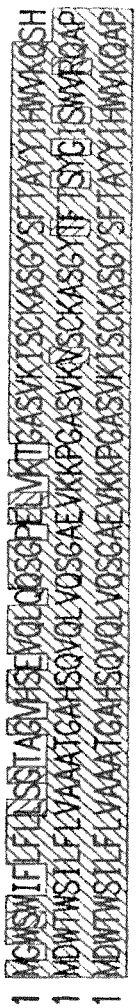
FIG. 4: Sequence alignment of the heavy chain variable region. A) Parental murine 21M18 antibody sequence (m-21M18-Vh, top) (SEQ ID NO:28) human expressed framework sequence (h-EST-framework, middle) (SEQ ID NO:29) and the humanized 21M18 heavy chain variable region sequence (21M18-H7, bottom) (SEQ ID NO:30) are shown with conserved amino acid residues shaded in black. The three CDRs are marked showing retention of parental murine sequences in the humanized 21M18 antibody. The cysteine residue at Kabat position 52a in CDR2 has been changed to a serine and a valine residue without loss of specific binding to Dll4 in 21M18 H7 and 21M18 H9, respectively. Substitutions within the framework region shown in 4A are numbered 1-6 with corresponding Kabat positions in the Vh chain 16, 20, 27, 28, 38, 48. B) Parental murine 21M18 antibody sequence (m-21M18-Vh, top) (SEQ ID NO:31), human germline Vh sequence (h-germline-Vh, middle) (SEQ ID NO:32), and the humanized 21M18 heavy chain variable region sequence (21M18-H2, bottom) (SEQ ID NO:33) are shown with conserved amino acid residues shaded in black. The three CDRs are marked showing retention of parental murine sequences in the humanized 21M18 antibody. The cysteine residue at Kabat position 52a in CDR2 has been changed to a serine and a valine residue without loss of specific binding to Dll4 in 21M18 H7 and 21M18 H9, respectively. The five retained murine residues within the variable framework region of all heavy chain variants are numbered 1-5 at their corresponding Kabat positions 20, 28, 38, 48, and 69.

The functionality of each candidate variant humanized heavy and light chain is tested by cotransfection into mammalian cells. Each of the five candidate humanized 21M18 heavy chains described above is cotransfected with the murine 21M18 light chain cDNA into HEK 293 cells, and conditioned media is assayed for DLL4 antigen binding activity by ELISA. The 21M18 heavy chain variant exhibiting the most robust binding is selected. This variant—"21M18 H2"—contains, in addition to murine CDRs, substitutions at 6 framework positions within the Vh framework, Kabat positions 16, 20, 27, 28, 38, and 48 (FIG. 4A). The 21M18 H2 humanized heavy chain is then cotransfected with each of the five candidate humanized light chains into HEK293 cells, and conditioned media is again assayed for antigen binding by ELISA. A single light chain variant is found to exhibit better binding than the other candidates—"21M18 L2"—retaining murine residues at Kabat positions 22 and 36 (FIG. 5).

Next, the isolated cysteine residue in CDR2H2 (SEQ ID NO: 2) is altered. Specifically, two heavy chain variants of H2 are synthesized with the cysteine residue at Kabat position 52a modified to a serine (variant H7; SEQ ID NO: 3) or a valine (variant H9; SEQ ID NO: 4) residue. These heavy chains are cotransfected into HEK293 cells with L2, and conditioned media again assayed. Both variants (21M18 H7L2 and 21M18 H9L2) demonstrate specific antigen binding by ELISA. Thus 21M18 heavy chain CDR2 comprises SEQ ID NO: 2, 3, or 4 in which the residue at Kabat position 52a comprises a cysteine, serine, or valine residue.

In certain embodiments, humanized antibodies against DLL4 were generated. The variable domains of the murine monoclonal antibody 21M18 were isolated and sequenced from the hybridoma line using degenerate PCR essentially as described in Larrick, J. M., et al., 1989, *Biochem. Biophys. Res. Comm.* 160: 1250 and Jones, S. T. & Bendig, M. M., 1991, *Bio/Technology* 9: 88. Human heavy and light chain variable framework regions most similar to the parental 21M18 antibody amino acid sequences were then chosen as the human framework regions for humanization. To identify the most similar human framework regions, the predicted protein sequences encoded by the $V_H$ and $V_L$ murine variable domains of 21M18 were compared with Ig variable domains encoded by the human genome using BLAST searches for human genomic sequence deposited in Genbank. Using this method, IGH(V)1-18 was chosen as the human heavy chain framework region and IGK(V)4-1 was chosen as the human light chain framework region.

The amino acid differences between the selected human framework IGH(V)1-18 heavy chain and the parent murine monoclonal antibody 21M18 heavy chain were identified, and a judgment was then made as to whether each difference in position contributed to proper folding of the 21M18 antibody. This analysis was guided by examination of solved crystal structures of other antibody fragments (e.g. the structure of fab 2E8 as described in Trakhanov et al, *Acta Crystallogr D Biol Crystallogr*, 1999, 55:122-28). Structures were modeled using computer software including Jmol, quick PDB, and Pymol. Consideration was given to the potential impact of an amino acid at a given position on the packing of the β-sheet framework, the interaction between the heavy and light chain variable domains, the degree of solvent exposure of the amino acid side chain, and the likelihood that an amino acid would impact the positioning of the CDR loops. From this analysis, five candidate $V_H$ chains fused in-frame to the human IgG2 constant region were chemically synthesized. The first candidate heavy chain comprised: i) a fully IGH(V) 1-18 human framework and ii) the parental 21M18 murine antibody CDRs (SEQ ID NOs: 1, 2, and 5). The four additional candidate heavy chains comprised: i) the IGH(V)1-18 human framework region with an increasing number of 21M18 murine residues retained in the framework region and ii) the parental 21M18 murine antibody CDRs (SEQ ID NOs: 1, 2, and 5).

Similarly, amino acid differences between the selected human framework IGK(V)4-1 light chain and the parent murine monoclonal antibody 21M18 light chain were identified, and a judgment was then made as to whether each difference in position contributed to proper folding of the 21M18 antibody. From this analysis, five candidate $V_L$ chains were chemically synthesized. The first candidate light chain comprised: i) a fully IGK(V)4-1 human framework and ii) the parental 21M18 murine antibody CDRs (SEQ ID NOs: 9, 10, and 11). The four additional candidate light chains comprised: i) the IGK(V)4-1 human framework region with an increasing number of 21M18 murine residues retained in the framework region and ii) the parental 21M18 murine antibody CDRs (SEQ ID NOs: 9, 10, and 11).

The functionality of each candidate variant humanized heavy and light chain was tested by cotransfection into mammalian cells. Each of the five candidate humanized 21M18 heavy chains described above was cotransfected with the murine 21M18 light chain cDNA into HEK 293 cells, and conditioned media was then assayed for DLL4 antigen binding activity by ELISA. The 21M18 heavy chain variant exhibiting the most robust binding was selected. This variant—"21M18 H2"—contained, in additional to murine CDRs, murine residues at five framework positions, Kabat positions 20, 28, 38, 48, and 69 (FIG. 4). The 21M18 H2 humanized heavy chain was then cotransfected with each of the five candidate humanized light chains into HEK293 cells, and conditioned media was again assayed for antigen binding by ELISA. A single light chain variant was found to exhibit better binding than the other candidates—"21M18 L2"—retaining murine residues at Kabat positions 22 and 36 (FIG. 5).

Next, the isolated cysteine residue in CDR2H2 (SEQ ID NO: 2) was altered. Specifically, two heavy chain variants of H2 were synthesized with the cysteine residue at Kabat position 52a modified to a serine (variant H7; SEQ ID NO: 3) or a valine (variant H9; SEQ ID NO: 4) residue. These heavy chains were cotransfected into HEK293 cells with L2, and conditioned media was again assayed. Both variants (21M18 H7L2 and 21M18 H9L2) demonstrated specific antigen binding by ELISA. Thus 21M18 heavy chain CDR2 comprises SEQ ID NO: 2, 3, or 4 in which the residue at Kabat position 52a comprises a cysteine, serine, or valine residue.

The humanized 21M18 antibodies were then further characterized. Specifically, the binding affinity of humanized 21M18 antibodies purified by protein A chromatography was determined using Biacore. Affinity was determined to be approximately 0.33 nM for 21M18 variant H2L2.

The humanized 21M18 antibodies were deposited with ATCC, located at 10801 University Blvd., Manassas, Va. 20110-2209, under the terms of the Budapest Treaty (21M18 H9L2, ATCC deposit no. PTA-8427 and 21M18 H7L2, ATCC deposit no. PTA-8425, deposited May 10, 2007).

Human Antibodies

In some embodiments, human antibodies that specifically recognize the extracellular domain of DLL4 are isolated using phage display technology. A synthetic antibody library containing human antibody variable domains is screened for specific and high affinity recognition of the DLL4 antigen described above. CDR cassettes in the library are specifically exchanged via unique flanking restriction sites for antibody optimization. Optimized human variable regions are then cloned into an Ig expression vector containing human $IgG_1$ heavy-chain and kappa light-chain for expression of human antibodies in mammalian CHO cells.

Example 2

In Vitro Assays to Evaluate Antibodies Against DLL4

This example describes representative in vitro assays to test the activity of antibodies generated against DLL4 on cell proliferation, Notch pathway activation, and cytotoxicity.

Proliferation Assay

The expression of DLL4 by different cancer cell lines is quantified using Taqman analysis. Cell lines identified as expressing DLL4 are plated at a density of $10^4$ cell per well in 96-well tissue culture microplates and allowed to spread for 24 hours. Subsequently cells are cultured for an additional 12 hours in fresh DMEM with 2% FCS at which point anti-DLL4 antibodies versus control antibodies are added to the culture medium in the presence of 10 µmol/L BrdU. Following BrdU labeling, the culture media is removed, and the cells fixed at room temperature for 30 minutes in ethanol and reacted for 90 minutes with peroxidase-conjugated monoclonal anti-BrdU antibody (clone BMG 6H8, Fab fragments). The substrate is developed in a solution containing tetramethylbenzidine and stopped after 15 minutes with 25 µl of 1 mol/L $H_2SO_4$. The color reaction is measured with an automatic ELISA plate reader using a 450 nm filter (UV Microplate Reader; Bio-Rad Laboratories, Richmond, Calif.). All experiments are performed in triplicate. The ability of anti-DLL4 antibodies to inhibit cell proliferation compared to control antibodies is determined.

Pathway Activation Assay

Figure 3E:
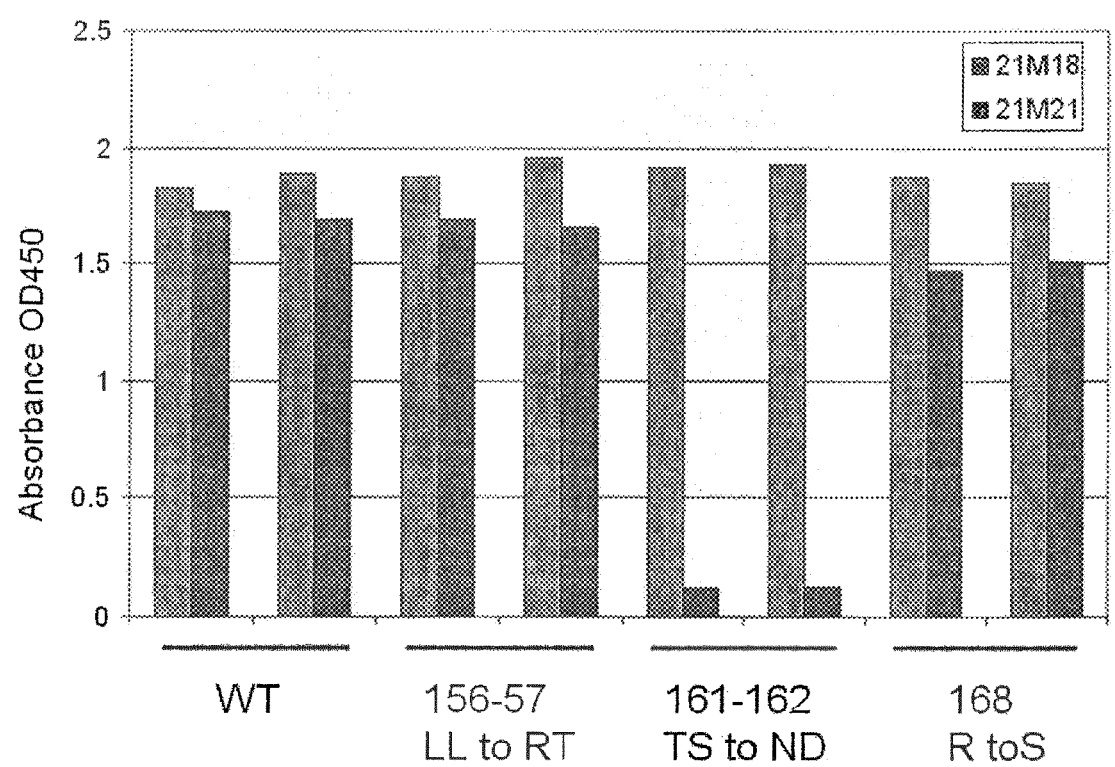

In certain embodiments, the ability of antibodies against DLL4 to block activation of the Notch signaling pathway is determined in vitro. HeLa cells cultured in DMEM supplemented with antibiotics and 10% FCS were co-transfected with 1) Hes1-Luc reporter vector containing the Hes1 promoter upstream of a firefly luciferase reporter gene to measure Notch signaling levels (Jarriault et al., 1995, *Nature* 377:355-8) in response to DLL4 ligand and 2) a *Renilla* luciferase reporter (Promega; Madison, Wis.) as an internal control for transfection efficiency. Transfected cells were then added to cultures plates coated overnight with 10 µg/ml DLL4-Fc protein. Antibodies to DLL4 were then added to the cell culture medium. Forty-eight hours following transfection, luciferase levels were measured using a dual luciferase assay kit (Promega; Madison, Wis.) with firefly luciferase activity normalized to *Renilla* luciferase activity. The ability of antibodies to inhibit DLL4 induced Notch pathway activation was thus determined. Inhibition of DLL4 activation of Notch pathway activation was observed with anti-DLL4 murine antibodies 21M14 and 21M18 (FIG. 6). In contrast, anti-DLL4 antibody 21M21 did not inhibit Notch binding (FIG. 6) despite binding to the DSL domain of DLL4 (FIG. 3E).

In certain embodiments, the ability of anti-DLL4 antibodies to modulate downstream gene activation was determined. C8 colon tumor cells from animals treated with murine 21M18 antibodies (described in detail below) were isolated and expression of Notch pathway genes HES1 and ATOH-1 was determined by RT-PCR. Total RNA from tumor tissue was isolated with RNeasy Fibrous Tissue kit (Qiagen, Valencia, Calif.) according to manufacturer's instructions. The quantity of RNA samples was determined by the ratio of 260 nm/280 nm. The integrity of RNA was determined by running an aliquot of the RNA sample on a denaturing agarose gel stained with ethidium bromide (EtBr). The ratio of 28s to 18s rRNA on the gel was visualized using a Fluor Chem camera delivered with the AphaEasa FC software. RNA samples were eluted in RNase-free water and stored at −80° C. The real-time RT-PCR was done with a dual-fluorescent nonextendable probe containing 3'-TAMRA FAM (6-carboxyfluorescein) reporter dye and a 3'-TAMRA (6-carboxy-tetramethylrhodamine). One hundred micrograms of total RNA was used for real-time PCR in a final volume of 25 uL containing reverse transcriptase, 1× Taqman buffer (Applied Biosystems, Foster City, Calif.) and the primer/probe mixture. Reactions were carried out in an ABI 7900 HT Fast Real Time PCR System (Applied Biosystems, Foster City, Calif.): 30 min at 48° C., 10 min at 95° C. and 40 cycles of 15 sec at 95° C. and 1 min at 60° C. The results were analyzed using the SDS2.3 software (Applied Biosystems). All primer and probe sets were obtained from Applied Biosystems (Foster City, Calif.). The level of expression of target genes were normalized to the expression level of the house keeping gene Gus B and expressed as relative quantity. Treatment with anti-DLL4 murine 21M18 antibodies reduced expression of HES1 and increased expression of ATOH-1 as compared to control treated tumors (FIG. 7A).

In some embodiments, mouse lineage-depleted OMP-C11 tumor cell colonies were established using culture conditions known to maintain tumorigenic cells in vitro. These tumor cell colonies were overlaid with 3T3 cells without (3T3) or including human DLL4 (DLL4) overexpressed on the cell surface in the presence or absence of 10 μg/mL murine 21M18 or 5 μM gamma-secretase inhibitor (GSI; i.e. DBZ). A no overlay control was also included. While 3T3-DLL4 cells induced HES1 and suppressed ATOH1 gene expression (shown as ratio of HES1:ATOH1), either 21M18 or GSI alone inhibited DLL4-induced Notch target gene changes.

Complement-Dependent Cytotoxicity Assay

In certain embodiments, cancer cell lines expressing DLL4 or cancer stem cells isolated from a patient sample passaged as a xenograft in immunocompromised mice (as described in detail below) are used to measure complement dependent cytotoxicity (CDC) mediated by an antibody against DLL4. Cells are suspended in 200 μl RPMI 1640 culture medium supplemented with antibiotics and 5% FBS at $10^6$ cells/ml. Suspended cells are then mixed with 200 μl serum or heat-inactivated serum with antibodies against DLL4 or control antibodies in triplicate. Cell mixtures are incubated for 1 to 4 hours at 37° C. in 5% $CO_2$. Treated cells are then collected, resuspended in 100 μl FITC-labeled annexin V diluted in culture medium and incubated at room temperature for 10 minutes. One hundred microliters of a propidium iodide solution (25 μg/ml) diluted in HBSS is added and incubated for 5 minutes at room temperature. Cells are collected, resuspended in culture medium and analyzed by flow cytometry. Flow cytometry of FITC stained cells provides total cell counts, and propidium iodide uptake by dead cells as a percentage of total cell numbers is used to measure cell death in the presence of serum and antibodies against DLL4 compared to heat-inactivated serum and control antibodies. The ability of anti-DLL4 antibodies to mediated complement-dependent cytotoxicity is thus determined.

Antibody-Dependent Cellular Cytotoxicity Assay

In certain embodiments, cancer cell lines expressing DLL4 or cancer stem cells isolated from a patients sample passaged as a xenograft in immunocompromised mice (as described in detail below) are used to measure antibody dependent cellular cytotoxicity (ADCC) mediated by an antibody against DLL4. Cells are suspended in 200 μl phenol red-free RPMI 1640 culture medium supplemented with antibiotics and 5% FBS at $10^6$ cells/ml. Peripheral blood mononuclear cells (PBMCs) are isolated from heparinized peripheral blood by Ficoll-Paque density gradient centrifugation for use as effector cells. Target cells (T) are then mixed with PBMC effector cells (E) at E/T ratios of 25:1, 10:1, and 5:1 in 96-well plates in the presence of at least one DLL4 antibody or a control antibody. Controls include incubation of target cells alone and effector cells alone in the presence of antibody. Cell mixtures are incubated for 1 to 6 hours at 37° C. in 5% $CO_2$. Released lactate dehydrogenase (LDH), a stable cytosolic enzyme released upon cell lysis, is then measured by a colorimetric assay (CytoTox96 Non-radioactive Cytotoxicity Assay; Promega; Madison, Wis.). Absorbance data at 490 nm are collected with a standard 96-well plate reader and background corrected. The percentage of specific cytotoxicity is calculated according to the formula: % cytotoxicity=100× (experimental LDH release−effector spontaneous LDH release−target spontaneous LDH release)/(target maximal LDH release−target spontaneous LDH release). The ability of antibodies against DLL4 to mediated antibody dependent cellular cytotoxicity is thus determined.

Example 3

In Vivo Prevention of Tumor Growth Using Anti-DLL4 Antibodies

This example describes the use of anti-DLL4 antibodies to prevent tumor growth in a xenograft model. In certain embodiments, tumor cells from a patient sample (solid tumor biopsy or pleural effusion) that have been passaged as a xenograft in mice are prepared for repassaging into experimental animals. Tumor tissue is removed under sterile conditions, cut up into small pieces, minced completely using sterile blades, and single cell suspensions obtained by enzymatic digestion and mechanical disruption. Specifically, pleural effusion cells or the resulting tumor pieces are mixed with ultra-pure collagenase III in culture medium (200-250 units of collagenase per mL) and incubated at 37° C. for 1-4 hours with pipetting up and down through a 10-mL pipette every 15-20 minutes. Digested cells are filtered through a 40 μM nylon mesh, washed with Hank's buffered saline solution (HBSS) containing 2% heat-inactivated calf serum (HICS) and 25 mM HEPES (pH 7.4). Dissociated tumor cells are then injected subcutaneously into the mammary fat pads of NOD/SCID mice to elicit tumor growth.

In certain embodiments, dissociated tumor cells are first sorted into tumorigenic and non-tumorigenic cells based on cell surface markers before injection into experimental animals. Specifically, tumor cells dissociated as described above are washed twice with Hepes buffered saline solution (HBSS) containing 2% heat-inactivated calf serum (HICS) and resuspended at $10^6$ cells per 100 μl. Antibodies are added and the cells incubated for 20 minutes on ice followed by two washes with HBSS/2% HICS. Antibodies include anti-ESA (Miltenyi Biotec, Auburn, Calif.), anti-CD44, anti-CD24, and Lineage markers anti-CD2, -CD3, -CD10, -CD16, -CD18, -CD31, -CD64, and -CD140b (collectively referred to as Lin; BD Biosciences, San Jose, Calif.). Antibodies are directly conjugated to fluorochromes to positively or negatively select cells expressing these markers. Mouse cells are eliminated by selecting against H2Kd+ and murine CD45+ cells, and dead cells are eliminated by using the viability dye DAPI. Flow cytometry is performed on a FACSAria (BD Biosciences, San Jose, Calif.). Side scatter and forward scatter profiles are used to eliminate cell clumps. Isolated ESA+, CD44+, CD24−/ low, Lin– tumorigenic cells are then injected subcutaneously into NOD/SCID mice to elicit tumor growth.

Figure 8:
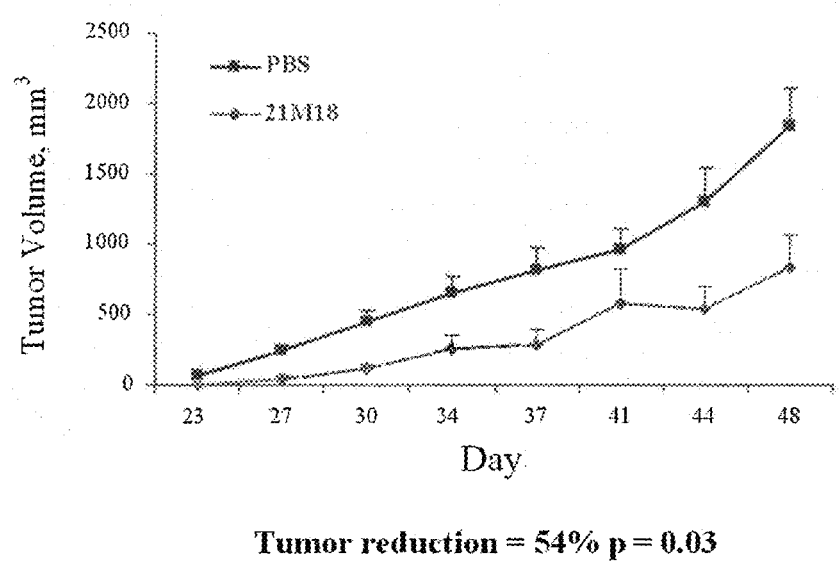
FIG. 8: DLL4 Antibodies Reduce Tumor Growth. NOD/SCID mice were injected with dissociated UM-C4 cells and treated with anti-DLL4 21M18 antibodies (n=5) or PBS (n=10). Treatment with 21M18 antibodies (diamonds) reduced tumor growth starting on day 23, and up to 54% reduction was observed by day 48 compared to PBS injected controls (black squares).

In certain embodiments, anti-DLL4 antibodies were analyzed for their ability to reduce the growth of UM-C4 colon tumor cells. Dissociated UM-C4 cells (10,000 per animal) were injected subcutaneously into the right flank region of 6-8 week old NOD/SCID mice. The day after tumor cell injection, animals were injected intraperitoneal (i.p.) with 10 mg/kg murine 21M18 anti-DLL4 antibodies (n=5) or PBS (n=10) two times per week for the duration of the experiment. Tumor growth was monitored weekly until growth was detected, after which point tumor growth was measured twice weekly for a total of 8 weeks. Treatment with 21M18 antibody reduced tumor growth by 54% compared to PBS injected controls (FIG. 8).

Figure 9:
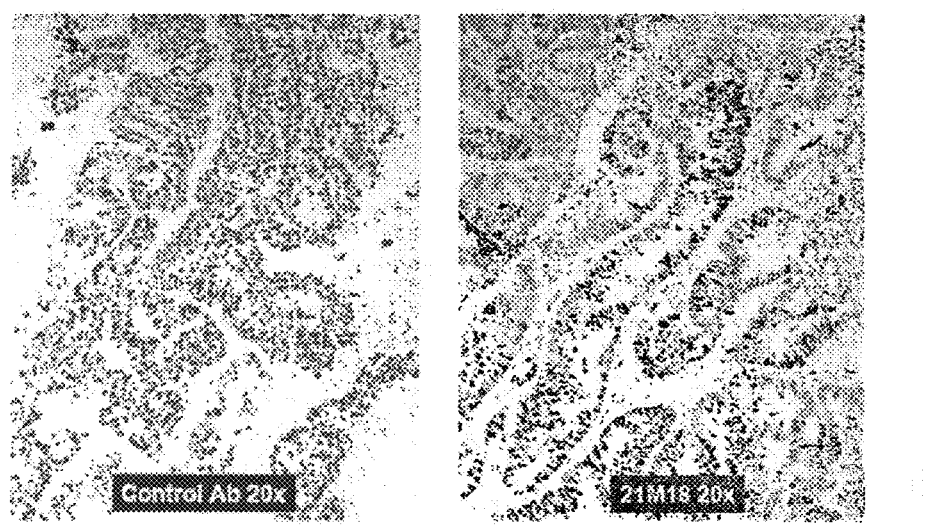
FIG. 9: Treatment with DLL4 Antibodies Reduces the Number of Proliferating Tumor Cells in Vivo. C8 Colon tumors treated with anti-DLL4 21M18 antibodies or control Ab were isolated. Immunocytochemistry with an antibody against Ki67 showed a reduction in the number of proliferating cells in 21M18 treated tumors compared to control.

The ability of anti-DLL4 antibodies to affect proliferation in vivo was then determined. C8 colon tumors from animals treated with murine 21M18 antibodies or control antibodies were isolated and expression of Ki67, a marker of cell proliferation, determined by immunocytochemistry. Specifically, formalin-fixed, paraffin-embedded tumors were cut into 4-um thick sections. Sections were deparaffinized in xylene and rehydrated in distilled water. Immunohistochemistry was performed according to standard methods. Briefly, sections were immersed in citrate buffer (pH 6) in a water bath for 20 minutes in the Decoking chamber to retrieve antigens. The slides were cooled for about 45 minutes and rinsed in PBS. Sections were incubated with hydrogen peroxide (Sigma-Aldrich, St Louis, Mo.) for 10 minutes at room temperature to remove endogenous peroxidase prior to addition of primary antibody. The rabbit anti-human Ki67 (Vector Laboratories Inc., Burlingame, Calif.) at 1:50 dilution in horse dilution buffer (1% NHS, 1% BSA, 0.1% Tx-100, 0.05% NaN3 in PBS) was added to each section and incubated for 1 hour or overnight at 4° C. Slides were rinsed 3 times in washing buffer (Gelatine 10%, Tx-100 10%, in PBS) for 5 minutes each. The anti-rabbit secondary antibody conjugated with HRP solution (Immpress anti-Rabbit pre-diluted, Vector Laboratories Inc., Burlingame, Calif.) was added to the slides and incubated for 30 minutes. After extensive wash with washing buffer, Vector Nova Red (Vector Laboratories Inc., Burlingame, Calif.) was added. The slides were rinsed with water, counterstained with hematoxilin and mounted with permanent mounting medium (Vectamount, Vector Laboratories Inc., Burlingame, Calif.). Treatment with anti-DLL4 murine 21M18 antibodies reduced the number of cells expressing Ki67 as compared to control treated tumors (FIG. 9).

Example 4

In Vivo Prevention and Treatment of Tumor Growth Using Anti-DLL4 Antibodies in Combination Therapy DLL-4 Antibodies in Combination with Fluorouracil In certain embodiments, anti-DLL4 antibodies were analyzed in combination with chemotherapy for the ability to reduce growth of UM-C4 colon tumor cells in vivo. Dissociated UM-C4 cells (10,000 per animal) were injected subcutaneously into the right flank region of 6-8 week old NOD/SCID mice. The day after tumor cell injection, animals were injected intraperitoneal (i.p.) with 10 mg/kg murine 21M18 anti-DLL4 antibodies or PBS two times per week for the duration of the experiment with or without concurrent treatment with the anti-metabolite chemotherapy agent fluorouracil (5-FU) administered one time per week. Tumor growth was monitored weekly until growth was detected, after which point tumor growth was measured twice weekly for a total of 8 weeks. Treatment with anti-DLL4 murine 21M18 antibodies in combination with 5-FU reduced tumor growth to a greater degree than either treatment alone (FIG. 10).

DLL-4 Antibodies in Combination with EGFR or VEGF Antibodies

Figure 11:
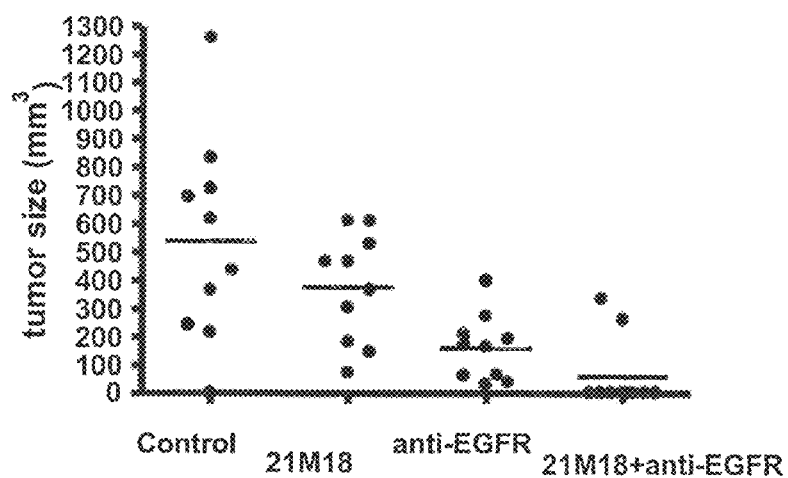
FIG. 11: Treatment with DLL4 Antibodies in Combination with anti-EGFR Antibodies Reduces Tumor Growth. NOD/SCID mice were injected with dissociated UM-C4 cells and treated with anti-DLL4 antibodies or PBS in the presence or absence of anti-EGFR antibodies. Plots of tumor measurements on day 46 from individual animals are shown. Each dot represents one animal. Treatment with 21M18 antibodies or anti-EGFR antibodies each reduced tumor size ($mm^3$) compared to control. Furthermore, combination treatment with 21M18 and anti-EGFR antibodies had an additive effect, reducing tumor size to less than ⅕ the size of control.

In certain embodiments, anti-DLL4 antibodies were tested in combination with anti-EGF receptor (EGFR) antibodies for the ability to affect tumor take frequency in vivo. Dissociated UM-C4 cells (10,000 per animal) were injected subcutaneously into the right flank region of 6-8 week old NOD/SCID mice. The day after tumor cell injection, animals (n=10) were injected intraperitoneal (i.p.) with 10 mg/kg murine 21M18 anti-DLL4 antibodies, anti-EGFR antibodies, a combination of anti-DLL4 and anti-EGFR antibodies, or PBS. Tumors were detected in all animals treated with anti-DLL4 or anti-EGFR antibodies and 9 out of 10 control animals. In contrast, only 2 out of 10 animals treated with a combination of anti-DLL4 and anti-EGFR antibodies had detectable tumors several weeks after treatment (FIG. 11). Furthermore, treatment with anti-DLL4 murine 21M18 antibodies in combination with anti-EGFR antibodies reduced the frequency of tumorigenesis versus either treatment alone (FIG. 11).

Figure 18:
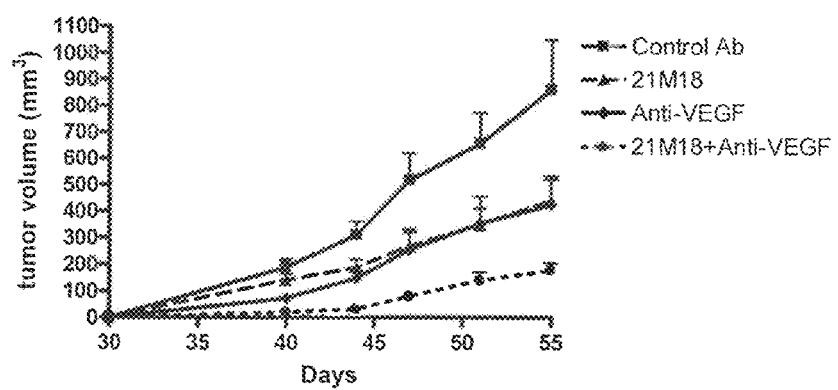
FIG. 18. Anti-DLL4 21M18 and anti-VEGF combination reduces tumor growth. C17 tumor cells were implanted and treatment was initiated two day later with either control antibody (black squares, solid line), 21M18 (triangles, dashed line), anti-VEGF (diamonds, solid line), or the combination of both antibodies (circles, dotted line). Each antibody was dosed at 10 mg/kg, given twice a week and there were 10 animals per group. Both 21M18 and anti-VEGF reduced tumor growth and the combination was more effective than either single antibody.

In certain embodiments, anti-DLL4 antibodies were tested in combination with anti-EGF receptor (EGFR) antibodies for the ability to affect tumor take frequency in vivo. C17 tumor cells were implanted in mice (n=10 per group) and treatment was initiated two day later with either control antibody, murine 21M18, anti-VEGF antibodies, or the combination of both antibodies. Each antibody was dosed at 10 mg/kg, given twice a week. Both 21M18 and anti-VEGF reduced tumor growth, and the combination was more effective than either antibody alone (FIG. 18).

DLL-4 Antibodies in Combination with Irinotecan

Figure 13A:
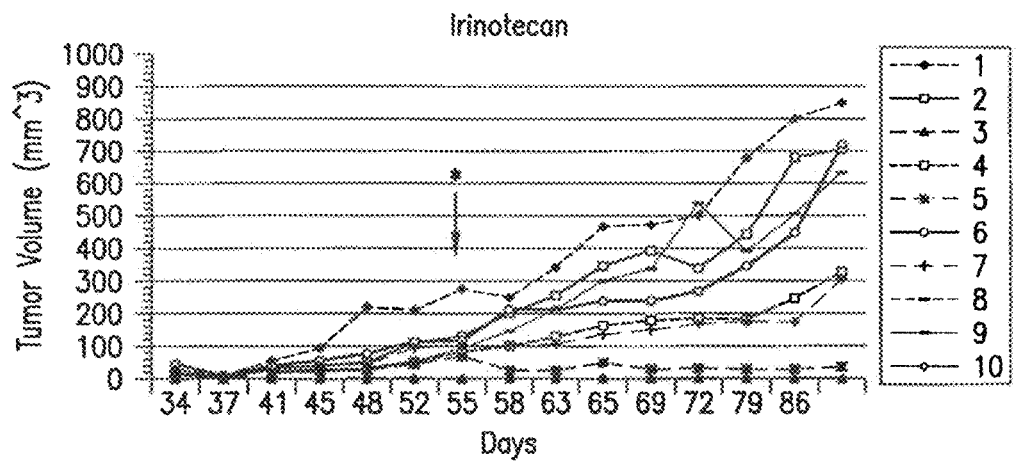
FIG. 13: Combination Anti-DLL4 21M18 and Irinotecan Treatment Prevents Colon Tumor Re-Growth. NOD/SCID mice were injected with dissociated C8 cells and treated with Irinotecan or Irinotecan in combination with anti-DLL4 21M18 antibodies (n=10 per group). A) Treatment with Irinotecan alone slowed colon tumor growth, but growth continued after cessation of treatment on day 56 (* arrow) in all but two treated animals. B) In contrast, treatment with a combination of Irinotecan and anti-DLL4 21M18 antibodies eliminated colon tumor growth both during treatment and for up to five weeks following cessation of treatment on day 56 in all ten treated animals. Each line represents the growth curve for an individual animal.
Figure 13B:
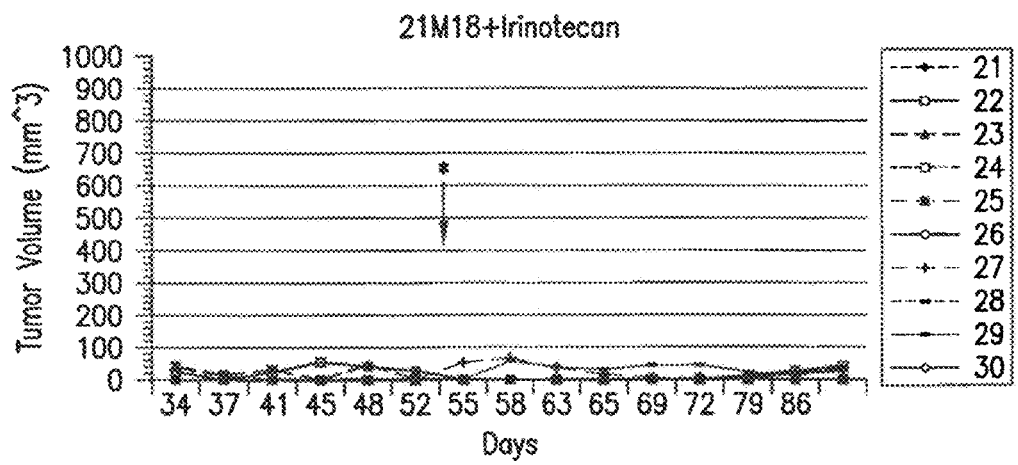

In certain embodiments, anti-DLL4 antibodies were tested in combination with the chemotherapeutic Irinotecan. In some embodiments, dissociated OMP-C8 tumor cells (10,000 per animal) were injected subcutaneously into the right flank region of 6-8 week old NOD/SCID mice. The day after tumor cell injection, animals were injected intraperitoneal (i.p.) with 10 mg/kg murine 21M18 anti-DLL4 antibodies or control antibody two times per week for the duration of the experiment with or without concurrent treatment with the chemotherapy agent Irinotecan administered one time per week at a dosage of 7.5 mg/kg. Tumor growth was monitored weekly until growth was detected, after which point tumor growth was measured twice weekly. Treatment with anti-DLL4 21M18 antibodies in combination with Irinotecan reduced tumor growth to a greater degree than either treatment alone (FIG. 12A). And, while tumor growth continued or accelerated in most animals after cessation of weekly treatment with 7.5 mg/kg Irinotecan alone, the combination of 10 mg/kg, twice per week, anti-DLL4 21M18 and 7.5 mg/kg weekly Irinotecan prevented further colon tumor growth after treatment cessation on day 56 for over five weeks (FIG. 13).

In certain embodiments, humanized H7L2 21M18 anti-DLL4 antibodies were tested in combination with Irinotecan. In some embodiments, dissociated C8 tumor cells (10,000 per animal) were injected subcutaneously into the right flank region of 6-8 week old NOD/SCID mice. The day after tumor cell injection, animals were injected intraperitoneal (i.p.) with 10 mg/kg humanized 21M18 anti-DLL4 antibodies, murine 21M18 antibodies, or control antibodies two times per week for the duration of the experiment with or without concurrent treatment with the chemotherapy agent Irinotecan administered one time per week at a dosage of 7.5 mg/kg.

Tumor growth was monitored weekly until growth was detected, after which point tumor growth was measured twice weekly. Treatment with humanized anti-DLL4 21M18 antibodies in combination with Irinotecan showed similar efficacy against tumor growth as murine 21M18 (FIG. 12B).

Figure 14:
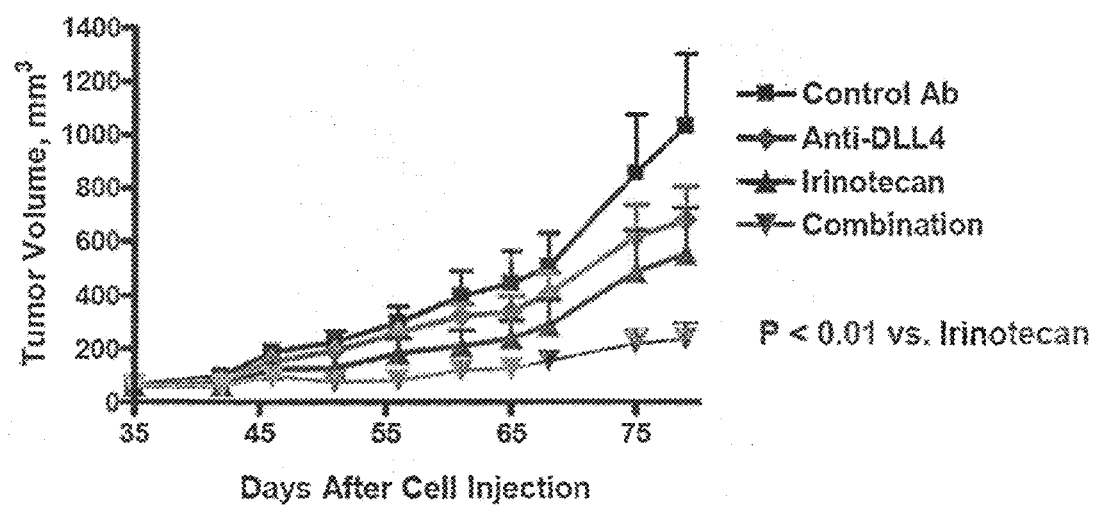
FIG. 14: Combination Anti-DLL4 21M18 and Irinotecan Treatment Inhibits the Growth of Established Colon Tumors More Effectively than Single Therapy Treatment. NOD/SCID mice were injected with dissociated C8 cells and treated with anti-DLL4 antibodies or control antibody in the presence or absence of Irinotecan. Treatment with 21M18 antibodies (diamonds) or Irinotecan (triangles) alone each reduced tumor volume (y-axis $mm^3$) compared to control treated animals (black squares). However, combination treatment with 21M18 plus Irinotecan (inverse triangles) inhibited tumor growth more effectively than either 21M18 or Irinotecan treatment alone.

In some embodiments, combination anti-DLL4 murine 21M18 and Irinotecan treatment was used to treat established colon tumors. Dissociated C8 cells (10,000 per animal) were injected subcutaneously into the right flank region of 6-8 week old NOD/SCID mice. When the injected cells produced tumors of approximately 60 mm$^3$, treatment was commenced. Animals were injected intraperitoneal (i.p.) with 10 mg/kg murine 21M18 anti-DLL4 antibodies or a control two times per week for the duration of the experiment with or without concurrent treatment with the chemotherapy agent Irinotecan administered one time per week at a dosage of 7.5 mg/kg. Treatment with anti-DLL4 murine 21M18 antibodies in combination with Irinotecan reduced the growth of established colon tumors to a greater degree than either treatment alone (FIG. 14).

Figure 16:
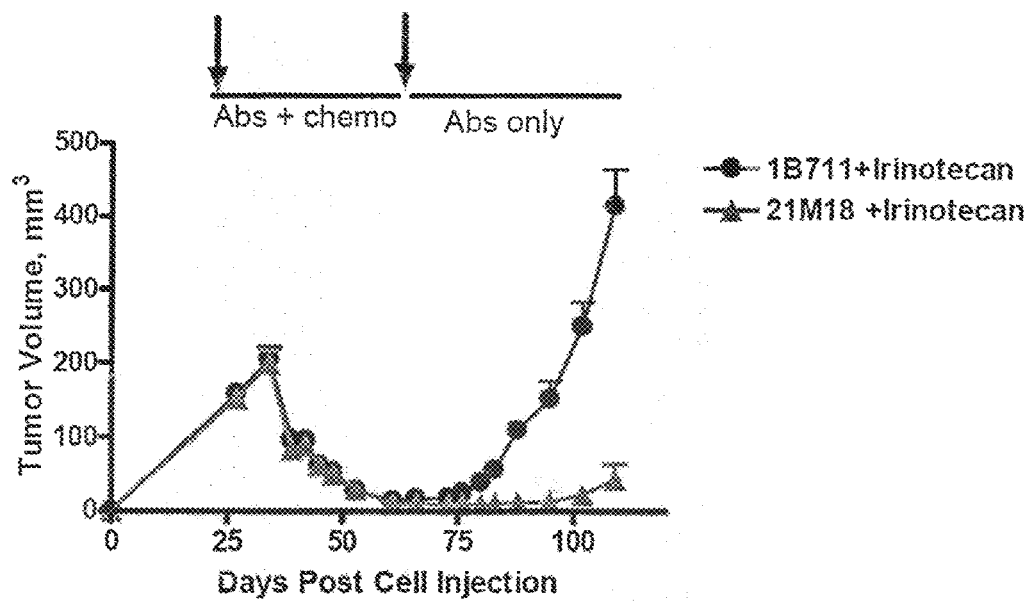
FIG. 16: Anti-DLL4 21M18 and Irinotecan Combination Treatment Delays Tumor Recurrence. Immunocompromised mice were injected with dissociated C8 cells and established tumors of approximately 150 $mm^3$ were treated with a combination of Irinotecan (45 mg/kg, dosed twice a week) with either anti-DLL4 21M18 antibodies or control antibodies for 32 days after which Irinotecan treatment was halted. Treatment with the either the control antibody or 21M18 continued. Reoccurrence of tumors by tumor volume (y-axis) was delayed in 21M18 treated animals (triangles) as compared to controls (circles).
Figure 17:
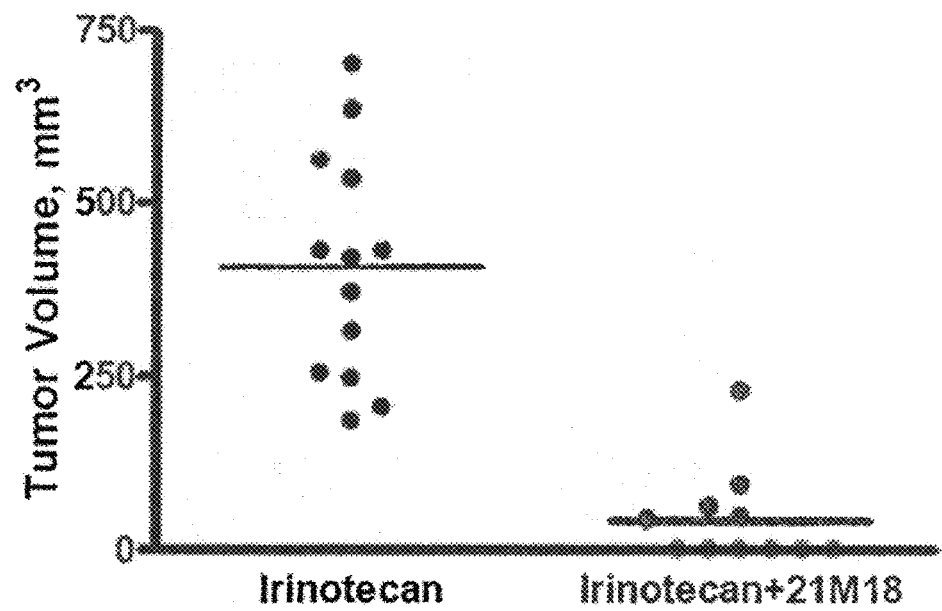
FIG. 17: Anti-DLL4 21M18 and Irinotecan Combination Treatment Delays Tumor Recurrence. The individual animals from the experiment shown in FIG. 16 are shown. The total tumor volume (y-axis) of each animal is shown 47 days after termination of Irinotecan treatment.

In some embodiments, combination therapy followed by antibody treatment delayed tumor recurrence. Dissociated C8 cells (10,000 per animal) were injected subcutaneously into the right flank region of 6-8 week old NOD/SCID mice. When the injected cells produced tumors of approximately 150 mm$^3$, treatment was commenced. Animals were administered intraperitoneal (i.p.) 10 mg/kg murine 21M18 anti-DLL4 or control antibodies two times per week in combination with Irinotecan at 7.5 mg/kg once weekly for a total of 32 days. Combination treatment was then discontinued and antibodies were treated with DLL4 21M18 or control antibodies for the remainder of the experiment. Treatment with anti-DLL4 21M18 antibodies following combination therapy significantly delayed the recurrence of tumor growth compared to control treated animals (FIG. 16). Individual tumor volume is also shown at 47 days after termination of Irinotecan treatment (FIG. 17).

DLL-4 Antibody Reduction of Cancer Stem Cell Frequency Is Enhanced by Irinotecan In certain embodiments, the ability of anti-DLL4 21M18 antibodies alone or in combination with Irinotecan to reduce the frequency of cancer stem cells was determined using a limiting dilution analysis. C8 colon tumors from mice treated with either control or DLL4 murine 21M18 antibodies, Irinotecan, or DLL4 murine 21M18 antibodies in combination with Irinotecan as described above were isolated after 38 days of treatment. Isolated tumors (n=3 per experimental group) were processed as described below. Tumors were removed, and minced with a sterile razor blade. To obtain single cell suspensions, a digestion solution containing Collagenase/Hyaluronidase:Dispase (1:1:8 of 10×) in MEBM medium (Cambrex, East Rutherford, N.J.) with a 1:100 dilution of DNAseI (Worthington, Lakewood, N.J.) was mixed with the tumor suspension and incubated for 1 hour at 37° C. Cells were centrifuged and resuspended in 1 ml of ACK medium (0.15M $NH_4Cl$, 10 mM $KHCO_3$, 0.1 mM $Na_2EDTA$ in distilled water) on ice for 2 minutes to remove red blood cells. Cells were centrifuged and resuspended at a concentration of 1×10$^7$ cells/ml in FACS buffer and then incubated with biotinylated mouse antibodies (α-mouse CD45-biotin 1:200 dilution and rat α-mouse $H_2Kd$-biotin 1:100 dilution, BioLegend, San Diego, Calif.) on ice for 30 minutes followed by addition of strepavadin magnetic beads (Invitrogen, Carlsbad, Calif.) to remove mouse cells. The remaining human cells in the suspension were collected, counted and diluted to the desired concentration for further use. Serial dilutions of human cells were then re-injected into immuno-compromised mice. Specifically, mice were injected with 900, 300, 100, or 50 isolated human tumor cells in the right flank region (n=10 per group). Tumor volume was assessed twice per week.

Figure 15A:
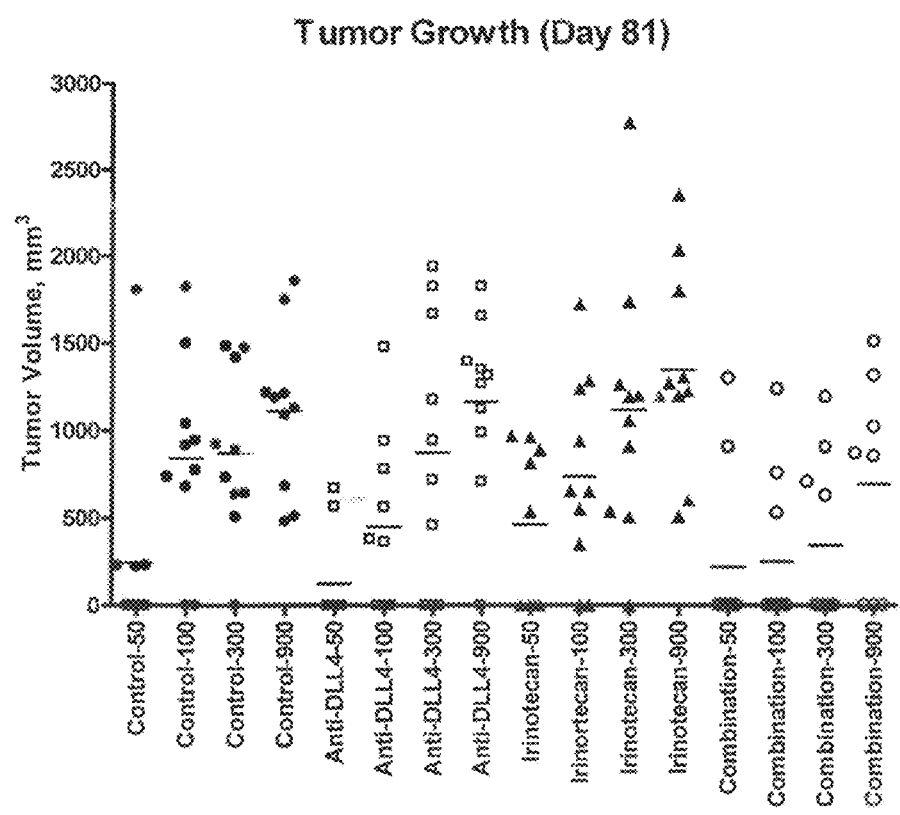
FIG. 15: Tumors Treated with Anti-DLL4 Antibodies Show Decreased Numbers of Tumorigenic Cells. Immunocompromised mice (n=10 per group) were injected with decreasing dosages of tumor cells from the experiment shown in FIG. 14 that had been treated with either control antibody, Irinotecan plus control antibody, DLL4 21M18 antibodies alone, or a combination of DLL4 21M18 antibodies and Irinotecan (Combination). A) Results of tumor take rates on day 81. Tumor volume ($mm^3$) was graphed compared to the number of human tumor cells injected: 900, 300, 100, and 50 for each treatment group. The number of animals with detectable tumors over the ten injected animals for each tumor cell dose is recorded below the graph of tumor volume for each cell dose with control treated tumor cells on the left (filled circles), anti-DLL4 21M18 antibody treated tumor cells second to the left (open squares), Irinotecan treated tumor cells second to the right (filled triangles), and Combination treated tumor cells on the right (open circles). B) The stem cell frequency on day 81 was calculated. The proportion of cancer stem cells (y-axis) from control treated (left) compared to anti-DLL4 treated (second from left), Irinotecan only treated (second from right), and Combination treated (right) tumor cells is plotted with the 95% confidence interval. The anti-DLL4 treated group has a statistically significant difference versus the control group (*) and the combination group is significantly different versus both the control (*) and Irinotecan alone groups (**).
Figure 15B:
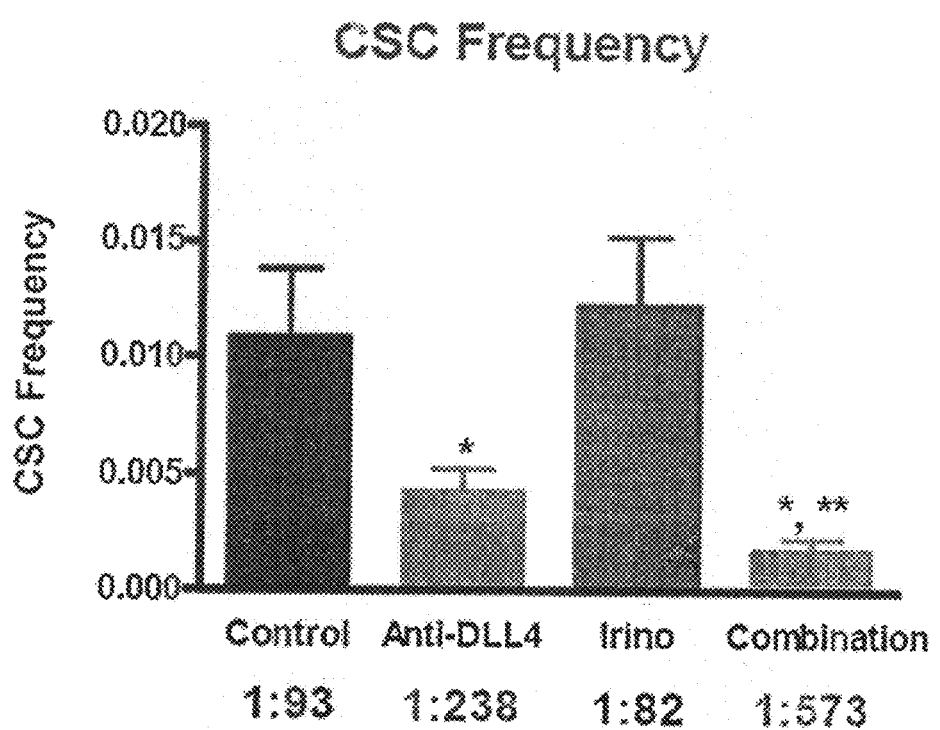

Upon termination of the study on day 81, the percentage of mice with detectable tumors was decreased in all groups injected with DLL4 21M18 antibody treated tumor cells and even further decreased in DLL4 21M18-Irinotecan treated tumor cells compared to those treated with either control or Irinotecan alone (FIG. 15A). Using these tumor generation frequencies, the stem cell frequency was calculated using Poisson statistics provided by L-Calc™ software. Briefly, based on Poisson distribution statistics, exactly one stem cell exists among the known number of injected cells if 37% of the animals fail to develop tumors. Treatment of tumors with Irinotecan alone increased the number of cancer stem cells from 1:93 in control treated tumors to 1:82. In contrast, anti-DLL4 antibodies reduced the cancer stem cell frequency from 1:93 in control treated tumors to 1:238 in DLL4 antibody treated tumors and to 1:573 in combination DLL4 21M18-Irinotecan treated tumor cells (FIG. 15B).

Example 5

In Vivo Treatment of Tumors Using Anti-DLL4 Antibodies

This example describes the use of humanized anti-DLL4 21M18 antibodies to treat cancer in a xenograft model. In certain embodiments, tumor cells from a patient sample (solid tumor biopsy or pleural effusion) that have been passaged as a xenograft in mice are prepared for repassaging into experimental animals. Tumor tissue is removed, cut up into small pieces, minced completely using sterile blades, and single cell suspensions obtained by enzymatic digestion and mechanical disruption. Dissociated tumor cells are then injected subcutaneously either into the mammary fat pads, for breast tumors, or into the flank, for non-breast tumors, of NOD/SCID mice to elicit tumor growth. Alternatively, ESA+, CD44+, CD24−/low, Lin− tumorigenic tumor cells are isolated as described in detail above and injected.

Following tumor cell injection, animals are monitored for tumor growth. Once tumors reach an average size of approximately 100 mm$^3$, antibody treatment begins. Each animal receives 100 μg DLL4 21M18 humanized antibodies or control antibodies i.p. two to five times per week for a total of 6 weeks. Tumor size is assessed twice a week during these 6 weeks. The ability of DLL4 humanized antibodies to prevent further tumor growth or to reduce tumor size compared to control antibodies is thus determined.

At the end point of antibody treatment, tumors are harvested for further analysis. In some embodiments a portion of the tumor is analyzed by immunofluorescence to assess antibody penetration into the tumor and tumor response. A portion of each harvested tumor from anti-DLL4 treated and control antibody treated mice is fresh-frozen in liquid nitrogen, embedded in O.C.T., and cut on a cryostat as 10 μm sections onto glass slides. In some embodiments, a portion of each tumor is formalin-fixed, paraffin-embedded, and cut on a microtome as 10 μm section onto glass slides. Sections are post-fixed and incubated with chromophore labeled antibodies that specifically recognize injected antibodies to detect anti-DLL4 receptor or control antibodies present in the tumor biopsy. Furthermore antibodies that detect different tumor and tumor-recruited cell types such as, for example, anti-VE cadherin (CD144) or anti-PECAM-1 (CD31) antibodies to detect vascular endothelial cells, anti-smooth muscle alpha-actin antibodies to detect vascular smooth muscle cells, anti- Ki67 antibodies to detect proliferating cells, TUNEL assays to detect dying cells, anti-intracellular domain (ICD) Notch fragment antibodies to detect Notch signaling can be used to assess the effects of antibody treatment on, for example, angiogenesis, tumor growth and tumor morphology.

In certain embodiments, the effect of anti-DLL4 humanized antibody treatment on tumor cell gene expression is also assessed. Total RNA is extracted from a portion of each harvested tumor from DLL4 antibody treated and control antibody treated mice and used for quantitative RT-PCR. Expression levels of DLL4, Notch receptors, components of the Notch signaling pathway, as well as addition cancer stem cell markers previously identified (e.g. CD44) are analyzed relative to the house-keeping gene GAPDH as an internal control. Changes in tumor cell gene expression upon DLL4 antibody treatment are thus determined.

In addition, the effect of anti-DLL4 antibody treatment on the presence of cancer stem cells in a tumor is assessed. Tumor samples from DLL4 versus control antibody treated mice are cut up into small pieces, minced completely using sterile blades, and single cell suspensions obtained by enzymatic digestion and mechanical disruption. Dissociated tumor cells are then analyzed by FACS analysis for the presence of tumorigenic cancer stem cells based on ESA+, CD44+, CD24−/low, Lin− surface cell marker expression as described in detail above.

The tumorigenicity of cells isolated based on ESA+, CD44+, CD24−/low, Lin− expression following anti-DLL4 antibody treatment can then assessed. ESA+, CD44+, CD24−/low, Lin− cancer stem cells isolated from DLL4 antibody treated versus control antibody treated mice are re-injected subcutaneously into the mammary fat pads of NOD/SCID mice. The tumorigenicity of cancer stem cells based on the number of injected cells required for consistent tumor formation is then determined.

Example 6

Treatment of Human Cancer Using Humanized Anti-DLL4 Antibodies

This example describes methods for treating cancer using humanized antibodies against DLL4 to target tumors comprising cancer stem cells and/or tumor cells in which Notch receptor or Notch receptor ligand expression has been detected. The presence of cancer stem cell marker expression can first be determined from a tumor biopsy. Tumor cells from a biopsy from a patient diagnosed with cancer are removed under sterile conditions. In some embodiments the tissue biopsy is fresh-frozen in liquid nitrogen, embedded in O.C.T., and cut on a cryostat as 10 µm sections onto glass slides. In some embodiments, the tissue biopsy is formalin-fixed, paraffin-embedded, and cut on a microtome as 10 µm section onto glass slides. Sections are incubated with antibodies against DLL4 to detect protein expression.

The presence of cancer stem cells can also be determined. Tissue biopsy samples are cut up into small pieces, minced completely using sterile blades, and cells subject to enzymatic digestion and mechanical disruption to obtain a single cell suspension. Dissociated tumor cells are then incubated with anti-ESA, -CD44, -CD24, -Lin, and -DLL4 antibodies to detect cancer stem cells, and the presence of ESA+, CD44+, CD24−/low, Lin−, DLL4+ tumor stem cells is determined by flow cytometry as described in detail above.

Cancer patients whose tumors are diagnosed as expressing a Notch receptor or Notch receptor ligand are treated with humanized anti-DLL4 antibodies. In certain embodiments, humanized anti-DLL4 antibodies generated as described above are purified and formulated with a suitable pharmaceutical vehicle for injection. In some embodiments, patients are treated with the DLL4 antibodies at least once a month for at least 10 weeks. In some embodiments, patients are treated with the DLL4 antibodies at least once a week for at least about 14 weeks. Each administration of the antibody should be a pharmaceutically effective dose. In some embodiments, between about 2 to about 100 mg/ml of an anti-DLL4 antibody is administered. In some embodiments, between about 5 to about 40 mg/ml of an anti-DLL4 antibody is administered. The antibody can be administered prior to, concurrently with, or after standard radiotherapy regimens or chemotherapy regimens using one or more chemotherapeutic agent, such as oxaliplatin, fluorouracil, leucovorin, or streptozocin. Patients are monitored to determine whether such treatment has resulted in an anti-tumor response, for example, based on tumor regression, reduction in the incidences of new tumors, lower tumor antigen expression, decreased numbers of cancer stem cells, or other means of evaluating disease prognosis.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims. All publications, patents and patent applications cited herein are incorporated by reference in their entirety into the disclosure.

What is claimed is:

1. A method of inhibiting tumor growth in a subject, comprising administering to the subject a therapeutically effective amount of a monoclonal antibody that specifically binds human delta-like ligand 4 (DLL4), wherein the antibody is selected from the group consisting of:
   a) an antibody comprising:
      i. a heavy chain variable region comprising CDR amino acid sequences CDR1 (SEQ ID NO:1); CDR2 (SEQ ID NO:2, SEQ ID NO:3, or SEQ ID NO:4); and CDR3 (SEQ ID NO:5), and
      ii. a light chain variable region comprising CDR amino acid sequences CDR1 (SEQ ID NO:9); CDR2 (SEQ ID NO:10); and CDR3 (SEQ ID NO:11); and
   b) an antibody comprising:
      i. a heavy chain variable region comprising amino acids selected from the group consisting of: SEQ ID NO:6, SEQ ID NO:7, and SEQ ID NO:8, or
      ii. a light chain variable region comprising SEQ ID NO:12.

2. The method of claim 1, wherein the antibody comprises:
   a) a heavy chain variable region comprising CDR amino acid sequences CDR1 (SEQ ID NO:1), CDR2 (SEQ ID NO:3), and CDR3 (SEQ ID NO:5), and
   b) a light chain variable region comprises CDR amino acid sequences CDR1 (SEQ ID NO: 9); CDR2 (SEQ ID NO:10); and CDR3 (SEQ ID NO:11).

3. The method of claim 1, wherein the antibody comprises a heavy chain variable region comprising SEQ ID NO:7 and a light chain variable region comprising SEQ ID NO:12.

4. A method of treating cancer in a subject, comprising administering to the subject a therapeutically effective amount of a monoclonal antibody that specifically binds DLL4, wherein the antibody is selected from the group consisting of:

a) an antibody comprising:
  i. a heavy chain variable region comprising CDR amino acid sequences CDR1 (SEQ ID NO:1); CDR2 (SEQ ID NO:2, SEQ ID NO:3, or SEQ ID NO:4); and CDR3 (SEQ ID NO:5), and
  ii. a light chain variable region comprising CDR amino acid sequences CDR1 (SEQ ID NO:9); CDR2 (SEQ ID NO:10); and CDR3 (SEQ ID NO:11); and
b) an antibody comprising:
  i. a heavy chain variable region comprising amino acids selected from the group consisting of: SEQ ID NO:6, SEQ ID NO:7, and SEQ ID NO:8, or
  ii. a light chain variable region comprising SEQ ID NO:12.

5. The method of claim 4, wherein the antibody comprises:
a) a heavy chain variable region comprising CDR amino acid sequences CDR1 (SEQ ID NO:1), CDR2 (SEQ ID NO:3), and CDR3 (SEQ ID NO:5), and
b) a light chain variable region comprises CDR amino acid sequences CDR1 (SEQ ID NO: 9); CDR2 (SEQ ID NO:10); and CDR3 (SEQ ID NO:11).

6. The method of claim 5, wherein the antibody comprises a heavy chain variable region comprising SEQ ID NO:7.

7. The method of claim 5, wherein the antibody comprises a light chain variable region comprising SEQ ID NO:12.

8. The method of claim 5, wherein the antibody comprises a heavy chain variable region comprising SEQ ID NO:7, and a light chain variable region comprising SEQ ID NO:12.

9. The method of claim 8, wherein the antibody is a chimeric, bispecific, or humanized antibody.

10. The method of claim 8, wherein the antibody is a humanized antibody.

11. The method of claim 8, wherein the cancer is colorectal cancer, breast cancer, lung cancer, ovarian cancer, liver cancer, prostate cancer, kidney cancer, or pancreatic cancer.

12. The method of claim 11, wherein the cancer is lung cancer.

13. The method of claim 12, wherein the lung cancer is non-small cell lung cancer.

14. The method of claim 11, wherein the cancer is pancreatic cancer.

15. The method of claim 14, where the pancreatic cancer is metastatic.

16. The method of claim 11, wherein the cancer is ovarian cancer.

17. The method of claim 11, wherein the cancer is breast cancer.

18. The method of claim 4, wherein the antibody is an antigen-binding fragment.

19. The method of claim 4, wherein the antibody is a chimeric, bispecific, or humanized antibody.

20. The method of claim 19, wherein the antibody is a humanized antibody.

21. The method of claim 4, wherein the antibody is an IgG antibody.

22. The method of claim 21, wherein the antibody is an $IgG_2$ antibody.

23. The method of claim 21, wherein the antibody is an $IgG_1$ antibody.

24. The method of claim 20, wherein the antibody is an $IgG_2$ antibody.

25. The method of claim 20, wherein the antibody is an $IgG_1$ antibody.

26. The method of claim 4, wherein the cancer is colorectal cancer, breast cancer, lung cancer, ovarian cancer, liver cancer, prostate cancer, kidney cancer, or pancreatic cancer.

27. The method of claim 2, wherein the antibody is a chimeric, bispecific, or humanized antibody.

28. The method of claim 27, wherein the antibody is a humanized antibody.

29. The method of claim 4, further comprising administering a second therapeutic agent to the subject.

30. The method of claim 29, wherein the second therapeutic agent is a chemotherapeutic agent.

31. The method of claim 29, wherein the second therapeutic agent is a second therapeutic antibody.

32. The method of claim 29, wherein the second therapeutic agent is radiation therapy.

\* \* \* \* \*

SEQUENCE LISTING

```
<160> NUMBER OF SEQ ID NOS: 36

<210> SEQ ID NO 1
<211> LENGTH: 6
<212> TYPE: PRT
<213> ORGANISM: Artificial Sequence
<220> FEATURE:
<223> OTHER INFORMATION: Murine Heavy Chain CDR1

<400> SEQUENCE: 1

Thr Ala Tyr Tyr Ile His
1               5

<210> SEQ ID NO 2
<211> LENGTH: 17
```

-continued

```
<212> TYPE: PRT
<213> ORGANISM: Artificial Sequence
<220> FEATURE:
<223> OTHER INFORMATION: Murine Heavy Chain CDR2, H2

<400> SEQUENCE: 2

Tyr Ile Ser Cys Tyr Asn Gly Ala Thr Asn Tyr Asn Gln Lys Phe Lys
1               5                   10                  15

Gly

<210> SEQ ID NO 3
<211> LENGTH: 17
<212> TYPE: PRT
<213> ORGANISM: Artificial Sequence
<220> FEATURE:
<223> OTHER INFORMATION: Murine Heavy Chain CDR2, H7

<400> SEQUENCE: 3

Tyr Ile Ser Ser Tyr Asn Gly Ala Thr Asn Tyr Asn Gln Lys Phe Lys
1               5                   10                  15

Gly

<210> SEQ ID NO 4
<211> LENGTH: 17
<212> TYPE: PRT
<213> ORGANISM: Artificial Sequence
<220> FEATURE:
<223> OTHER INFORMATION: Murine Heavy Chain CDR2, H9

<400> SEQUENCE: 4

Tyr Ile Ser Val Tyr Asn Gly Ala Thr Asn Tyr Asn Gln Lys Phe Lys
1               5                   10                  15

Gly

<210> SEQ ID NO 5
<211> LENGTH: 11
<212> TYPE: PRT
<213> ORGANISM: Artificial Sequence
<220> FEATURE:
<223> OTHER INFORMATION: Murine Heavy Chain CDR3

<400> SEQUENCE: 5

Arg Asp Tyr Asp Tyr Asp Val Gly Met Asp Tyr
1               5                   10

<210> SEQ ID NO 6
<211> LENGTH: 119
<212> TYPE: PRT
<213> ORGANISM: Artificial Sequence
<220> FEATURE:
<223> OTHER INFORMATION: Murine Heavy Chain Variable Region, H2

<400> SEQUENCE: 6

Gln Val Gln Leu Val Gln Ser Gly Ala Glu Val Lys Lys Pro Gly Ala
1               5                   10                  15

Ser Val Lys Ile Ser Cys Lys Ala Ser Gly Tyr Ser Phe Thr Ala Tyr
                20                  25                  30

Tyr Ile His Trp Val Lys Gln Ala Pro Gly Gln Gly Leu Glu Trp Ile
            35                  40                  45

Gly Tyr Ile Ser Cys Tyr Asn Gly Ala Thr Asn Tyr Asn Gln Lys Phe
        50                  55                  60

Lys Gly Arg Val Thr Phe Thr Thr Asp Thr Ser Thr Ser Thr Ala Tyr
65                  70                  75                  80
```

```
Met Glu Leu Arg Ser Leu Arg Ser Asp Asp Thr Ala Val Tyr Tyr Cys
                85                  90                  95

Ala Arg Asp Tyr Asp Tyr Asp Val Gly Met Asp Tyr Trp Gly Gln Gly
            100                 105                 110

Thr Leu Val Thr Val Ser Ser
        115
```

<210> SEQ ID NO 7
<211> LENGTH: 119
<212> TYPE: PRT
<213> ORGANISM: Artificial Sequence
<220> FEATURE:
<223> OTHER INFORMATION: Murine Heavy Chain Variable Region, H7

<400> SEQUENCE: 7

```
Gln Val Gln Leu Val Gln Ser Gly Ala Glu Val Lys Lys Pro Gly Ala
1               5                   10                  15

Ser Val Lys Ile Ser Cys Lys Ala Ser Gly Tyr Ser Phe Thr Ala Tyr
            20                  25                  30

Tyr Ile His Trp Val Lys Gln Ala Pro Gly Gln Gly Leu Glu Trp Ile
        35                  40                  45

Gly Tyr Ile Ser Ser Tyr Asn Gly Ala Thr Asn Tyr Asn Gln Lys Phe
    50                  55                  60

Lys Gly Arg Val Thr Phe Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Tyr Asp Tyr Asp Val Gly Met Asp Tyr Trp Gly Gln Gly
            100                 105                 110

Thr Leu Val Thr Val Ser Ser
        115
```

<210> SEQ ID NO 8
<211> LENGTH: 119
<212> TYPE: PRT
<213> ORGANISM: Artificial Sequence
<220> FEATURE:
<223> OTHER INFORMATION: Murine Heavy Chain Variable Region, H9

<400> SEQUENCE: 8

```
Gln Val Gln Leu Val Gln Ser Gly Ala Glu Val Lys Lys Pro Gly Ala
1               5                   10                  15

Ser Val Lys Ile Ser Cys Lys Ala Ser Gly Tyr Ser Phe Thr Ala Tyr
            20                  25                  30

Tyr Ile His Trp Val Lys Gln Ala Pro Gly Gln Gly Leu Glu Trp Ile
        35                  40                  45

Gly Tyr Ile Ser Val Tyr Asn Gly Ala Thr Asn Tyr Asn Gln Lys Phe
    50                  55                  60

Lys Gly Arg Val Thr Phe Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Tyr Asp Tyr Asp Val Gly Met Asp Tyr Trp Gly Gln Gly
            100                 105                 110

Thr Leu Val Thr Val Ser Ser
        115
```

<210> SEQ ID NO 9
<211> LENGTH: 15
<212> TYPE: PRT
<213> ORGANISM: Artificial Sequence
<220> FEATURE:
<223> OTHER INFORMATION: Murine Light Chain CDR1

<400> SEQUENCE: 9

Arg Ala Ser Glu Ser Val Asp Asn Tyr Gly Ile Ser Phe Met Lys
1               5                   10                  15

<210> SEQ ID NO 10
<211> LENGTH: 7
<212> TYPE: PRT
<213> ORGANISM: Artificial Sequence
<220> FEATURE:
<223> OTHER INFORMATION: Murine Light Chain CDR2

<400> SEQUENCE: 10

Ala Ala Ser Asn Gln Gly Ser
1               5

<210> SEQ ID NO 11
<211> LENGTH: 12
<212> TYPE: PRT
<213> ORGANISM: Artificial Sequence
<220> FEATURE:
<223> OTHER INFORMATION: Murine Light Chain CDR3

<400> SEQUENCE: 11

Gln Gln Ser Lys Glu Val Pro Trp Thr Phe Gly Gly
1               5                   10

<210> SEQ ID NO 12
<211> LENGTH: 111
<212> TYPE: PRT
<213> ORGANISM: Artificial Sequence
<220> FEATURE:
<223> OTHER INFORMATION: Murine Light Chain Variable Region

<400> SEQUENCE: 12

Asp Ile Val Met Thr Gln Ser Pro Asp Ser Leu Ala Val Ser Leu Gly
1               5                   10                  15

Glu Arg Ala Thr Ile Ser Cys Arg Ala Ser Glu Ser Val Asp Asn Tyr
                20                  25                  30

Gly Ile Ser Phe Met Lys Trp Phe Gln Gln Lys Pro Gly Gln Pro Pro
            35                  40                  45

Lys Leu Leu Ile Tyr Ala Ala Ser Asn Gln Gly Ser Gly Val Pro Asp
        50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Lys
                85                  90                  95

Glu Val Pro Trp Thr Phe Gly Gly Gly Thr Lys Val Glu Ile Lys
            100                 105                 110

<210> SEQ ID NO 13
<211> LENGTH: 414
<212> TYPE: DNA
<213> ORGANISM: Artificial Sequence
<220> FEATURE:
<223> OTHER INFORMATION: Murine Nucleotide Sequence of Heavy Chain, H2
      Variable Region

<400> SEQUENCE: 13

| | | |
|---|---|---|
| atggactgga cctggagcat cctgttcctg gtggctgctg ctacaggagc tcactcccag | 60 | |
| gttcagctgg tgcagtctgg agctgaggtg aagaagcctg gggctagcgt gaagatcagc | 120 | |
| tgcaaggcta gcggatactc ctttacagct tactacatcc actgggtgaa gcaggcccct | 180 | |
| ggacaagggc tggagtggat cggatatatc agctgttaca acggagctac aaactacaac | 240 | |
| cagaagttca agggcagggt caccttcaca acagacacaa gcacaagcac agcctacatg | 300 | |
| gagctgagga gcctgagaag cgacgacaca gccgtgtact actgtgctag ggactacgac | 360 | |
| tacgacgtgg ggatggacta ctggggccaa ggaaccctgg tcaccgtcag ctca | 414 | |

<210> SEQ ID NO 14
<211> LENGTH: 414
<212> TYPE: DNA
<213> ORGANISM: Artificial Sequence
<220> FEATURE:
<223> OTHER INFORMATION: Murine Nucleotide Sequence of Heavy Chain, H7
      Variable Region

<400> SEQUENCE: 14

| | | |
|---|---|---|
| atggactgga cctggagcat cctgttcctg gtggctgctg ctacaggagc tcactcccag | 60 | |
| gttcagctgg tgcagtctgg agctgaggtg aagaagcctg gggctagcgt gaagatcagc | 120 | |
| tgcaaggcta gcggatactc ctttacagct tactacatcc actgggtgaa gcaggcccct | 180 | |
| ggacaagggc tggagtggat cggatatatc agctcctaca acggagctac aaactacaac | 240 | |
| cagaagttca agggcagggt caccttcaca acagacacaa gcacaagcac agcctacatg | 300 | |
| gagctgagga gcctgagaag cgacgacaca gccgtgtact actgtgctag ggactacgac | 360 | |
| tacgacgtgg ggatggacta ctggggccaa ggaaccctgg tcaccgtcag ctca | 414 | |

<210> SEQ ID NO 15
<211> LENGTH: 414
<212> TYPE: DNA
<213> ORGANISM: Artificial Sequence
<220> FEATURE:
<223> OTHER INFORMATION: Murine Nucleotide Sequence of Heavy Chain, H9

<400> SEQUENCE: 15

| | | |
|---|---|---|
| atggactgga cctggagcat cctgttcctg gtggctgctg ctacaggagc tcactcccag | 60 | |
| gttcagctgg tgcagtctgg agctgaggtg aagaagcctg gggctagcgt gaagatcagc | 120 | |
| tgcaaggcta gcggatactc ctttacagct tactacatcc actgggtgaa gcaggcccct | 180 | |
| ggacaagggc tggagtggat cggatatatc agcgtctaca acggagctac aaactacaac | 240 | |
| cagaagttca agggcagggt caccttcaca acagacacaa gcacaagcac agcctacatg | 300 | |
| gagctgagga gcctgagaag cgacgacaca gccgtgtact actgtgctag ggactacgac | 360 | |
| tacgacgtgg ggatggacta ctggggccaa ggaaccctgg tcaccgtcag ctca | 414 | |

<210> SEQ ID NO 16
<211> LENGTH: 717
<212> TYPE: DNA
<213> ORGANISM: Artificial Sequence
<220> FEATURE:
<223> OTHER INFORMATION: Murine Nucleotide Sequence of Light Chain

<400> SEQUENCE: 16

| | | |
|---|---|---|
| atggtgctcc agacccaggt cttcatttcc ctgctgctct ggatcagcgg agcctacggg | 60 | |
| gacatcgtga tgacccagtc ccctgactcc ctggctgtgt ccctgggcga gagggccacc | 120 | |
| atctcctgca gagccagcga atccgtcgat aattatggca tttccttttat gaagtggttc | 180 |

```
cagcagaaac caggacagcc tcctaagctg ctcatttacg ctgcatccaa ccaagggtcc    240
ggggtccctg acaggttctc cggcagcggg tccggaacag atttcactct caccatcagc    300
agcctgcagg ctgaagatgt ggctgtctat tactgtcagc aaagcaagga ggtgccttgg    360
acattcggag agggaccaa ggtggaaatc aaacgtacgg tggctgcccc ctccgtcttc     420
atcttccccc ccagcgatga gcagctgaaa agcggcactg ccagcgtggt gtgcctgctg    480
aataacttct atcccgggag gccaaagtg cagtggaagg tggataacgc cctccaaagc     540
ggcaactccc aggagagcgt cacagagcag gacagcaagg acagcaccta cagcctcagc    600
agcaccctga ccctgagcaa agccgactac gagaaacaca agtctacgc ctgcgaagtc     660 acccatcagg gcctgagcag ccccgtcaca aagagcttca caggggcga gtgttga       717
```

<210> SEQ ID NO 17
<211> LENGTH: 18
<212> TYPE: DNA
<213> ORGANISM: Artificial Sequence
<220> FEATURE:
<223> OTHER INFORMATION: Murine Nucleotide Sequence of Heavy Chain CDR1

<400> SEQUENCE: 17

```
acagcttact acatccac                                                   18
```

<210> SEQ ID NO 18
<211> LENGTH: 50
<212> TYPE: DNA
<213> ORGANISM: Artificial Sequence
<220> FEATURE:
<223> OTHER INFORMATION: Murine Nucleotide Sequence of Heavy Chain CDR2,
      H2

<400> SEQUENCE: 18

```
atatcagctg ttacaacgga gctacaaact acaaccagaa gttcaagggc               50
```

<210> SEQ ID NO 19
<211> LENGTH: 50
<212> TYPE: DNA
<213> ORGANISM: Artificial Sequence
<220> FEATURE:
<223> OTHER INFORMATION: Murine Nucleotide Sequence of Heavy Chain CDR2,
      H7

<400> SEQUENCE: 19

```
atatcagctc ctacaacgga gctacaaact acaaccagaa gttcaagggc               50
```

<210> SEQ ID NO 20
<211> LENGTH: 50
<212> TYPE: DNA
<213> ORGANISM: Artificial Sequence
<220> FEATURE:
<223> OTHER INFORMATION: Murine Nucleotide Sequence of Heavy Chain CDR2,
      H9

<400> SEQUENCE: 20

```
atatcagcgt ctacaacgga gctacaaact acaaccagaa gttcaagggc               50
```

<210> SEQ ID NO 21
<211> LENGTH: 33
<212> TYPE: DNA
<213> ORGANISM: Artificial Sequence
<220> FEATURE:
<223> OTHER INFORMATION: Murine Nucleotide Sequence of Heavy Chain CDR3

<400> SEQUENCE: 21

```
agggactacg actacgacgt ggggatggac tac                                    33
```

<210> SEQ ID NO 22
<211> LENGTH: 45
<212> TYPE: DNA
<213> ORGANISM: Artificial Sequence
<220> FEATURE:
<223> OTHER INFORMATION: Murine Nucleotide Sequence of Light Chain CDR1

<400> SEQUENCE: 22

```
agagccagcg aatccgtcga taattatggc atttccttta tgaag                       45
```

<210> SEQ ID NO 23
<211> LENGTH: 21
<212> TYPE: DNA
<213> ORGANISM: Artificial Sequence
<220> FEATURE:
<223> OTHER INFORMATION: Murine Nucleotide Sequence of Light Chain CDR2

<400> SEQUENCE: 23

```
gctgcatcca accaagggtc c                                                 21
```

<210> SEQ ID NO 24
<211> LENGTH: 36
<212> TYPE: DNA
<213> ORGANISM: Artificial Sequence
<220> FEATURE:
<223> OTHER INFORMATION: Murine Nucleotide Sequence of Light Chain CDR3

<400> SEQUENCE: 24

```
cagcaaagca aggaggtgcc ttggacattc ggagga                                 36
```

<210> SEQ ID NO 25
<211> LENGTH: 522
<212> TYPE: PRT
<213> ORGANISM: Homo sapiens

<400> SEQUENCE: 25

Met Ala Ala Ala Ser Arg Ser Ala Ser Gly Trp Ala Leu Leu Leu Leu
1               5                   10                  15

Val Ala Leu Trp Gln Gln Arg Ala Ala Gly Ser Gly Val Phe Gln Leu
            20                  25                  30

Gln Leu Gln Glu Phe Ile Asn Glu Arg Gly Val Leu Ala Ser Gly Arg
        35                  40                  45

Pro Cys Glu Pro Gly Cys Arg Thr Phe Phe Arg Val Cys Leu Lys His
    50                  55                  60

Phe Gln Ala Val Val Ser Pro Gly Pro Cys Thr Phe Gly Thr Val Ser
65                  70                  75                  80

Thr Pro Val Leu Gly Thr Asn Ser Phe Ala Val Arg Asp Asp Ser Ser
                85                  90                  95

Gly Gly Gly Arg Asn Pro Leu Gln Leu Pro Phe Asn Phe Thr Trp Pro
            100                 105                 110

Gly Thr Phe Ser Leu Ile Ile Glu Ala Trp His Ala Pro Gly Asp Asp
        115                 120                 125

Leu Arg Pro Glu Ala Leu Pro Pro Asp Ala Leu Ile Ser Lys Ile Ala
    130                 135                 140

Ile Gln Gly Ser Leu Ala Val Gly Gln Asn Trp Leu Leu Asp Glu Gln
145                 150                 155                 160

Thr Ser Thr Leu Thr Arg Leu Arg Tyr Ser Tyr Arg Val Ile Cys Ser
                165                 170                 175

```
Asp Asn Tyr Tyr Gly Asp Asn Cys Ser Arg Leu Cys Lys Lys Arg Asn
            180                 185                 190

Asp His Phe Gly His Tyr Val Cys Gln Pro Asp Gly Asn Leu Ser Cys
            195                 200                 205

Leu Pro Gly Trp Thr Gly Glu Tyr Cys Gln Gln Pro Ile Cys Leu Ser
210                 215                 220

Gly Cys His Glu Gln Asn Gly Tyr Cys Ser Lys Pro Ala Glu Cys Leu
225                 230                 235                 240

Cys Arg Pro Gly Trp Gln Gly Arg Leu Cys Asn Glu Cys Ile Pro His
                245                 250                 255

Asn Gly Cys Arg His Gly Thr Cys Ser Thr Pro Trp Gln Cys Thr Cys
            260                 265                 270

Asp Glu Gly Trp Gly Gly Leu Phe Cys Asp Gln Asp Leu Asn Tyr Cys
            275                 280                 285

Thr His His Ser Pro Cys Lys Asn Gly Ala Thr Cys Ser Asn Ser Gly
    290                 295                 300

Gln Arg Ser Tyr Thr Cys Thr Cys Arg Pro Gly Tyr Thr Gly Val Asp
305                 310                 315                 320

Cys Glu Leu Glu Leu Ser Glu Cys Asp Ser Asn Pro Cys Arg Asn Gly
                325                 330                 335

Gly Ser Cys Lys Asp Gln Glu Asp Gly Tyr His Cys Leu Cys Pro Pro
            340                 345                 350

Gly Tyr Tyr Gly Leu His Cys Glu His Ser Thr Leu Ser Cys Ala Asp
            355                 360                 365

Ser Pro Cys Phe Asn Gly Gly Ser Cys Arg Glu Arg Asn Gln Gly Ala
    370                 375                 380

Asn Tyr Ala Cys Glu Cys Pro Pro Asn Phe Thr Gly Ser Asn Cys Glu
385                 390                 395                 400

Lys Lys Val Asp Arg Cys Thr Ser Asn Pro Cys Ala Asn Gly Gly Gln
                405                 410                 415

Cys Leu Asn Arg Gly Pro Ser Arg Met Cys Arg Cys Arg Pro Gly Phe
            420                 425                 430

Thr Gly Thr Tyr Cys Glu Leu His Val Ser Asp Cys Ala Arg Asn Pro
            435                 440                 445

Cys Ala His Gly Gly Thr Cys His Asp Leu Glu Asn Gly Leu Met Cys
    450                 455                 460

Thr Cys Pro Ala Gly Phe Ser Gly Arg Arg Cys Glu Val Arg Thr Ser
465                 470                 475                 480

Ile Asp Ala Cys Ala Ser Ser Pro Cys Phe Asn Arg Ala Thr Cys Tyr
                485                 490                 495

Thr Asp Leu Ser Thr Asp Thr Phe Val Cys Asn Cys Pro Tyr Gly Phe
            500                 505                 510

Val Gly Ser Arg Cys Glu Phe Pro Val Gly
            515                 520

<210> SEQ ID NO 26
<211> LENGTH: 63
<212> TYPE: PRT
<213> ORGANISM: Homo sapiens

<400> SEQUENCE: 26

Trp Leu Leu Asp Glu Gln Thr Ser Thr Leu Thr Arg Leu Arg Tyr Ser
1               5                   10                  15

Tyr Arg Val Ile Cys Ser Asp Asn Tyr Tyr Gly Asp Asn Cys Ser Arg
```

```
                    20                  25                  30
Leu Cys Lys Lys Arg Asn Asp His Phe Gly His Tyr Val Cys Gln Pro
            35                  40                  45
Asp Gly Asn Leu Ser Cys Leu Pro Gly Trp Thr Gly Glu Tyr Cys
        50                  55                  60
```

<210> SEQ ID NO 27
<211> LENGTH: 154
<212> TYPE: PRT
<213> ORGANISM: Homo sapiens

<400> SEQUENCE: 27

```
Met Ala Ala Ser Arg Ser Ala Ser Gly Trp Ala Leu Leu Leu Leu
1               5                   10                  15

Val Ala Leu Trp Gln Gln Arg Ala Ala Gly Ser Gly Val Phe Gln Leu
                20                  25                  30

Gln Leu Gln Glu Phe Ile Asn Glu Arg Gly Val Leu Ala Ser Gly Arg
            35                  40                  45

Pro Cys Glu Pro Gly Cys Arg Thr Phe Phe Arg Val Cys Leu Lys His
        50                  55                  60

Phe Gln Ala Val Val Ser Pro Gly Pro Cys Thr Phe Gly Thr Val Ser
65                  70                  75                  80

Thr Pro Val Leu Gly Thr Asn Ser Phe Ala Val Arg Asp Asp Ser Ser
                85                  90                  95

Gly Gly Gly Arg Asn Pro Leu Gln Leu Pro Phe Asn Phe Thr Trp Pro
                100                 105                 110

Gly Thr Phe Ser Leu Ile Ile Glu Ala Trp His Ala Pro Gly Asp Asp
            115                 120                 125

Leu Arg Pro Glu Ala Leu Pro Pro Asp Ala Leu Ile Ser Lys Ile Ala
        130                 135                 140

Ile Gln Gly Ser Leu Ala Val Gly Gln Asn
145                 150
```

<210> SEQ ID NO 28
<211> LENGTH: 138
<212> TYPE: PRT
<213> ORGANISM: Artificial Sequence
<220> FEATURE:
<223> OTHER INFORMATION: m-21M18-Vh

<400> SEQUENCE: 28

```
Met Gly Trp Ser Trp Ile Phe Leu Phe Leu Leu Ser Gly Thr Ala Gly
1               5                   10                  15

Val His Ser Glu Val Gln Leu Gln Gln Ser Gly Pro Glu Leu Val Lys
                20                  25                  30

Thr Gly Ala Ser Val Lys Ile Ser Cys Lys Ala Ser Gly Tyr Ser Phe
            35                  40                  45

Thr Ala Tyr Tyr Ile His Trp Val Lys Gln Ser His Gly Lys Ser Leu
        50                  55                  60

Glu Trp Ile Gly Tyr Ile Ser Cys Tyr Asn Gly Ala Thr Asn Tyr Asn
65                  70                  75                  80

Gln Lys Phe Lys Gly Lys Ala Thr Phe Thr Val Asp Thr Ser Ser Ser
                85                  90                  95

Thr Ala Phe Met Gln Phe Asn Ser Leu Thr Ser Glu Asp Ser Ala Val
                100                 105                 110

Tyr Tyr Cys Ala Arg Asp Tyr Asp Tyr Asp Val Gly Met Asp Tyr Trp
            115                 120                 125
```

Gly Gln Gly Thr Ser Val Thr Val Ser Ser
        130                 135

<210> SEQ ID NO 29
<211> LENGTH: 127
<212> TYPE: PRT
<213> ORGANISM: Artificial Sequence
<220> FEATURE:
<223> OTHER INFORMATION: EST-Framework

<400> SEQUENCE: 29

Met Asp Trp Thr Trp Ser Ile Leu Phe Leu Val Ala Ala Ala Thr Gly
1               5                   10                  15

Ala His Ser Gln Val Gln Leu Val Gln Ser Gly Ala Glu Val Lys Lys
            20                  25                  30

Pro Gly Ser Ser Val Lys Val Ser Cys Lys Ala Ser Gly Gly Thr Phe
        35                  40                  45

Gly Thr Tyr Ala Val Ser Trp Val Arg Gln Ala Pro Gly Gln Gly Leu
    50                  55                  60

Glu Trp Met Gly Arg Ile Ile Pro Met Leu Glu Arg Pro Asn Tyr Ala
65                  70                  75                  80

Gln Lys Phe Gln Gly Arg Val Thr Phe Thr Thr Asp Thr Ser Thr Ser
                85                  90                  95

Thr Ala Tyr Met Glu Leu Arg Ser Leu Arg Ser Asp Asp Thr Ala Val
            100                 105                 110

Tyr Tyr Cys Ala Trp Gly Gln Gly Thr Leu Val Thr Val Ser Ser
        115                 120                 125

<210> SEQ ID NO 30
<211> LENGTH: 138
<212> TYPE: PRT
<213> ORGANISM: Artificial Sequence
<220> FEATURE:
<223> OTHER INFORMATION: H7

<400> SEQUENCE: 30

Met Asp Trp Thr Trp Ser Ile Leu Phe Leu Val Ala Ala Ala Thr Gly
1               5                   10                  15

Ala His Ser Gln Val Gln Leu Val Gln Ser Gly Ala Glu Val Lys Lys
            20                  25                  30

Pro Gly Ala Ser Val Lys Ile Ser Cys Lys Ala Ser Gly Tyr Ser Phe
        35                  40                  45

Thr Ala Tyr Tyr Ile His Trp Val Lys Gln Ala Pro Gly Gln Gly Leu
    50                  55                  60

Glu Trp Ile Gly Tyr Ile Ser Ser Tyr Asn Gly Ala Thr Asn Tyr Asn
65                  70                  75                  80

Gln Lys Phe Lys Gly Arg Val Thr Phe Thr Thr Asp Thr Ser Thr Ser
                85                  90                  95

Thr Ala Tyr Met Glu Leu Arg Ser Leu Arg Ser Asp Asp Thr Ala Val
            100                 105                 110

Tyr Tyr Cys Ala Arg Asp Tyr Asp Tyr Asp Val Gly Met Asp Tyr Trp
        115                 120                 125

Gly Gln Gly Thr Leu Val Thr Val Ser Ser
        130                 135

<210> SEQ ID NO 31
<211> LENGTH: 138
<212> TYPE: PRT

<213> ORGANISM: Artificial Sequence
<220> FEATURE:
<223> OTHER INFORMATION: m-21M18-Vh

<400> SEQUENCE: 31

Met Gly Trp Ser Trp Ile Phe Leu Phe Leu Leu Ser Gly Thr Ala Gly
1               5                   10                  15

Val His Ser Glu Val Gln Leu Gln Gln Ser Gly Pro Glu Leu Val Lys
            20                  25                  30

Thr Gly Ala Ser Val Lys Ile Ser Cys Lys Ala Ser Gly Tyr Ser Phe
        35                  40                  45

Thr Ala Tyr Tyr Ile His Trp Val Lys Gln Ser His Gly Lys Ser Leu
    50                  55                  60

Glu Trp Ile Gly Tyr Ile Ser Cys Tyr Asn Gly Ala Thr Asn Tyr Asn
65                  70                  75                  80

Gln Lys Phe Lys Gly Lys Ala Thr Phe Thr Val Asp Thr Ser Ser Ser
                85                  90                  95

Thr Ala Phe Met Gln Phe Asn Ser Leu Thr Ser Glu Asp Ser Ala Val
            100                 105                 110

Tyr Tyr Cys Ala Arg Asp Tyr Asp Tyr Asp Val Gly Met Asp Tyr Trp
        115                 120                 125

Gly Gln Gly Thr Ser Val Thr Val Ser Ser
    130                 135

<210> SEQ ID NO 32
<211> LENGTH: 127
<212> TYPE: PRT
<213> ORGANISM: Artificial Sequence
<220> FEATURE:
<223> OTHER INFORMATION: h-Germline-Vh

<400> SEQUENCE: 32

Met Asp Trp Thr Trp Ser Ile Leu Phe Leu Val Ala Ala Ala Thr Gly
1               5                   10                  15

Ala His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Ser Tyr Gly Ile Ser Trp Val Arg Gln Ala Pro Gly Gln Gly Leu
    50                  55                  60

Glu Trp Met Gly Trp Ile Ser Ala Tyr Asn Gly Asn Thr Asn Tyr Ala
65                  70                  75                  80

Gln Lys Leu Gln Gly Arg Val Thr Met Thr Thr Asp Thr Ser Thr Ser
                85                  90                  95

Thr Ala Tyr Met Glu Leu Arg Ser Leu Arg Ser Asp Asp Thr Ala Val
            100                 105                 110

Tyr Tyr Cys Ala Trp Gly Gln Gly Thr Leu Val Thr Val Ser Ser
        115                 120                 125

<210> SEQ ID NO 33
<211> LENGTH: 138
<212> TYPE: PRT
<213> ORGANISM: Artificial Sequence
<220> FEATURE:
<223> OTHER INFORMATION: 21M18-H2

<400> SEQUENCE: 33

Met Asp Trp Thr Trp Ser Ile Leu Phe Leu Val Ala Ala Ala Thr Gly
1               5                   10                  15

Ala His Ser Gln Val Gln Leu Val Gln Ser Gly Ala Glu Val Lys Lys
            20                  25                  30

Pro Gly Ala Ser Val Lys Ile Ser Cys Lys Ala Ser Gly Tyr Ser Phe
        35                  40                  45

Thr Ala Tyr Tyr Ile His Trp Val Lys Gln Ala Pro Gly Gln Gly Leu
 50                  55                  60

Glu Trp Ile Gly Tyr Ile Ser Cys Tyr Asn Gly Ala Thr Asn Tyr Asn
65                  70                  75                  80

Gln Lys Phe Lys Gly Arg Val Thr Phe Thr Thr Asp Thr Ser Thr Ser
                85                  90                  95

Thr Ala Tyr Met Glu Leu Arg Ser Leu Arg Ser Asp Asp Thr Ala Val
            100                 105                 110

Tyr Tyr Cys Ala Arg Asp Tyr Asp Tyr Asp Val Gly Met Asp Tyr Trp
        115                 120                 125

Gly Gln Gly Thr Leu Val Thr Val Ser Ser
    130                 135

<210> SEQ ID NO 34
<211> LENGTH: 131
<212> TYPE: PRT
<213> ORGANISM: Artificial Sequence
<220> FEATURE:
<223> OTHER INFORMATION: m-21M18-Vk

<400> SEQUENCE: 34

Met Glu Ser Asp Thr Leu Leu Leu Trp Val Leu Leu Leu Trp Val Pro
1               5                   10                  15

Gly Ser Lys Gly Asp Ile Val Leu Thr Gln Ser Pro Ala Ser Leu Ala
            20                  25                  30

Val Ser Leu Gly Gln Arg Ala Thr Ile Ser Cys Arg Ala Ser Glu Ser
        35                  40                  45

Val Asp Asn Tyr Gly Ile Ser Phe Met Lys Trp Phe Gln Gln Lys Pro
 50                  55                  60

Gly Gln Pro Pro Lys Leu Leu Ile Tyr Ala Ala Ser Asn Gln Gly Ser
65                  70                  75                  80

Gly Val Pro Ala Arg Phe Ser Gly Ser Gly Ser Gly Thr Asp Phe Ser
                85                  90                  95

Leu Asn Ile His Pro Met Glu Asp Asp Thr Ala Met Tyr Phe Cys
            100                 105                 110

Gln Gln Ser Lys Glu Val Pro Trp Thr Phe Gly Gly Gly Thr Lys Leu
        115                 120                 125

Glu Ile Lys
    130

<210> SEQ ID NO 35
<211> LENGTH: 134
<212> TYPE: PRT
<213> ORGANISM: Artificial Sequence
<220> FEATURE:
<223> OTHER INFORMATION: h-germline-Vk

<400> SEQUENCE: 35

Met Val Leu Gln Thr Gln Val Phe Ile Ser Leu Leu Leu Trp Ile Ser
1               5                   10                  15

Gly Ala Tyr Gly Asp Ile Val Met Thr Gln Ser Pro Asp Ser Leu Ala
            20                  25                  30

Val Ser Leu Gly Glu Arg Ala Thr Ile Asn Cys Lys Ser Ser Gln Ser

-continued

```
                35                  40                  45
Val Leu Tyr Ser Ser Asn Asn Lys Asn Tyr Leu Ala Trp Tyr Gln Gln
        50                  55                  60

Lys Pro Gly Gln Pro Pro Lys Leu Leu Ile Tyr Trp Ala Ser Thr Arg
65                  70                  75                  80

Glu Ser Gly Val Pro Asp Arg Phe Ser Gly Ser Gly Ser Gly Thr Asp
                85                  90                  95

Phe Thr Leu Thr Ile Ser Ser Leu Gln Ala Glu Asp Val Ala Val Tyr
            100                 105                 110

Tyr Cys Gln Gln Tyr Tyr Ser Thr Pro Pro Trp Thr Phe Gly Gln Gly
        115                 120                 125

Thr Lys Val Glu Ile Lys
        130

<210> SEQ ID NO 36
<211> LENGTH: 131
<212> TYPE: PRT
<213> ORGANISM: Artificial Sequence
<220> FEATURE:
<223> OTHER INFORMATION: 21M18-L2

<400> SEQUENCE: 36

Met Val Leu Gln Thr Gln Val Phe Ile Ser Leu Leu Leu Trp Ile Ser
1               5                   10                  15

Gly Ala Tyr Gly Asp Ile Val Met Thr Gln Ser Pro Asp Ser Leu Ala
                20                  25                  30

Val Ser Leu Gly Glu Arg Ala Thr Ile Ser Cys Arg Ala Ser Glu Ser
            35                  40                  45

Val Asp Asn Tyr Gly Ile Ser Phe Met Lys Trp Phe Gln Gln Lys Pro
        50                  55                  60

Gly Gln Pro Pro Lys Leu Leu Ile Tyr Ala Ala Ser Asn Gln Gly Ser
65                  70                  75                  80

Gly Val Pro Asp Arg Phe Ser Gly Ser Gly Ser Gly Thr Asp Phe Thr
                85                  90                  95

Leu Thr Ile Ser Ser Leu Gln Ala Glu Asp Val Ala Val Tyr Tyr Cys
            100                 105                 110

Gln Gln Ser Lys Glu Val Pro Trp Thr Phe Gly Gly Gly Thr Lys Val
        115                 120                 125

Glu Ile Lys
        130
```